United States Patent
Romesberg et al.

(10) Patent No.: US 11,761,007 B2
(45) Date of Patent: Sep. 19, 2023

(54) PRODUCTION OF UNNATURAL NUCLEOTIDES USING A CRISPR/CAS9 SYSTEM

(71) Applicant: The Scripps Research Institute, La Jolla, CA (US)

(72) Inventors: Floyd E. Romesberg, La Jolla, CA (US); Brian Lamb, San Diego, CA (US); Yorke Zhang, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 284 days.

(21) Appl. No.: 16/063,107

(22) PCT Filed: Dec. 16, 2016

(86) PCT No.: PCT/US2016/067353
§ 371 (c)(1),
(2) Date: Jun. 15, 2018

(87) PCT Pub. No.: WO2017/106767
PCT Pub. Date: Jun. 22, 2017

(65) Prior Publication Data
US 2020/0377877 A1    Dec. 3, 2020

Related U.S. Application Data

(60) Provisional application No. 62/269,890, filed on Dec. 18, 2015.

(51) Int. Cl.
| | |
|---|---|
| *C12N 15/63* | (2006.01) |
| *C12N 9/22* | (2006.01) |
| *C12N 15/11* | (2006.01) |
| *C12N 15/70* | (2006.01) |
| *C12N 5/10* | (2006.01) |

(52) U.S. Cl.
CPC .............. *C12N 15/63* (2013.01); *C12N 5/10* (2013.01); *C12N 9/22* (2013.01); *C12N 15/11* (2013.01); *C12N 15/70* (2013.01); *C12N 2310/20* (2017.05); *C12N 2310/3519* (2013.01)

(58) Field of Classification Search
CPC .......... C12N 15/11; C12N 9/22; C12N 15/70; C12N 2310/20; C12N 2310/3519; C12N 15/63; C12N 5/10
USPC ........... 435/325, 320.1, 455; 536/23.2, 29.13
See application file for complete search history.

(56) References Cited

U.S. PATENT DOCUMENTS

| | | |
|---|---|---|
| 3,687,808 A | 8/1972 | Thomas, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,683,195 A | 7/1987 | Mullis et al. |
| 4,683,202 A | 7/1987 | Mullis |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,849,513 A | 7/1989 | Smith et al. |
| 4,876,335 A | 10/1989 | Yamane et al. |
| 4,904,582 A | 2/1990 | Tullis |
| 4,910,300 A | 3/1990 | Urdea et al. |
| 4,948,882 A | 8/1990 | Ruth |
| 4,958,013 A | 9/1990 | Letsinger |
| 4,965,188 A | 10/1990 | Mullis et al. |
| 4,981,957 A | 1/1991 | Lebleu et al. |
| 5,015,733 A | 5/1991 | Smith et al. |
| 5,023,243 A | 6/1991 | Tullis |
| 5,034,506 A | 7/1991 | Summerton et al. |
| 5,082,830 A | 1/1992 | Brakel et al. |
| 5,093,232 A | 3/1992 | Urdea et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |

(Continued)

FOREIGN PATENT DOCUMENTS

| | | |
|---|---|---|
| EP | 0614907 A1 | 9/1994 |
| EP | 0629633 A2 | 12/1994 |

(Continued)

OTHER PUBLICATIONS

Hsu PD, Scott DA, Weinstein JA, Ran FA, Konermann S, Agarwala V, Li Y, Fine EJ, Wu X, Shalem O, Cradick TJ, Marraffini LA, Bao G, Zhang F. DNA targeting specificity of RNA-guided Cas9 nucleases. Nat Biotechnol. Sep. 2013;31(9):827-32. Epub Jul. 21, 2013 (Year: 2013).*

Hsu PD, Scott DA, Weinstein JA, Ran FA, Konermann S, Agarwala V, Li Y, Fine EJ, Wu X, Shalem O, Cradick TJ, Marraffini LA, Bao G, Zhang F. DNA targeting specificity of RNA-guided Cas9 nucleases. Nat Biotechnol. Sep. 2013;31(9):827-32. Supplementary Information (Year: 2013).*

Hsu, P. D., Lander, E. S., & Zhang, F. Development and applications of CRISPR-Cas9 for genome engineering. Cell, 2014; 157(6), 1262-1278. (Year: 2014).*

(Continued)

*Primary Examiner* — Christopher M Babic
*Assistant Examiner* — Kimberly A Aron
(74) *Attorney, Agent, or Firm* — WILSON SONSINI GOODRICH & ROSATI

(57) ABSTRACT

Disclosed herein are methods, cells, engineered microorganisms, and kits for increased production of a nucleic acid molecule that comprises an unnatural nucleotide.

11 Claims, 9 Drawing Sheets

Specification includes a Sequence Listing.

(56) References Cited

U.S. PATENT DOCUMENTS

| | | |
|---|---|---|
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,899 A | 1/1997 | Sato et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,648,247 A | 7/1997 | Picataggio et al. |
| 5,656,493 A | 8/1997 | Mullis et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,830,653 A | 11/1998 | Froehler et al. |
| 5,888,732 A | 3/1999 | Hartley et al. |
| 6,005,096 A | 12/1999 | Matteucci et al. |
| 6,143,557 A | 11/2000 | Hartley et al. |
| 6,171,861 B1 | 1/2001 | Hartley et al. |
| 6,268,490 B1 | 7/2001 | Imanishi et al. |
| 6,270,969 B1 | 8/2001 | Hartley et al. |
| 6,277,608 B1 | 8/2001 | Hartley et al. |
| 6,525,191 B1 | 2/2003 | Ramasamy |
| 6,670,461 B1 | 12/2003 | Wengel |
| 6,720,140 B1 | 4/2004 | Hartley et al. |
| 6,770,748 B2 | 8/2004 | Imanishi et al. |
| 6,794,499 B2 | 9/2004 | Wengel et al. |
| 6,955,807 B1 | 10/2005 | Shanafelt et al. |
| 7,034,133 B2 | 4/2006 | Wengel et al. |
| 7,053,207 B2 | 5/2006 | Wengel |
| 7,399,845 B2 | 7/2008 | Swayze et al. |
| 7,427,672 B2 | 9/2008 | Imanishi et al. |
| 7,670,823 B1 | 3/2010 | Hartley et al. |
| 8,501,805 B2 | 8/2013 | Seth et al. |
| 8,546,556 B2 | 10/2013 | Seth et al. |
| 10,696,719 B2 | 6/2020 | Romesberg et al. |
| 10,696,720 B2 | 6/2020 | Romesberg et al. |
| 2002/0007051 A1 | 1/2002 | Cheo et al. |
| 2004/0171570 A1 | 9/2004 | Allerson et al. |
| 2005/0130923 A1 | 6/2005 | Bhat et al. |
| 2006/0074035 A1 | 4/2006 | Hong et al. |
| 2007/0287831 A1 | 12/2007 | Seth et al. |
| 2008/0039618 A1 | 2/2008 | Allerson et al. |
| 2008/0300163 A1 | 12/2008 | Cho et al. |
| 2012/0077252 A1 | 3/2012 | Picataggio et al. |
| 2012/0244112 A1 | 9/2012 | Ast et al. |
| 2014/0068797 A1 | 3/2014 | Doudna et al. |
| 2014/0273226 A1 | 9/2014 | Wu et al. |
| 2014/0328791 A1 | 11/2014 | Bossard et al. |

(56) References Cited

U.S. PATENT DOCUMENTS

| | | |
|---|---|---|
| 2016/0168187 A1 | 6/2016 | Romesberg et al. |
| 2017/0029829 A1 | 2/2017 | Romesberg et al. |
| 2017/0369871 A1 | 12/2017 | Ptacin et al. |
| 2019/0218257 A1 | 7/2019 | Romesberg et al. |
| 2019/0376054 A1 | 12/2019 | Ptacin et al. |
| 2020/0024597 A1 | 1/2020 | Ptacin et al. |
| 2020/0095591 A1 | 3/2020 | Romesberg et al. |
| 2020/0131555 A1 | 4/2020 | Ptacin et al. |
| 2020/0224234 A1 | 7/2020 | Romesberg et al. |
| 2020/0277342 A1 | 9/2020 | Romesberg et al. |
| 2020/0318122 A1 | 10/2020 | Romesberg et al. |
| 2020/0392550 A1 | 12/2020 | Romesberg et al. |
| 2021/0222147 A1 | 7/2021 | Ptacin et al. |
| 2022/0228148 A1 | 7/2022 | Romesberg et al. |
| 2022/0243244 A1 | 8/2022 | Romesberg et al. |

FOREIGN PATENT DOCUMENTS

| | | | | |
|---|---|---|---|---|
| EP | 2487181 A1 * | 8/2012 | ............ | C07H 21/02 |
| WO | WO-9414226 A1 | 6/1994 | | |
| WO | WO-9735869 A1 | 10/1997 | | |
| WO | WO-9962923 A2 | 12/1999 | | |
| WO | WO-0105801 A1 | 1/2001 | | |
| WO | WO-0132887 A1 | 5/2001 | | |
| WO | WO-02070533 A2 | 9/2002 | | |
| WO | WO-2004007713 A1 | 1/2004 | | |
| WO | WO-2004106356 A1 | 12/2004 | | |
| WO | WO-2005021570 A1 | 3/2005 | | |
| WO | WO-2005026187 A1 | 3/2005 | | |
| WO | WO-2005045015 A2 | 5/2005 | | |
| WO | WO-2006049297 A1 | 5/2006 | | |
| WO | WO-2007015557 A1 | 2/2007 | | |
| WO | WO-2007066737 A1 | 6/2007 | | |
| WO | WO-2007090071 A2 | 8/2007 | | |
| WO | WO-2007134181 A2 | 11/2007 | | |
| WO | WO-2008101157 A1 | 8/2008 | | |
| WO | WO-2008150729 A2 | 12/2008 | | |
| WO | WO-2008154401 A2 | 12/2008 | | |
| WO | WO-2009006478 A2 | 1/2009 | | |
| WO | WO-2009123216 A1 | 10/2009 | | |
| WO | WO-2011043385 A1 | 4/2011 | | |
| WO | WO-2011139699 A2 | 11/2011 | | |
| WO | WO-2014093712 A1 * | 6/2014 | ............ | C12N 15/86 |
| WO | WO-2015021432 A1 | 2/2015 | | |
| WO | WO-2015026885 A1 * | 2/2015 | ........... | C12N 15/113 |
| WO | WO-2015157555 A2 | 10/2015 | | |
| WO | WO-2016115168 A1 | 7/2016 | | |
| WO | WO-2017024047 A1 * | 2/2017 | ............... | C12N 9/22 |
| WO | WO-2017106767 A1 | 6/2017 | | |
| WO | WO-2017223528 A1 | 12/2017 | | |
| WO | WO-2019014262 A1 | 1/2019 | | |
| WO | WO-2019014267 A1 | 1/2019 | | |
| WO | WO-2019133883 A1 | 7/2019 | | |
| WO | WO-2021067313 A1 | 4/2021 | | |
| WO | WO-2022087475 A1 | 4/2022 | | |

OTHER PUBLICATIONS

Hirao, I., Kimoto, M., & Yamashige, R. Natural versus artificial creation of base pairs in DNA: Origin of nucleobases from the perspectives of unnatural base pair studies. Accounts of Chemical Research, 2012; 45(12), 2055-2065. (Year: 2012).*
Ran, FA, Hsu, PD, Lin, C-Y, et al. Double Nicking by RNA-Guided CRISPR Cas9 for Enhanced Genome Editing Specificity. Cell, vol. 155, Issue 2, Oct. 10, 2013, pp. 479-480. (Year: 2013).*
Jiang, Y, et al. Multigene Editing in the *Escherichia coli* Genome via the CRISPR-Cas9 System. Applied and Environmental Microbiology Mar. 2015, 81 (7) 2506-2514 and Supplemental Material (Year: 2015).*
Kimoto, M., & Hirao, I. Creation of unnatural base pair systems toward new DNA/RNA biotechnologies. In Chemical Biology of Nucleic Acids, pp. 131-148; Mar. 28, 2014; Springer, Berlin, Heidelberg. (Year: 2014).*
Malyshev, D., Dhami, K., Lavergne, T. et al. A semi-synthetic organism with an expanded genetic alphabet. Nature 2014; 509, 385-8. (Year: 2014).*
Hirao, I., Kimoto, M., & Yamashige, R. (2012). Natural versus artificial creation of base pairs in DNA: Origin of nucleobases from the perspectives of unnatural base pair studies. Accounts of chemical research, 45(12), 2055-2065 (Year: 2012).*
Hirao, I. (2014). Synthetic Genetic Polymers Functioning to Store and Propagate Information by Genetic Alphabet Expansion. In Reviews in Cell Biology and Molecular Medicine, R.A. Meyers (Ed.). (Year: 2014).*
Li, L., Degardin, M., Lavergne, T., et al. Natural-like replication of an unnatural base pair for the expansion of the genetic alphabet and biotechnology applications. J. Am. Chem. Soc. 2014, 136(3) 826-9 Publication Date: Oct. 23, 2013 (Year: 2014).*
Hsu PD, Scott DA, Weinstein JA, Ran FA, Konermann S, Agarwala V, Li Y, Fine EJ, Wu X, Shalem O, Cradick TJ. DNA targeting specificity of RNA-guided Cas9 nucleases. Nature biotechnology. Sep. 2013;31(9):827-32. (Year: 2013).*
Carroll D. Staying on target with CRISPR-Cas. Nature biotechnology. Sep. 2013;31(9):807-9. (Year: 2013).*
Sitaraman K, Esposito D, Klarmann G, Le Grice SF, Hartley JL, Chatterjee Dk. A novel cell-free protein synthesis system. Journal of biotechnology. Jun. 10, 2004;110(3):257-63 (Year: 2004).*
Ran, F. A. F. A., Hsu, P. D., Wright, J., Agarwala, V., Scott, D. A., & Zhang, F. (2013). Genome engineering using the CRISPR-Cas9 system. Nature protocols, 8(11), 2281-2308. (Year: 2013).*
Kimoto M., Hirao I. (2014). Creation of unnatural base pair systems toward new DNA/RNA biotechnologies. Chemical Biology of Nucleic Acids, 2014; 131-48 (Year: 2014).*
Jiang, Y., Chen, B., Duan, C., Sun, B., Yang, J., & Yang, S. (2015). Multigene editing in the *Escherichia coli* genome via the CRISPR-Cas9 system. Applied and environmental microbiology, 81(7), 2506-2514. (Year: 2015).*
Malyshev, D. A., Dhami, K., Lavergne, T., Chen, T., Dai, N., Foster, J. M., . . . & Romesberg, F. E. (2014). A semi-synthetic organism with an expanded genetic alphabet. Nature, 509(7500), 385-388. (Year: 2014).*
Arenas-Ramirez et al. Improved cancer immunotherapy by a CD25-mimobody conferring selectivity to human interleukin-2. Sci Transl Med 8:367ra166 (Nov. 30, 2016). 13 pages.
Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).
Bhatt et al. Peripheral Blood Lymphocyte Responses in Patients with Renal Cell Carcinoma treated with High-Dose Interleukin-2. Poster (SITC 2018).
Biocentury Innovations publication Oct. 27, 2016 (26 pgs).
Boyman et al. Selective Stimulation of T Cell subsets with Antibody-Cytokine Immune Complexes. Science 311:1924-1927 (2006).
Boyman et al. Selectively Expanding Subsets of T Cells in Mice by Injection of Interleukin-2/Antibody Complexes: Implications for Transplantation Tolerance. Transplantation Proceedings 44:1032-1034 (2012).
Boyman et al. The role of interleukin-2 during homeostatis and activation of the immune system. Nature 12:180-190 (2012).
Branca. Rekindling cancer vaccines. Nat Biotechnol 34(10):1019-1025 (2016).
Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).
Charych et al. NKTR-214, an Engineered Cytokine with Biased IL2 Receptor Binding, Increased Tumor Exposure, and Marked Efficacy in Mouse Tumor Models. Clin Cancer Res 22(3):680-690 (2016) (w/Supplemental Figures).
Chastgner et al. Lack of intermediate-affinity interleukin-2 receptor in mice leads to dependence on interkeukin-2 receptor α,β and γ chain expression for T cell growth. Eur J Immunol 26:201-206 (1996).

(56) References Cited

OTHER PUBLICATIONS

Chatzkel et al. Coordinated pembrolizumab and high dose IL-2 (5-in-a-row schedule) for therapy of metastatic clear cell renal cancer: a single-center, single-arm trial. Poster Abstract No. 244333 (2010).
Chen et al. A novel human IL-2 mutein with minimal systemic toxicity exerts greater antitumor efficacy than wild-type IL-2. Cell Death& Disease 9:989 (2018).
Diab et al. NKTR-214 (CD-122-biased agonist) plus nivolumab in patients with advanced solid tumors: Preliminary phase 1/2 results of PIVOT. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).
Dranoff. Cytokines in cancer pathogenesis and cancer therapy. Nature Reviews Cancer 4:11-22 (2004).
Floros et al. Anticancer Cytokines: Biology and Clinical Effects of Interferon-α2, Interleukin (IL)-2, IL-15, IL-21, and IL-12. Semin Oncol 42(4):539-548 (2015).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53:2597-2602 (1993).
Hu et al. The Generation of Low Toxicity Interleukin-2 Fusion Proteins Devoid of Vasopermeability Activity. Blood 101(12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Insight-Esprit Study Group et al. Interleukin-2 Therapy in Patients with HIV Infection. N Engl J Med. 361(16):1548-59 (2009).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).
Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (Apr. 2, 2019).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Kivimäe et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).
Kivimäe et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines. Oncoimmunology 6(3):e1277306 (2017).
Krieg et al. Improved IL-2 immunotherapy by selective stimulation of IL-2 receptors on lymphocytes and endothelial cells. PNAS USA 107(26):11906-11911 (Jun. 29, 2010).
Langowski et al. The CD122-biased immunostimulatory cytokine NKTR-214 combined with checkpoint blockade leads to mobilization of anti-tumor immunity and synergistic activity. Poster Abstract 311. 2016 CR-CIMT-EATIR-AACR Cancer Immunotherapy Conference (2016).
Lazear et al. Targeting of IL-2 to cytotoxic lymphocytes as an improved method of cytokine-driven immunotherapy. Oncoimmunology 6(2):e1265721 (2017).
Letourneau et al. IL-2/anti-IL-2 antibody complexes show strong biological activity by avoiding interaction with IL-2 receptor alpha subunit CD25. PNAS USA 107:2171-2176 (2010).
Lopes et al. Characterization of the Pharmacodynamic Immune Response to a Novel Immunotherapeutic Agent, ALKS 4230, in Mice and Non-Human Primates. Poster 22 (Abstract #2663) (AACR 2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (AACR 2015).
Lotze et al. In vivo administration of purified human interleukin 2. II. Half life, immunologic effects, and expansion of peripheral lymphoid cells in vivo with recombinant IL 2. J Immunol 135:2865-2875 (1985).
Lou et al. Fixing vascular leak in IL-2 immunotherapy. SciBX 3(27):2 pgs (2010).
Meghnem et al. Cutting Edge: Differential Fine-Tuning of IL-2- and IL-15-Dependent Functions by Targeting Their Common IL-2/15Rβ/γc Receptor. J Immunol 198(12):4563-4568 (May 2017).
Melero et al. Clinical activity safety, and PK/PD from a Phase 1 study of RO6874281, a fibroblast activation protein (FAP) targeted interleukin-2 variant (IL-cv). ESMO 2018 Congress Poster (Oct. 20, 2018).
Merchant et al. Preclinical characterization of IL-2 Superkines engineered with biased CD8+ T cell stimulating properties. Poster (SITC 2018).
Milla et al. THOR-707: An engineered IL-2 for the treatment of solid tumors with superior pre- clinical efficacy and safety evidence. 2018 Society for Immunotherapy of Cancer (SITC) 33rd Annual Meeting Poster (Nov. 9, 2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (May 15, 2019).
Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.
Nektar Therapeutics. Investor Meeting presentation Jun. 3, 2017.
Nicolini et al. The FAP-IL2v Immunocytokine is a Versatile Combination Partner for Cancer Immunotherapy. Poster (SITC 2018).
Parisi et al. Enhanced expansion and tumor targeting of adoptively transferred T cells with NKTR-214. Poster Abstract #3566. (AACR Apr. 17, 2018).
Pfannenstiel et al. A Novel, Individualized Xenograft Model of Cancer Immunotherapy and Tumor Growth Inhibition by ALKS 4230. Poster #P351 (SITC 2017).

(56) References Cited

OTHER PUBLICATIONS

Pieper et al. NKTR-214 in combination with radiation produces a potent in situ vaccine in the syngeneic B78 melanoma model. Poster (STIC 2018).
Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).
Roessler et al. Cooperative interactions between the interleukin 2 receptor α and β chains later the interleukin 2-binding affinity of the receptor subunits. PNAS USA 91:3344-3347 (1994).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).
Sharma et al. NKTR-214 enhances anti-tumor T cell immune responses induced by checkpoint blockade or vaccination. Poster (SITC 2017).
Siegel et al. Interleukin-2 Toxicity. J Clin Oncol 9(4):694-704 (1991).
Sim et al. IL2 Variant Circumvents ICOS+ Regulatory T-cell Expansion and Promotes NK Cell Activation. Cancer Immunol Res. 4(11):983-995 (Nov. 2016).
Sivakumar et al. Comparison of Vascular Leak Syndrome in Mice treated with IL21 or IL2. Comparative Medicine 63(1):13-21 (2013).
Spangler et al. Antibodies to Interleukin-2 Elicit Selective T Cell Subset Potentiation through Distinct Conformational Mechanism. Immunity 42:815-825 (2015).
Stauber et al. Crystal Structure of the IL-2 signaling complex: Paradigm for a heterotrimeric cytokine receptor. PNAS 103(8):2788-2793 (2006).
Sun et al. First-In-Human dose Selection of ALKS 4230, an Investigational Immunotherapeutic Agent. Poster 4088 (AACR 2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).
Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).
Synthorx, Inc. Commission File No. 001-38756. Form 10-Q Quarterly Report Pursuant to Section 13 or 15(d) of the Securities Exchange Act of 1934 for Quarterly Period Ended Mar. 31, 2019.
Synthorx, Inc. Commission File No. 001-38756. Form 8-K Current Report Pursuant to Section 13 or 15(d) of the Securities Exchange Act of 1934 dated Apr. 2, 2019 (8 pgs).
Synthorx, Inc. Commission File No. 001-38756. Form 8-K Current Report Pursuant to Section 13 or 15(d) of the Securities Exchange Act of 1934 dated May 31, 2019 (15 pgs).
Synthorx, Inc. Registration No. 333-228355. Amendment No. 1 to Form S-1 Registration Statement Under The Securities Act of 1933 filed Nov. 27, 2018 (355 pgs.).
U.S. Appl. No. 15/543,217 Office Action dated Apr. 3, 2020 .
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,209, filed May 15, 2019.
U.S. Appl. No. 16/413,219, filed May 15, 2019.
U.S. Appl. No. 16/434,999, filed Jun. 7, 2019.
U.S. Appl. No. 16/518,715, filed Jul. 22, 2019.
U.S. Appl. No. 16/530,742, filed Aug. 2, 2019.
U.S. Appl. No. 16/535,992, filed Aug. 8, 2019.
U.S. Appl. No. 16/546,097, filed Aug. 20, 2019.
U.S. Appl. No. 16/546,100, filed Aug. 20, 2019 .
U.S. Appl. No. 16/577,347, filed Sep. 9, 2020.
U.S. Appl. No. 16/591,422, filed Oct. 2, 2019.
U.S. Appl. No. 16/839,741, filed Apr. 3, 2020.
U.S. Appl. No. 16/900,154, filed Jun. 12, 2020.

Vaishampayan et al. A Phase 1 Trial of ALKS 4230, an Engineered Cytokine Activator of NK and Effector T Cells, in Patients with Advanced Solid Tumors. Poster for Abstract #TPS3111 (ASCO 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Van Gool et al. Interleukin-5-producing group 2 innate lymphoid cells control eosinophilia induced by interleukin-2 therapy. Blood 124(24):3572-3576 (2014).
Van Haelst Pinsani et al. Administration of Interleukin-2 (IL-2) Results in Increased Plasma Concentrations of IL-5 and Eosinophilia in Patients with Cancer. Blood 78:1538-1544 (1991).
Vazquez-Lombardi et al. Potent antitumour activity of the interleukin-2-Fc fusion proteins requires Fc-mediated depletion of regulatory T-cells. Nat Comm 8:15373 (2017).
Waldmann et al. The Shared and Contrasting Roles of IL2 and IL15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (SITC 2017).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with Its α, β, and γc Receptors. Science 310:1159-63 (2005).
Webster et al. In vivo expansion of T reg cells with IL-2-mAb complexes: induction of resistance to EAE and long-term acceptance of islet allografts without immunosuppression. J Med Chem 206(4):751-760 (2009).
Yamaguchi et al. Role of IL-5 in IL-2-induced eosinophilia. In vivo and in vitro expression of IL-5 mRNA by IL-2. J Immunol 145:873-877 (1990).
Zalevsky. Jefferies 2016 Global Healthcare Conference. PowerPoint presentation (Nov. 16, 2016).
Fourrey et al. S-Nucleoside photorearrangement. Access to pyridine pseudonucleosides. J. Org. Chem. 44(11):1902-1894 (1979).
Acsadi et al. Human Dystrophin Expression in mdx Mice After Intramuscular Injection of DNA Constructs. Nature 352:815-818 (1991).
Akbergenov et al. ARC-1, a sequence element complementary to an internal 18S rRNA segment, enhances translation efficiency in plants when present in the leader or intercistronic region of mRNAs. Nucleic Acids Res 32(1):239-247 (2004).
Arie et al. Phylogenetic identification of n-alkane assimilating Candida yeasts based on nucleotide divergence in the 59 end of LSU rDNA gene. J Gen Appl Microbiol. 46(5):257-262 (2000).
Beigelman et al. Synthesis of 5'-C-Methyl-D-allo- & L-Talo-ribonucleoside 3' -O-Phosphoramidites & Their Incorporation into Hammerhead Ribozymes. Nucleosides and Nucleotides 14(3-5):901-905 (1995).
Betz et al. Structural insights into DNA replication without hydrogen bonds. J Am Chem Soc 135:18637-18643 (2013).
Bohringer et al. Synthesis of 5'-deoxy-5'-methylphosphonate linked thymidine oligonucleotides. Tet Lett 34:2723-2726 (1993).
Bordo et al. Suggestions for "safe" residue substitutions in site-directed mutagenesis. J Mol Biol 217:721-729 (1991) .
Braasch et al. Locked nucleic acid (LNA): fine-tuning the recognition of DNA and RNA. Chem Bio 8:1-7 (2001).
Cann et al. A heterodimeric DNA polymerase: Evidence that members of Euryarchaeota possess a distinct DNA polymerase. PNAS USA 95:14250 (1998).
Cariello et al. Fidelity of Thermococcus litoralis DNA polymerase (VentTM) in PCR determined by denaturing gradient gel electrophoresis Nucl Acid Res 19:4193-4198 (1991).
Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).

(56) References Cited

OTHER PUBLICATIONS

Chen et al. Directed polymerase evolution. FEBS Lett. 588(2):219-229 (2014).
Chen et al. Phosphonate Analogues of Cytosine Arabinoside Monophosphate. Phosphorus, Sulfur and Silicon 177:1783-1786 (2002).
Chien et al. Deoxyribonucleic acid polymerase from the extreme thermophile Thermus aquaticus. J Bacteriol 127:1550-1557 (1976).
Collingwood et al. The Synthesis and Incorporation in Oligonucleotides of a Thymidine Dimer Containing an Internucleoside Phosphinate Linkage. Synlett 7:703-705 (1995).
Crooke et al. Pharmacokinetic properties of several novel oligonucleotide analogs in mice. J Pharmacol Exp Ther 277:923-937 (1996).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11)1287-1290 (1997).
Diaz et al. Accuracy of replication in the polymerase chain reaction. Comparison between Thermotoga maritima DNA polymerase and Thermus aquaticus DNA polymerase. Braz J Med Res 31:1239-1242 (1998).
Elayadi et al. Application of PNA and LNA oligomers to chemotherapy. Curr Opinion Invens Drugs 2:558-561 (2001).
Ellington et al. In vitro selection of RNA molecules that bind specific ligands. Nature 346:818-822 (1990).
Englisch et al. Chemically Modified Oligonucleotides as Probes and Inhibitors. Angew. Chem. Int. Ed. Eng. 30:613-629 (1991).
Eppacher et al. Synthesis and Incorporation of C(5')-Ethynylated Uracil-Derived Phosphoramidites into RNA. Helvetica Chimica Acta 87:3004-3020 (2004).
Fairhurst et al. Synthesis and Hybridisation Properties of Phosphonamidate Ester Modified Nucleic Acid. Synlett 4:467-472 (2001).
Fersht. Enzyme Structure and Mechanism, 2nd ed., W. H. Freeman & Co., New York (pp. 350-351) (1985).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of eIF4F. Nucleic Acids Res 30(15):3401-3411 (2002).
Gallier et al. Ex-Chiral-Pool Synthesis of β-Hydroxyphosphonate Nucleoside Analogues. Eur J Org Chem 6:925-933 (2007).
Gardner et al. Comparative Kinetics of Nucleotide Analog Incorporation by Vent DNA Polymerase. J Biol Chem 279(12):11834-11842 (2004).
Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J Am Chem Soc 105(26):7638-7640 (1983).
Goldberg et al. Re: Z. Ram et al. In situ retroviral-mediated gene transfer for the treatment of brain tumors in rats. Cancer Res. 53:83-88 (1993).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).
Hampton et al. Design of substrate-site-directed irreversible inhibitors of adenosine 5'- phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and pyrophosphoryl anhydrides and studies of their interactions with adenine nucleotide utilizing enzymes. J Am Chem Soc 95(13):4404-4414 (1973).
Hayes et al. Combining computational and experimental screening for rapid optimization of protein properties. PNAS USA 99:15926-15931 (2002).
Hinnisdaels et al. Direct cloning of PCR products amplified with Pwo DNA polymerase. Biotechniques 20:186-188 (1996).
Hutter et al. From Phosphate to Bis(methylene) Sulfone: Non-Ionic Backbone Linkers in DNA. Helvetica Chimica Acta 85:2777-2806 (2002).
Jager et al. Oligonucleotide N-alkylphosphoramidates: synthesis and binding to polynucleotides. Biochemistry 27:7247-7246 (1988).
Jinek et al. A programmable dual-RNA-guided DNA endonuclease in adaptive bacterial immunity. Science 337:816-821 (2012).
Juncosa-Ginesta et al. Improved efficiency in site-directed mutagenesis by PCR using a *Pyrococcus* sp. GB-D polymerase. Biotechniques 16:820-823 (1994).
Jung et al. Synthesis of phosphonate derivatives of uridine, cytidine, and cytosine arabinoside. Bioorg Med Chem 8:2501-2509 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kroschwitz. The Concise Encyclopedia Of Polymer Science And Engineering. (pp. 858-859) (1990).
Kumar et al. The First Analogues of LNA (Locked Nucleic Acids): Phosphorothioate LNA and 2'-Thio-LNA. Bioorg Med Chem Lett 8:2219-2222 (1998).
Landy. Mechanistic and structural complexity in the site-specific recombination pathways of Int and FLP. Curr Opin Genet Dev. 3(5):699-707 (1993).
Lecomte et al. Selective Inactivation of the 3' to 5' exonuclease activity of *Escherichia coli* DNA polymerase I by heat. Nucl Acids Res 11:7505-7515 (1983).
Letsinger et al. Cholesteryl-conjugated oligonucleotides: Synthesis, properties, and activity as inhibitors of replication of human immunodeficiency virus in cell culture. PNAS 86:6553-6556 (1989).
Levin. It's prime time for reverse transcriptase. Cell 88:5-8 (1997).
Liu et al. Adding new chemistries to the genetic code. Annu Rev Biochem 79:413-444 (2010).
Lundberg et al. High-fidelity amplification using a thermostable DNA polymerase isolated from Pyrococcus furiosus. Gene 108:1-6 (1991).
Mali et al. RNA-Guided Human Genome Engineering via Cas9. Science 339:823-826 (2013).
Malyshev et al. A semi-synthetic organism with an expanded genetic alphabet. Nature 509(7500):385-388 (2014).
Malyshev et al. The expanded genetic alphabet. Angew Chem Int Ed Engl 54:11930-11944 (2015).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).

(56) References Cited

OTHER PUBLICATIONS

Micklefield. Backbone Modification of Nucleic Acids: Synthesis, Structure and Therapeutic Applications. Current Medicinal Chemistry 8:1157-1179 (2001).
Mignone et al. Untranslated regions of mRNAs. Genome Biol. 3(3):Reviews0004 (2002).
Mignone et al. UTRdb and UTRsite: a collection of sequences and regulatory motifs of the untranslated regions of eukaryotic mRNAs. Nucleic Acids Res 33(Database issue):D141-D146 (2005).
Mikhailov et al. Substrate Properties of C'-Methylnucleoside and C'-Methyl-2'- deoxynucleoside 5'-Triphosphates in RNA and DNA Synthesis Reactions Catalysed by RNA and DNA Polymerases Nucleosides & Nucleotides 10(1-3):339-343 (1991).
Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).
Mishra et al. Improved leishmanicidal effect of phosphorotioate antisense oligonucleotides by LDL-mediated delivery. Biochem Biophys Acta 1264:229-237 (1995).
Mulligan et al. Expression of a bacterial gene in mammalian cells. Science 209:1422-1427 (1980).
Myers et al. Reverse transcription and DNA amplification by a Thermus thermophilus DNA polymerase. Biochemistry 30:7661-7666 (1991).
Nawrot et al. A novel class of DNA analogs bearing 5'-C-phosphonothymidine units: synthesis and physicochemical and biochemical properties. Oligonucleotides16(1):68-82 (2006).
Nelson et al. N3'-->P5' Oligodeoxyribonucleotide Phosphoramidates: A New Method of Synthesis Based on a Phosphoramidite Amine-Exchange Reaction. J Org Chem 62:7278-7287 (1997).
Nelson et al. Simultaneous detection of multiple nucleic acid targets in a homogeneous format. Biochemistry. Jun. 25, 1996;35(25):8429-38.
Nielsen, et al. Sequence-selective recognition of DNA by strand displacement with a thymine-substituted polyamide. Science. 254: 1497-1500 (1991).
Nordstrom et al. Characterization of bacteriophage T7 DNA polymerase purified to homogeneity by antithioredoxin immunoadsorbent chromatography. J Biol Chem 256:3112-3117 (1981).
Oberhauser et al. Effective incorporation of 2'-O-methyl-oligoribonucleotides into liposomes and enhanced cell association through modification with thiocholesterol. Nucl. Acids Res. 20:533-538 (1992).
Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).
Orum et al. Locked nucleic acids: a promising molecular family for gene-function analysis and antisense drug development. Curr Opinion Mol Ther 3:239-243 (2001).
Papanikolaou et al. Lipid production by Yarrowia lipolytica growing on industrial glycerol in a single-stage continuous culture. Bioresour Technol 82(1):43-9 (2002).
Parel et al. Triple-helix formation in the antiparallel binding motif of oligodeoxynucleotides containing N(9)- and N(7)-2-aminopurine deoxynucleosides. Nucleic Acids Res. 29(11):2260-2267 (2001).
Paulous et al. Comparison of the capacity of different viral internal ribosome entry segments to direct translation initiation in poly(A)-dependent reticulocyte lysates. Nucleic Acids Res. 31(2):722-733 (2003).
PCT/US2016/067353 International Preliminary Report on Patentability dated Jun. 28, 2018.
PCT/US2016/067353 International Search Report and Written Opinion dated May 5, 2017.
Peyrottes et al. Oligodeoxynucleoside phosphoramidates (P-NH2): synthesis and thermal stability of duplexes with DNA and RNA targets. Nucleic Acids Res 24:1841-1848 (1996).
Saha et al. 5'-Methyl-DNA-A New Oligonucleotide Analog: Synthesis and Biochemical Properties J Org Chem 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi. Chapter 15: Heterocyclic Base Modifications In Nucleic Acids And Their Applications In Antisense Oligonucleotides. Antisense Research and Applications, Crookeand Lebleu Eds., CRC Press (pp. 273-288) (1993).
Sauer. Site-specific recombination: developments and applications. Curr Opin Biotechnol 5(5):521-527 (1994).
Schultz et al. Oligo-2'-fluoro-2'-deoxynucleotide N3'-->P5' phosphoramidates: synthesis and properties. Nucleic Acids Res 24:2966-2973 (1996).
Shaloiko et al. Effective non-viral leader for cap-independent translation in a eukaryotic cell-free system. Biotechnology and Bioengineering 88(6):730-739 (2004).
Shea et al. Synthesis, hybridization properties and antiviral activity of lipid- oligodeoxynucleotide conjugates. Nucl. Acids Res 18:3777-3783 (1990).
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Southern et al. Transformation of mammalian cells to antibiotic resistance with a bacterial gene under control of the SV40 early region promoter. J Mol Appl Genet 1:327-341 (1982).
Srivastava et al. Five- and six-membered conformationally locked 2',4'-carbocyclic ribo-thymidines: synthesis, structure, and biochemical studies. J Am Chem Soc 129(26):8362-8379 (2007).
Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).
Sugden et al. A vector that replicates as a plasmid and can be efficiently selected in B-lymphoblasts transformed by Epstein-Barr virus. Mol. Cell. Biol. 5:410-413 (1985).
Svinarchuk et al. Inhibition of HIV proliferation in MT-4 cells by antisense oligonucleotide conjugated to lipophilic groups. Biochimie 75:49-54 (1993).
Takagi et al. Characterization of DNA polymerase from *Pyrococcus* sp. strain KOD1 and its application to PCR. Appl Environ Microbiol 63(11):4504-4510 (1997).
Tuerk. Systematic evolution of ligands by exponential enrichment: RNA ligands to bacteriophage T4 DNA polymerase. Science 249:505-510 (1990).
Verma. The reverse transcriptase. Biochim Biophys Acta. 473:1-38 (1977).
Vrudhula et al. Isozyme-specific enzyme inhibitors. 13. S-[5'(R)-[(N-triphosphoamino)methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).
Wang et al. Biophysical and biochemical properties of oligodeoxynucleotides containing 4'-C- and 5'-C-substituted thymidines. Bioorg Med Chem Lett 9:885-890 (1999).
Wang et al. Synthesis of Azole Nucleoside 5'-Monophosphate Mimics (P1Ms) and Their Inhibitory Properties of IMP Dehydrogenases. Nucleosides Nucleotides & Nucleic Acids 23(1 & 2):317-337 (2004).
Wolff et al. Direct gene transfer into mouse muscle in vivo. Science 247:1465-1468 (1990).
Wu et al. Functionalization of the sugar moiety of oligoribonucleotides on solid support. Bioconjugate Chem 10:921-924 (1999).
Wu et al. Reverse transcriptase. CRC Crit Rev Biochem 3:289-347 (1975).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).

(56) References Cited

OTHER PUBLICATIONS

Zhou et al. Fine tuning of electrostatics around the internucleotidic phosphate through incorporation of modified 2',4'-carbocyclic-LNAs and -ENAs leads to significant modulation of antisense properties. J Org Chem 74:118-134 (2009).
Zon. Chapter 8: Oligonucleotide Phosphorothioates in Protocols for Oligonucleotides and Analogs, Synthesis and Properties. Humana Press (pp. 165-190) (1993).
Adhikary et al. Adaptive Mutations Alter Antibody Structure and Dynamics During Affinity Maturation. Biochemistry 54(11):2085-93 (2015).
Ambrogelly et al. Pyrrolysine is not hardwired fro cotranslational insertion at UAG condons. PNAS 104(9):3141-3146 (2007).
Amiri et al. Deep origin of plastid/parasite ATP/ADP translocases. J. Mol. Evol. 56:137-150 (2003).
Ast et al. Diatom plastids depend on nucleotide import from the cytosol. PNAS USA 106:3621-3626 (2009).
Berger et al. Stability and selectivity of unnatural DNA with five-membered-ring nucleobase analogues. J Am Chem Soc 124(7):1222-6 (2002).
Berger et al. Stable and selective hybridization of oligonucleotides with unnatural hydrophobic bases. Angew Chem Int Ed Engl 39:2940-2942 (2000).
Berger et al. Universal bases for hybridization, replication and chain termination. Nucleic Acids Res 28(15):2911-2914 (2000).
Betz et al. KlenTaq polymerase replicates unnatural base pairs by inducing a Watson-Crick geometry. Nat Chem Biol 8:612-614 (2012).
Chatterjee et al. A Versatile Platform for Single- and Multiple-Unnatural Amino Acid Mutagenesis in *Escherichia coli*. Biochemistry 52(10):1828-1837 (2013).
Chen et al. The expanding world of DNA and RNA. Curr Opin Chem Biol 34:80-87 (2016).
Co-pending U.S. Appl. No. 16/518,715, filed Jul. 22, 2019.
Co-pending U.S. Appl. No. 16/535,992, filed Aug. 8, 2019.
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al. Progress Toward a Semi-Synthetic Organism with an Unrestricted Expanded Genetic Alphabet. J Am Chem Soc. 140:16115-16123 (2018).
Dupradeau et al. Differential solvation and tautomer stability of a model base pair within the minor and major grooves of DNA. J Am Chem Soc 127(44):15612-7 (2005).
Fa et al. Expanding the substrate repertoire of a DNA polymerase by directed evolution. J Am Chem Soc 126(6):1748-54 (2004).
Fan et al. Rationally evolving tRNAPyl for efficient incorporation of noncanonical amino acids. Nucleic Acids Res 43(22):e156 (2015).
Feldman et al. A Tool for the Import of Natural and Unnatural Nucleoside Triphosphates into Bacteria. J Am Chem Soc 140(4):1447-1454 (2018).
Feldman et al. Chemical Stabilization of Unnatural Nucleotide Triphosphates for the in Vivo Expansion of the Genetic Alphabet. J Am Chem Soc 139(6):2464-2467 (2017).
Feldman et al. In Vivo Structure-Activity Relationships and Optimization of an Unnatural Base Pair for Replication in a Semi-Synthetic Organism. J Am Chem Soc 139:11427-11433 (2017).
Feldman et al. Optimization of Replication, Transcription, and Translation in a Semi-Synthetic Organism. J Am Chem Soc 141:10644-10653 (2019).
Feldman. Expansion of the Genetic Alphabet: A Chemist's Approach to Synthetic Biology. Acc Chem Res 51(2):394-403 (2018).
Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbiol. 60:1534-1545 (2006).
Hancock et al. Expanding the Genetic Code of Yeast for Incorporation of Diverse Unnatural Amino Acids via a Pyrrolysyl-tRNA Synthetase/tRNA Pair. JACS 132:14819-14824 (2010).

Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacteriol. 150:662-670 (1982).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125(32):9638-9646 (2003).
Henry et al. Efforts to expand the genetic alphabet: identification of a replicable unnatural DNA self-pair. J Am Chem Soc 126(22):6923-31 (2004).
Hirao et al., Unnatural base pair systems toward the expansion of the genetic alphabet in the central dogma.Proceedings of the Japan Academy, Series B, Phys Biol Sci. 88:345-367 (2012).
Horn et al. Bacterial endosymbionts of free-living amoebae. J. Eukaryot. Microbiol. 5:509-514 (2004).
Hwang et al. Polymerase recognition and stability of fluoro-substituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and solvation. Nucleic Acids Res 37(14):4757-4763 (2009).
Hwang et al. Unnatural substrate repertoire of A, B, and X family DNA polymerases. J Am Chem Soc 130(44):14872-14882 (2008).
Kim et al. Stability and polymerase recognition of pyridine nucleobase analogues: role of minor-groove H-bond acceptors. Angew Chem Int Ed Engl 45(46):7809-12 (2006).
Lavergne et al. Expanding the scope of replicable unnatural DNA: Stepwise optimization of a predominantly hydrophobic base pair. JACS 135:5408-5419 (2013).
Lavergne et al. FRET Characterization of Complex Conformational Changes in a Large 16S Ribosomal RNA Fragment Site-Specifically Labeled Using Unnatural Base Pairs. ACS Chem Biol 11(5):1347-53 (2016).
Lavergne et al. Major groove substituents and polymerase recognition of a class of predominantly hydrophobic unnatural base pairs. Chem. Eur. J. 18:1231-1239 (2012).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127(36):12470-1 (2005).
Ledbetter et al. Editorial overview: Expanding the genetic alphabet and code. Curr Opin Chem Biol 46:A1-A2 (2018).
Ledbetter et al. Reprograming the Replisome of a Semisynthetic Organism for the Expansion of the Genetic Alphabet. J Am Chem Soc. 140:758-765 (2018).
Ledbetter et al. Site-Specific Labeling of DNA via PCR with an Expanded Genetic Alphabet. Methods Mol Biol 1973:193-212 (2019).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).

(56) References Cited

OTHER PUBLICATIONS

Li et al. Site-Specifically Arraying Small Molecules or Proteins on DNA Using An Expanded Genetic Alphabet. Chem Eur J 19:14205-14209 (2013).
Malyshev et al. Efficient and sequence-independent replication of DNA containing a third base pair establishes a functional six-letter genetic alphabet. PNAS USA 109:12005-12010 (2012).
Malyshev et al. PCR with an Expanded Genetic Alphabet. JACS 131(41):14620-14621 (2009).
Malyshev et al. Solution structure, mechanism of replication, and optimization of an unnatural base pair. Chem Eur J 16:12650-12659 (2010).
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129(17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128(19):6369-75 (2006).
Matsuda et al. The effect of minor-groove hydrogen-bond acceptors and donors on the stability and replication of four unnatural base pairs. J Am Chem Soc 125(20):6134-9 (2003).
McMinn et al. Efforts toward Expansion of the Genetic Alphabet: DNA Polymerase Recognition of a Highly Stable, Self-Pairing Hydrophobic Base. J. Am. Chem. Soc. 121:11585-11586 (1999).
Meggers et al. A Novel Copper-Mediated DNA Base Pair. J. Am. Chem. Soc. 122:10714-10715 (2000).
Miroux et al. Over-production of proteins in *Escherichia coli*: mutant hosts that allow synthesis of some membrane proteins and globular proteins at high levels. J Mol Biol 260:289-298 (1996).
Morris et al. Synthetic Biology Parts for the Storage of Increased Genetic Information in Cells. ACS Synth Biol 6(10):1834-1840 (2017).
Nguyen et al. Genetic Encoding and Labeling of Aliphatic Azides and Alkynes in Recombinant Proteins via a Pyrrolysyl-tRNA Synthetase/tRNACUA Pair and Click Chemistry. JACS 131:8720-8721 (2009).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
PCT/US2018/041503 International Search Report and Written Opinion dated Nov. 7, 2018.
PCT/US2018/045257 International Search Report and Written Opinion dated Nov. 21, 2018.
Romesberg et al. Development of a universal nucleobase and modified nucleobases for expanding the genetic code. Curr Prot Nucleic Acid Chem Chapter 1:Unit 1.5 (2002).
Schmied et al. Efficient Multisite Unnatural Amino Acid Incorporation in Mammalian Cells via Optimized Pyrrolysyl tRNA Synthetase/tRNA Expression and Engineered eRF1. JACS 136:15577-15583 (2014).
Seo et al. Major groove derivatization of an unnatural base pair. Chembiochem 10(14):2394-2400 (2009).
Seo et al. Optimization of an unnatural base pair toward natural-like replication. J Am Chem Soc 131:3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JACS 131(14):5046-5047 (2009).
Tae et al. Efforts toward expansion of the genetic alphabet: replication of DNA with three base pairs. J. Am. Chem. Soc. 123:7439-7440 (2001).
Vanbrunt et al. Genetically Encoded Azide Containing Amino Acid in Mammalian Cells Enables Site-Specific Antibody-Drug Conjugates Using Click Cycloaddition Chemistry. Bioconjug Chem. 26(11):2249-60 (2015).
Verma. Retroviral vectors for gene transfer. In: Microbiology (Leive L et al., eds., Ann. Soc. Microbiol) American Society of Microbiology, Washington, DC, p. 229-232 (1985).
Wandry et al. Probing unnatural amino acid integration into enhanced green fluorescent protein by genetic code expansion with a high-throughput screening platform. J Biol Eng. 10:11 (2016).
Winkler et al. Non-mitochondrial ATP transport. Trends Biochem. Sci. 24:64-68 (1999).
Winkler. Rickettsial permeability: an ADP-ATP transport system. J Biol Chem 251:389-396 (1976).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Synthesis of Site-Specific Radiolabeled Antibodies for Radioimmunotherapy via Genetic Code Expansion. Bioconjugate Chem. 27:2460-2468 (2016).
Xia et al. Directed evolution of novel polymerase activities: mutation of a DNA polymerase into an efficient RNA polymerase. PNAS USA 99(10):6597-602 (2002).
Yu et al. Polymerase recognition of unnatural base pairs. Angew Chem Int Ed Engl 41(20):3841-4 (2002).
Zhang et al. A semisynthetic organism engineered for the stable expansion of the genetic alphabet. PNAS USA 114(6):1317-1322 (2017).
Zhang et al. A Semi-Synthetic Organism that Stores and Retrieves Increased Genetic Information. Nature 551(7682):644-647 (2017).
Zhang et al. Semisynthetic Organisms with Expanded Genetic Codes. Biochemistry 57:2177-2178 (2018).

\* cited by examiner

Target

TK1    GUAUGUUGUGUGGAAYUGUGAG

Guide RNA hEGFP    GACCAGGAUGGGCACCACCC
TK1-A    GUAUGUUGUGUGGAAAUGUGAG
TruTK1-A    GUUGUGUGGAAAUGUGAG
TruTK1-A/Δ  − { GUUGUGUGGAAAUGUGAG / UGUUGUGUGGAAUGUGAG }

FIG. 6

| Name | Sequence/sgRNA | Mutation (Major, minor) | CTRL | N=A | N=G | N=C | N=U |
|---|---|---|---|---|---|---|---|
| hGFP12-YTG sgRNA | CCAGGATGGGCACCAYCCGG CCAGGATGGGCACCANCC | G, A, Δ | 91 ± 0 | 73 ± 7 | 93 ± 6 | 95 ± 12 | 79 ± 7 |
| hGFP13-GTY sgRNA | CCAGGATGGGCTACCACCCGG CCAGGATGGGCTACCANCC | A, C | 72 ± 2 | 101 ± 4 | 99 ± 15 | 28 ± 3 | 60 ± 8 |
| hGFP16-YTG sgRNA | CCAYGATGGGCACCACCCCGG CCANGATGGGCACCACCCC | A, T | 27 ± 2 | 28 ± 2 | 25 ± 1 | 21 ± 3 | 92 ± 4 |
| hGFP12-XTG sgRNA | CCAGGATGGGCACCAXCCGG CCAGGATGGGCACCANCC | C, A | 84 ± 0 | 88 ± 0 | 89 ± 2 | 92 ± 3 | 96 ± 1 |
| hGFP13-GTX sgRNA | CCAGGATGGGCXACCACCCGG CCAGGATGGGCNACCACCC | T, G | 35 ± 5 | 89 ± 1 | 99 ± 11 | 54 ± 5 | 92 ± 13 |
| hGFP16-XTG sgRNA | CCAXGATGGGCACCACCCCGG CCANGATGGGCACCACCC | T, G | 19 ± 5 | 23 ± 4 | 29 ± 3 | 16 ± 3 | 65 ± 3 |

| | |
|---|---|
| GFP151-GXG | TCACACAATGTAGXGATCACGG |
| hGFP13-GTX | ACCAGGATGGGYACCACCCCGG |
| GFP151-GXC | TCACACAATGTAGXCATCACGG |
| GFP12-YTG | ACCAGGATGGGCACCAYCCCGG |
| hGFP16-YTG | ACCAYGATGGGCACCACCCCGG |
| GFP151-XAG | TCACACAATGTAXAGATCACGG |
| hGFP12-XTG | ACCAGGATGGGCACCAXCCCGG |
| TK1-NC-AXT | TGTTGTGTGGAAXTGTGAGCGG |
| GFP66-YGC | TTGTCACTACTCTGACCYGCGG |
| GFP66-XAG | TTGTCACTACTCTGACCXAGGG |
| GFP151-CXC | TCACACAATGTACXCATCACGG |
| hGFP16-YTG | ACCAXGATGGGCACCACCCCGG |
| GFP151-TXG | TCACACAATGTATXGATCACGG |
| GFP151-TYA | TCACACAATGTATYAATCACGG |
| hGFP13-GYA | ACCAGGATGGGXACCACCCCGG |
| D8-NC-TXT | ATTCACAATACTXTCTTTAAGG |

FIG. 7

SEQUENCE LISTING

<160> NUMBER OF SEQ ID NOS: 100

<210> SEQ ID NO 1
<211> LENGTH: 6363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | |
|---|---|---|---|---|---|
| ctctgcttgg | acggacagga | tgtatgctgt | ggctttttta | aggataacta | ccttgggggc | 60 |
| cttttcattg | ttttccaact | ccgggatctg | gtcacgcagg | gcaaaaaagc | tccgttttag | 120 |
| ctcgttcctc | ctctggcgct | ccaagacgtt | gtgtgttcgc | ctcttgacat | tctcctcggt | 180 |
| gtccgagggc | cctgtgtgaa | attgttatcc | gctcacaatt | ccacacagac | gtcgttgaca | 240 |
| attaatcatc | ggcatagtat | atcggcatag | tataatacga | caaggtgagg | aactaaacca | 300 |
| tggccaagtt | gaccagtgcc | gttccggtgc | tcaccgcgcg | cgacgtcgcc | ggagcggtcg | 360 |
| agttctggac | cgaccggctc | gggttctccc | gggacttcgt | ggaggacgac | ttcgccggtg | 420 |
| tggtccggga | cgacgtgacc | ctgttcatca | gcgcggtcca | ggaccaggtg | gtgccggaca | 480 |
| acaccctggc | ctgggtgtgg | gtgcgcggcc | tggacgagct | gtacgccgag | tggtcggagg | 540 |
| tcgtgtccac | gaacttccgg | gacgcctccg | gccggccat | gaccgagatc | ggcgagcagc | 600 |
| cgtgggggcg | ggagttcgcc | ctgcgcgacc | cggccggcaa | ctgcgtgcac | ttcgtggccg | 660 |
| aggagcagga | ctgagagctc | gcttggactc | ctgttgatag | atccagtaat | gacctcagaa | 720 |
| ctccatctgg | atttgttcag | aacgctcggt | tgccgccggg | cgttttttat | tggtgagaat | 780 |
| ccaagcacta | gtaacaactt | atatcgtatg | gggctgactt | caggtgctac | atttgaagag | 840 |
| ataaattgca | ctgaaatcta | gtaatatttt | atctgattaa | taagatgatc | ttcttgagat | 900 |
| cgttttggtc | tgcgcgtaat | ctcttgctct | gaaaacgaaa | aaaccgcctt | gcagggcggt | 960 |
| ttttcgaagg | ttctctgagc | taccaactct | ttgaaccgag | gtaactggct | tggaggagcg | 1020 |
| cagtcaccaa | aacttgtcct | ttcagtttag | ccttaaccgg | cgcatgactt | caagactaac | 1080 |
| tcctctaaat | caattaccag | tggctgctgc | cagtggtgct | tttgcatgtc | tttccgggtt | 1140 |
| ggactcaaga | cgatagttac | cggataaggc | gcagcggtcg | gactgaacgg | ggggttcgtg | 1200 |
| catacagtcc | agcttggagc | gaactgccta | cccggaactg | agtgtcaggc | gtggaatgag | 1260 |
| acaaacgcgg | ccataacagc | ggaatgacac | cggtaaaccg | aaaggcagga | acaggagagc | 1320 |
| gcacgaggga | gccgccaggg | ggaaacgcct | ggtatcttta | tagtcctgtc | gggtttcgcc | 1380 |
| accactgatt | tgagcgtcag | atttcgtgat | gcttgtcagg | ggggcggagc | ctatggaaaa | 1440 |
| acggctttgc | cgcggccctc | tcacttcct | gttaagtatc | ttcctggcat | cttccaggaa | 1500 |
| atctccgccc | cgttcgtaag | ccatttccgc | tcgccgcagt | cgaacgaccg | agcgtagcga | 1560 |
| gtcagtgagc | gaggaagcgg | aatatatccc | ctaggtctag | ggcggcggat | ttgtcctact | 1620 |

```
caggagagcg ttcaccgaca aacaacagat aaaacgaaag gcccagtctt tcgactgagc   1680
ctttcgtttt atttgatgcc tctagattac accttcctct tcttcttggg gtcagccctg   1740
ctgtctccac cgagctgaga gaggtcgatt cttgtttcat agagcccgt aattgactga    1800 tgaatcagtg tggcgtccag gacctccttt gtagaggtgt accgctttct gtctatggtg   1860
gtgtcgaagt acttgaaggc tgcaggcgcg cccaagttgg tcagagtaaa caagtggata   1920
atgttttctg cctgctccct gatgggctta tccctgtgct tattgtaagc agaaagcacc   1980
ttatcgaggt tagcgtcggc gaggatcact cttttggaga attcgcttat ttgctcgatg   2040
atctcatcaa ggtagtgttt gtgttgttcc acgaacagct gcttctgctc attatcttcg   2100 ggagacccctt tgagcttttc atagtggctg ccagataca agaaattaac gtatttagag    2160
ggcagtgcca gctcgttacc tttctgcagc tcgcccgcac tagcgagcat tcgtttccgg   2220
ccgttttcaa gctcaaagag agagtacttg ggaagcttaa tgatgaggtc ttttttgacc   2280
tctttatatc ctttcgcctc gagaaagtcg atggggtttt tttcgaagct tgatcgctcc   2340
atgattgtga tgcccagcag ttccttgacg cttttgagtt ttttagactt cccttctcc    2400 actttggcca caaccagtac actgtaagcg actgtaggag aatcgaatcc gccgtatttc   2460
ttggggtccc aatcttttt gcgtgcgatc agcttgtcgc tgttccttt cggaggata     2520 cttttccttgg agaagcctcc ggtctgtact tcggtcttt taacgatgtt cacctgcggc   2580
atggacagga ccttccggac tgtcgcgaaa tccctaccct tgtcccacac gatttctcct   2640
gtttctccgt tgtttcgat aagtggtcgc ttccgaatct ctccattggc cagtgtaatc    2700
tcggtcttga aaaaattcat aatattgctg taaaagaagt acttagcggt ggccttgcct   2760
atttcctgct cagactttgc gatcattttc ctaacatcgt acactttata gtctccgtaa   2820
acaaattcag attcaagctt gggatatttt ttgataagtg cagtgcctac cactgcattc   2880
aggtaggcat catgcgcatg gtggtaattg ttgatctctc tcaccttata aaactgaaag   2940 tccttttctga aatctgagac cagcttagac ttcagagtaa taactttcac ctctcgaatc   3000
agtttgtcat tttcatcgta cttggtgttc atgcgtgaat cgagaatttg ggccacgtgc   3060
ttggtgatct ggcgtgtctc aacaagctgc cttttgatga agccggcttt atccaactca   3120
gacaggccac ctcgttcagc cttagtcaga ttatcgaact tccgttgtgt gatcagtttg   3180
gcgttcagca gctgccgcca ataatttttc attttcttga caacttcttc tgaggggacg   3240
ttatcactct tccctctatt tttatcggat cttgtcaaca ctttattatc aatagaatca   3300
tctttgagaa aagactgggg cacgatatga tccacgtcgt agtcggagag ccgattgatg   3360
tccagttcct gatccacgta catgtccctg ccgttctgca ggtagtacag gtagagcttc   3420
tcattctgaa gctgggtgtt ttcaactggg tgttccttaa ggatttggga ccccagttct   3480
tttataccct cttcaatcct cttcatcctt tccctactgt tcttctgtcc cttctgggta   3540
gtttggttct ctcgggccat ctcgataacg atattctcgg gcttatgcct tcccattact   3600
ttgacgagtt catccacgac cttaacggtc tgcagtattc cctttttgat agctgggcta   3660
cctgcaagat tagcgatgtg ctcgtgaaga ctgtccccct ggccagaaac ttgtgctttc   3720
tggatgtcct cctaaaggt gagagagtca tcatggatca actgcatgaa gttccggttg    3780
gcaaatccat cggacttaag aaaatccagg attgtctttc cactctgctt gtctcggatc   3840
ccattgatca gttttcttga cagccgcccc catcctgtat atcggcgcct cttgagctgt   3900
ttcatgactt tgtcgtcgaa gagatgagcg taagttttca agcgttcttc aatcatctcc   3960
```

```
ctatcttcaa acaacgtaag ggtgaggaca atgtcctcaa gaatgtcctc gttctcctca      4020
ttgtccagga agtccttgtc tttaatgatt ttcaggagat cgtgatacgt tcccagggat      4080
gcgttgaagc gatcctccac tccgctgatt tcaacagagt cgaaacattc aatcttttg       4140 aaatagtctt ctttgagctg tttcacggta actttccggt tcgtcttgaa gaggaggtcc      4200
acgatagctt tcttctgctc tccagacagg aatgctggct ttctcatccc ttctgtgacg      4260
tatttgacct tggtgagctc gttataaact gtgaagtact cgtacagcag agagtgttta      4320
ggaagcacct tttcgttagg cagatttta tcaaagttag tcatcctttc gatgaaggac       4380
tgggcagagg ccccttatc cacgacttcc tcgaagttcc agggagtgat ggtctcttct       4440
gatttgcgag tcatccacgc gaatctggaa tttccccggg cgaggggcc tacatagtag       4500 ggtatccgaa atgtgaggat tttctcaatc ttttccctgt tatctttcaa aaggggtag      4560 aaatcctctt gccgcctgag gatagcgtgc agttcgccca ggtgaatctg gtggggatg      4620 cttccattgt cgaaagtgcg ctgtttgcgc aacagatctt ctctgttaag ctttaccagc      4680
agctcctcgg tgccgtccat ttttccaag atgggcttaa taatttgta aaattcctcc       4740 tggcttgctc cgccgtcaat gtatccggcg tagccatttt tagactgatc gaagaaaatt     4800
tccttgtact tctcaggcag ttgctgtctg acaagggcct tcagcaaagt caagtcttgg     4860
tggtgctcat catagcgctt gatcatacta gcgctcagcg gagctttggt gatctccgtg    4920
ttcactcgca gaatatcact cagcagaatg gcgtctgaca ggttctttgc cgccaaaaaa    4980
aggtctgcgt actggtcgcc gatctgggcc agcagattgt cgagatcatc atcgtaggtg    5040
tctttgctca gttgaagctt ggcatcttcg gccaggtcga agttagattt aaagttgggg    5100
gtcagcccga gtgacagggc gataagatta ccaaacaggc cgttcttctt ctccccaggg    5160
agctgtgcga tgaggttttc gagccgccgg gatttggaca gcctagcgct caggattgct    5220
ttggcgtcaa ctccggatgc gttgatcggg ttctcttcga aaagctgatt gtaagtctga    5280
accagttgga taaagagttt gtcgacatcg ctgttgtctg ggttcaggtc cccctcgatg    5340
aggaagtgtc cccgaaattt gatcatatgc gccagcgcga gatagatcaa ccgcaagtca    5400
gccttatcag tactgtctac aagcttcttc ctcagatgat atatggttgg gtacttttca    5460
tggtacgcca cctcgtccac gatattgcca aagattgggt ggcgctcgtg cttttatcc     5520 tcctccacca aaaaggactc ctccagccta tggaagaaag agtcatccac cttagccatc    5580
tcattactaa agatcctctg caggtagcag atccgattct ttctgcgggt atatctgcgc    5640
cgtgctgttc ttttgagccg cgtggcttcg gccgtctccc cggagtcgaa caggagggcg    5700
ccaatgaggt tcttctttat gctgtggcga tcggtattgc ccagaacttt gaattttttg    5760
ctcggcacct tgtactcgtc cgtaatgacg gcccagccga cgctgtttgt gccgatatcg    5820
agcccaatgg agtacttctt gtccatggta cctttctcct ctttaatgaa ttctgtgtga    5880
aattgttatc cgctcacaat tgaatctatc ataattgtga gcgctcacaa ttgtaaaggt    5940
tagatctaaa actagtggca gcggctaact aagcggcctg ctgactttct cgccgatcaa    6000
aaggcatttt gctattaagg gattgacgag gcgtatctg cgcagtaaga tgcgccccgc     6060
attgtatgtt gtgtggaaat gtgaggtttt agagctagaa atagcaagtt aaaataaggc    6120
tagtccgtta tcaacttgaa aaagtggcac cgagtcggtg ctttttttaa ttcgaaaagc    6180
ctgctcaacg agcaggcttt tttggtcgac agttcatagg tgattgctca ggacatttct    6240
```

| | |
|---|---|
| gttagaagga atcgttttcc ttacttttcc ttacgcacaa gagttccgta gctgttcaag | 6300 |
| tttgtgtttc aactgttctc gtcgtttccg caacaagtcc tcttcagaaa tgagcttttg | 6360 |
| ctc | 6363 |

<210> SEQ ID NO 2
<211> LENGTH: 6359
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

| | |
|---|---|
| ctctgcttgg acggacagga tgtatgctgt ggcttttta aggataacta ccttgggggc | 60 |
| cttttcattg ttttccaact ccgggatctg gtcacgcagg gcaaaaaagc tccgttttag | 120 |
| ctcgttcctc ctctggcgct ccaagacgtt gtgtgttcgc ctcttgacat tctcctcggt | 180 |
| gtccgagggc cctgtgtgaa attgttatcc gctcacaatt ccacacagac gtcgttgaca | 240 |
| attaatcatc ggcatagtat atcggctag tataatacga caaggtgagg aactaaacca | 300 |
| tggccaagtt gaccagtgcc gttccggtgc tcaccgcgcg cgacgtcgcc ggagcggtcg | 360 |
| agttctggac cgaccggctc gggttctccc gggacttcgt ggaggacgac ttcgccggtg | 420 |
| tggtccggga cgacgtgacc ctgttcatca gcgcggtcca ggaccaggtg gtgccggaca | 480 |
| acaccctggc ctgggtgtgg gtgcgcggcc tggacgagct gtacgccgag tggtcggagg | 540 |
| tcgtgtccac gaacttccgg gacgcctccg ggccggccat gaccgagatc ggcgagcagc | 600 |
| cgtggggggcg ggagttcgcc ctgcgcgacc cggccggcaa ctgcgtgcac ttcgtggccg | 660 |
| aggagcagga ctgagagctc gcttggactc ctgttgatag atccagtaat gacctcagaa | 720 |
| ctccatctgg atttgttcag aacgctcggt tgccgccggg cgttttttat tggtgagaat | 780 |
| ccaagcacta gtaacaactt atatcgtatg gggctgactt caggtgctac atttgaagag | 840 |
| ataaattgca ctgaaatcta gtaatatttt atctgattaa taagatgatc ttcttgagat | 900 |
| cgttttggtc tgcgcgtaat ctcttgctct gaaaacgaaa aaaccgcctt gcagggcggt | 960 |
| ttttcgaagg ttctctgagc taccaactct ttgaaccgag gtaactggct tggaggagcg | 1020 |
| cagtcaccaa aacttgtcct ttcagtttag ccttaaccgg cgcatgactt caagactaac | 1080 |
| tcctctaaat caattaccag tggctgctgc cagtggtgct tttgcatgtc tttccgggtt | 1140 |
| ggactcaaga cgatagttac cggataaggc gcagcggtcg gactgaacgg ggggttcgtg | 1200 |
| catacagtcc agcttggagc gaactgccta cccggaactg agtgtcaggc gtggaatgag | 1260 |
| acaaacgcgg ccataacagc ggaatgacac cggtaaaccg aaaggcagga acaggagagc | 1320 |
| gcacgaggga gccgccaggg ggaaacgcct ggtatcttta tagtcctgtc gggtttcgcc | 1380 |
| accactgatt tgagcgtcag atttcgtgat gcttgtcagg ggggcggagc ctatggaaaa | 1440 |
| acggctttgc cgcggccctc tcacttccct gttaagtatc ttcctggcat cttccaggaa | 1500 |
| atctccgccc cgttcgtaag ccatttccgc tcgccgcagt cgaacgaccg agcgtagcga | 1560 |
| gtcagtgagc gaggaagcgg aatatatccc ctaggtctag gcggcggat ttgtcctact | 1620 |
| caggagagcg ttcaccgaca acaacagat aaaacgaaag gcccagtctt tcgactgagc | 1680 |
| ctttcgtttt atttgatgcc tctagattac accttcctct tcttcttggg gtcagccctg | 1740 |
| ctgtctccac cgagctgaga gaggtcgatt cttgttcat agagcccgt aattgactga | 1800 |
| tgaatcagtg tggcgtccag gacctccttt gtagaggtgt accgctttct gtctatggtg | 1860 |

```
gtgtcgaagt acttgaaggc tgcaggcgcg cccaagttgg tcagagtaaa caagtggata    1920
atgttttctg cctgctccct gatgggctta tccctgtgct tattgtaagc agaaagcacc    1980
ttatcgaggt tagcgtcggc gaggatcact cttttggaga attcgcttat ttgctcgatg    2040
atctcatcaa ggtagtgttt gtgttgttcc acgaacagct gcttctgctc attatcttcg    2100 ggagacccett tgagcttttc atagtggctg ccagataca agaaattaac gtatttagag    2160
ggcagtgcca gctcgttacc tttctgcagc tcgcccgcac tagcgagcat tcgtttccgg    2220
ccgttttcaa gctcaaagag agagtacttg ggaagcttaa tgatgaggtc ttttttgacc    2280 tcttatatc ctttcgcctc gagaaagtcg atggggtttt tttcgaagct tgatcgctcc    2340
atgattgtga tgcccagcag ttccttgacg cttttgagtt ttttagactt ccctttctcc    2400
acttggccca caaccagtac actgtaagcg actgtaggag aatcgaatcc gccgtatttc    2460
ttggggtccc aatcttttt gcgtgcgatc agcttgtcgc tgttccttt cggaggata     2520 cttccttgg agaagcctcc ggtctgtact tcggtctttt taacgatgtt cacctgcggc    2580
atggacagga ccttccggac tgtcgcgaaa tccctaccct tgtcccacac gatttctcct    2640
gtttctccgt tgtttcgat aagtggtcgc ttccgaatct ctccattggc cagtgtaatc    2700
tcggtcttga aaaaattcat aatattgctg taaaagaagt acttagcggt ggccttgcct    2760
atttcctgct cagactttgc gatcattttc ctaacatcgt acactttata gtctccgtaa    2820
acaaattcag attcaagctt gggatatttt ttgataagtg cagtgcctac cactgcattc    2880
aggtaggcat catgcgcatg gtggtaattg ttgatctctc tcaccttata aaactgaaag    2940
tcctttctga aatctgagac cagcttagac ttcagagtaa taactttcac ctctcgaatc    3000 agttgtcat tttcatcgta cttggtgttc atgcgtgaat cgagaatttg gccacgtgc    3060 ttggtgatct ggcgtgtctc aacaagctgc cttttgatga agccggcttt atccaactca    3120
gacaggccac ctcgttcagc cttagtcaga ttatcgaact tccgttgtgt gatcagtttg    3180
gcgttcagca gctgccgcca ataattttc attttcttga caacttcttc tgaggggacg    3240
ttatcactct tccctctatt tttatcggat cttgtcaaca ctttattatc aatagaatca    3300
tctttgagaa aagactgggg cacgatatga tccacgtcgt agtcggagag ccgattgatg    3360
tccagttcct gatccacgta catgtccctg ccgttctgca ggtagtacag gtagagcttc    3420
tcattctgaa gctgggtgtt tcaactggg tgttccttaa ggatttggga ccccagttct    3480 tttatccct cttcaatcct cttcatcctt tccctactgt tcttctgtcc cttctgggta    3540
gtttggttct ctcgggccat ctcgataacg atattctcgg gcttatgcct tcccattact    3600
ttgacgagtt catccacgac cttaacggtc tgcagtattc ccttttgat agctgggcta    3660 cctgcaagat tagcgatgtg ctcgtgaaga ctgtccccct ggccagaaac ttgtgctttc    3720
tggatgtcct ccttaaaggt gagagagtca tcatggatca actgcatgaa gttccggttg    3780
gcaaatccat cggacttaag aaaatccagg attgtctttc cactctgctt gtctcggatc    3840
ccattgatca gttttcttga cagccgcccc catcctgtat atcggcgcct cttgagctgt    3900
ttcatgactt tgtcgtcgaa gagatgagcg taagttttca agcgttcttc aatcatctcc    3960
ctatcttcaa acaacgtaag ggtgaggaca atgtcctcaa gaatgtcctc gttctcctca    4020
ttgtccagga agtccttgtc tttaatgatt ttcaggagat cgtgatacgt tcccagggat    4080
gcgttgaagc gatcctccac tccgctgatt tcaacagagt cgaaacattc aatctttttg    4140
aaatagtctt ctttgagctg tttcacggta actttccggt tcgtcttgaa gaggaggtcc    4200
```

```
acgatagctt tcttctgctc tccagacagg aatgctggct ttctcatccc ttctgtgacg    4260
tatttgacct tggtgagctc gttataaact gtgaagtact cgtacagcag agagtgttta    4320
ggaagcacct tttcgttagg cagattttta tcaaagttag tcatcctttc gatgaaggac    4380
tgggcagagg cccccttatc cacgacttcc tcgaagttcc agggagtgat ggtctcttct    4440
gatttgcgag tcatccacgc gaatctggaa tttccccggg cgagggggcc tacatagtag    4500
ggtatccgaa atgtgaggat tttctcaatc ttttcccctgt tatctttcaa aaaggggtag    4560
aaatcctctt gccgcctgag gatagcgtgc agttcgccca ggtgaatctg gtggggatg     4620 cttccattgt cgaaagtgcg ctgtttgcgc aacagatctt ctctgttaag ctttaccagc    4680
agctcctcgg tgccgtccat ttttccaag atgggcttaa taaatttgta aaattcctcc     4740
tggcttgctc cgccgtcaat gtatccgcg tagccattt tagactgatc gaagaaaatt      4800
tccttgtact tctcaggcag ttgctgtctg acaagggcct tcagcaaagt caagtcttgg    4860
tggtgctcat catagcgctt gatcatacta gcgctcagcg gagctttggt gatctccgtg    4920
ttcactcgca gaatatcact cagcagaatg gcgtctgaca ggttctttgc cgccaaaaaa    4980
aggtctgcgt actggtcgcc gatctgggcc agcagattgt cgagatcatc atcgtaggtg    5040
tctttgctca gttgaagctt ggcatcttcg gccaggtcga agttagattt aaagttgggg    5100
gtcagcccga gtgacagggc gataagatta ccaaacaggc cgttcttctt ctccccaggg    5160
agctgtgcga tgaggttttc gagccgccgg gatttggaca gcctagcgct caggattgct    5220
ttggcgtcaa ctccggatgc gttgatcggg ttctcttcga aaagctgatt gtaagtctga    5280
accagttgga taaagagttt gtcgacatcg ctgttgtctg ggttcaggtc cccctcgatg    5340
aggaagtgtc cccgaaattt gatcatatgc gccagcgcga gatagatcaa ccgcaagtca    5400
gccttatcag tactgtctac aagcttcttc ctcagatgat atatggttgg gtacttttca    5460
tggtacgcca cctcgtccac gatattgcca aagattgggg ggcgctcgtg cttttttatcc   5520 tcctccacca aaaaggactc ctccagccta tggaagaaag agtcatccac cttagccatc    5580
tcattactaa agatctcctg caggtagcag atccgattct ttctgcgggt atatctgcgc    5640
cgtgctgttc ttttgagccg cgtggcttcg gccgtctccc cggagtcgaa caggagggcg    5700
ccaatgaggt tcttctttat gctgtggcga tcggtattgc ccagaacttt gaattttttg    5760
ctcggcacct tgtactcgtc cgtaatgacg gccagccga cgctgtttgt gccgatatcg      5820
agcccaatgg agtacttctt gtccatggta cctttctcct ctttaatgaa ttctgtgtga    5880
aattgttatc cgctcacaat tgaatctatc ataattgtga gcgctcacaa ttgtaaaggt    5940
tagatctaaa actagtggca gcggctaact aagcggcctg ctgactttct cgccgatcaa    6000
aaggcatttt gctattaagg gattgacgag gcgtatctg cgcagtaaga tgcgccccgc     6060
attgttgtgt ggaaatgtga ggttttagag ctagaaatag caagttaaaa taaggctagt    6120
ccgttatcaa cttgaaaaag tggcaccgag tcggtgcttt ttttaattcg aaaagcctgc    6180
tcaacgagca ggctttttg gtcgacagtt cataggtgat tgctcaggac atttctgtta     6240
gaaggaatcg ttttccttac ttttccttac gcacaagagt tccgtagctg ttcaagtttg    6300
tgtttcaact gttctcgtcg tttccgcaac aagtcctctt cagaaatgag cttttgctc     6359
```

<210> SEQ ID NO 3
<211> LENGTH: 6614
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
ctctgcttgg acggacagga tgtatgctgt ggctttttta aggataacta ccttgggggc      60
cttttcattg ttttccaact ccgggatctg gtcacgcagg gcaaaaaagc tccgttttag     120
ctcgttcctc ctctggcgct ccaagacgtt gtgtgttcgc ctcttgacat tctcctcggt     180
gtccgagggc cctgtgtgaa tttgttatcc gctcacaatt ccacacagac gtcgttgaca     240
attaatcatc ggcatagtat atcggcatag tataatacga caaggtgagg aactaaacca     300
tggccaagtt gaccagtgcc gttccggtgc tcaccgcgcg cgacgtcgcc ggagcggtcg     360
agttctggac cgaccggctc gggttctccc gggacttcgt ggaggacgac ttcgccggtg     420
tggtccggga cgacgtgacc ctgttcatca gcgcggtcca ggaccaggtg gtgccggaca     480
acaccctggc ctgggtgtgg gtgcgcggcc tggacgagct gtacgccgag tggtcggagg     540
tcgtgtccac gaacttccgg gacgcctccg gccggccat gaccgagatc ggcgagcagc     600
cgtggggcg ggagttcgcc ctgcgcgacc cggccggcaa ctgcgtgcac ttcgtggccg     660
aggagcagga ctgagagctc gcttggactc ctgttgatag atccagtaat gacctcagaa     720
ctccatctgg atttgttcag aacgctcggt tgccgccggg cgttttttat tggtgagaat     780
ccaagcacta gtaacaactt atatcgtatg ggctgactt caggtgctac atttgaagag     840
ataaattgca ctgaaatcta gtaatatttt atctgattaa taagatgatc ttcttgagat     900
cgttttggtc tgcgcgtaat ctcttgctct gaaaacgaaa aaaccgcctt gcagggcggt     960
ttttcgaagg ttctctgagc taccaactct ttgaaccgag gtaactggct tggaggagcg    1020
cagtcaccaa aacttgtcct ttcagtttag ccttaaccgg cgcatgactt caagactaac    1080
tcctctaaat caattaccag tggctgctgc cagtggtgct tttgcatgtc tttccgggtt    1140
ggactcaaga cgatagttac cggataaggc gcagcggtcg gactgaacgg ggggttcgtg    1200
catacagtcc agcttggagc gaactgccta cccggaactg agtgtcaggc gtggaatgag    1260
acaaacgcgg ccataacagc ggaatgacac cggtaaaccg aaaggcagga acaggagagc    1320
gcacgaggga gccgccaggg ggaaacgcct ggtatcttta tagtcctgtc gggtttcgcc    1380
accactgatt tgagcgtcag atttcgtgat gcttgtcagg ggggcggagc ctatggaaaa    1440
acggctttgc cgcggccctc tcacttccct gttaagtatc ttcctggcat cttccaggaa    1500
atctccgccc cgttcgtaag ccatttccgc tcgccgcagt cgaacgaccg agcgtagcga    1560
gtcagtgagc gaggaagcgg aatatatccc ctaggtctag ggcggcggat ttgtcctact    1620
caggagagcg ttcaccgaca aacaacagat aaaacgaaag gcccagtctt tcgactgagc    1680
cttttgtttt atttgatgcc tctagattac accttcctct tcttcttggg gtcagccctg    1740
ctgtctccac cgagctgaga gaggtcgatt cttgtttcat agagcccgt aattgactga    1800
tgaatcagtg tggcgtccag gacctccttt gtagaggtgt accgctttct gtctatggtg    1860
gtgtcgaagt acttgaaggc tgcaggcgcg cccaagttgg tcagagtaaa caagtggata    1920
atgttttctg cctgctccct gatgggctta tccctgtgct tattgtaagc agaaagcacc    1980
ttatcgaggt tagcgtcggc gaggatcact cttttggaga attcgcttat ttgctcgatg    2040
atctcatcaa ggtagtgttt gtgttgttcc acgaacagct gcttctgctc attatcttcg    2100
ggagaccctt tgagctttc atagtggctg gccagataca agaaattaac gtatttagag    2160
ggcagtgcca gctcgttacc tttctgcagc tcgcccgcac tagcgagcat tcgtttccgg    2220
```

```
ccgttttcaa gctcaaagag agagtacttg ggaagcttaa tgatgaggtc ttttttgacc      2280
tctttatatc ctttcgcctc gagaaagtcg atggggtttt tttcgaagct tgatcgctcc      2340
atgattgtga tgcccagcag ttccttgacg cttttgagtt ttttagactt ccctttctcc      2400
actttggcca caaccagtac actgtaagcg actgtaggag aatcgaatcc gccgtatttc      2460
ttggggtccc aatctttttt gcgtgcgatc agcttgtcgc tgttccttt cggaggata        2520 ctttccttgg agaagcctcc ggtctgtact tcggtctttt taacgatgtt cacctgcggc      2580
atggacagga ccttccggac tgtcgcgaaa tccctaccct tgtcccacac gatttctcct      2640
gtttctccgt ttgtttcgat aagtggtcgc ttccgaatct ctccattggc cagtgtaatc      2700
tcggtcttga aaaaattcat aatattgctg taaagaagt  acttagcggt ggccttgcct      2760
atttcctgct cagactttgc gatcattttc ctaacatcgt acactttata gtctccgtaa      2820
acaaattcag attcaagctt gggatatttt ttgataagtg cagtgcctac cactgcattc      2880
aggtaggcat catgcgcatg gtggtaattg ttgatctctc tcaccttata aaactgaaag      2940 tccttttctga aatctgagac cagcttagac ttcagagtaa taactttcac ctctcgaatc     3000
agtttgtcat tttcatcgta cttggtgttc atgcgtgaat cgagaatttg gccacgtgc      3060 ttggtgatct ggcgtgtctc aacaagctgc cttttgatga agccggcttt atccaactca      3120
gacaggccac ctcgttcagc cttagtcaga ttatcgaact tccgttgtgt gatcagtttg      3180
gcgttcagca gctgccgcca ataatttttc attttcttga caacttcttc tgagggacg       3240 ttatcactct tccctctatt tttatcggat cttgtcaaca ctttattatc aatagaatca      3300
tctttgagaa aagactgggg cacgatatga tccacgtcgt agtcggagag ccgattgatg      3360
tccagttcct gatccacgta catgtccctg ccgttctgca ggtagtacag gtagagcttc      3420
tcattctgaa gctgggtgtt tcaactggg tgttccttaa ggatttggga ccccagttct       3480 tttatacccct cttcaatcct cttcatcctt tccctactgt tcttctgtcc cttctgggta    3540
gtttggttct ctcgggccat ctcgataacg atattctcgg gcttatgcct tcccattact      3600
ttgacgagtt catccacgac cttaacggtc tgcagtattc ccttttgat agctgggcta       3660 cctgcaagat tagcgatgtg ctcgtgaaga ctgtccccct ggccagaaac ttgtgctttc      3720
tggatgtcct ccttaaaggt gagagagtca tcatggatca actgcatgaa gttccggttg     3780
gcaaatccat cggacttaag aaaatccagg attgtctttc cactctgctt gtctcggatc      3840
ccattgatca gttttcttga cagccgcccc catcctgtat atcggcgcct cttgagctgt      3900
ttcatgactt tgtcgtcgaa gagatgagcg taagttttca agcgttcttc aatcatctcc      3960
ctatcttcaa caacgtaag  ggtgaggaca atgtcctcaa gaatgtcctc gttctcctca      4020
ttgtccagga agtccttgtc tttaatgatt ttcaggagat cgtgatacgt tcccagggat      4080
gcgttgaagc gatcctccac tccgctgatt tcaacagagt cgaaacattc aatctttttg     4140
aaatagtctc ttgtgagctg tttcacggta acttccggt tcgtcttgaa gaggaggtcc      4200
acgatagctt tcttctgctc tccagacagg aatgctggct ttctcatccc ttctgtgacg      4260
tatttgacct tggtgagctc gttataaact gtgaagtact cgtacagcag agagtgtta       4320 ggaagcacct tttcgttagg cagattttta tcaaagttag tcatcctttc gatgaaggac      4380
tgggcagagg ccccttatc cacgacttcc tcgaagttcc agggagtgat ggtctcttct       4440
gatttgcgag tcatccacgc gaatctggaa tttccccggg cgaggggcc tacatagtag       4500 ggtatccgaa atgtgaggat tttctcaatc ttttcccctgt tatctttcaa aaggggtag      4560
```

```
aaatcctctt gccgcctgag gatagcgtgc agttcgccca ggtgaatctg gtggggatg      4620 cttccattgt cgaaagtgcg ctgtttgcgc aacagatctt ctctgttaag ctttaccagc    4680
agctcctcgg tgccgtccat tttttccaag atgggcttaa taaatttgta aaattcctcc    4740
tggcttgctc cgccgtcaat gtatccggcg tagccatttt tagactgatc gaagaaaatt    4800
tccttgtact tctcaggcag ttgctgtctg acaagggcct tcagcaaagt caagtcttgg    4860
tggtgctcat catagcgctt gatcatacta gcgctcagcg gagctttggt gatctccgtg    4920
ttcactcgca gaatatcact cagcagaatg gcgtctgaca ggttctttgc cgccaaaaaa    4980
aggtctgcgt actggtcgcc gatctgggcc agcagattgt cgagatcatc atcgtaggtg    5040
tctttgctca gttgaagctt ggcatcttcg gccaggtcga agttagattt aaagttgggg    5100
gtcagcccga gtgacagggc gataagatta ccaaacaggc cgttcttctt ctccccaggg    5160
agctgtgcga tgaggttttc gagccgccgg gatttggaca gcctagcgct caggattgct    5220
ttggcgtcaa ctccggatgc gttgatcggg ttctcttcga aaagctgatt gtaagtctga    5280
accagttgga taaagagttt gtcgacatcg ctgttgtctg ggttcaggtc ccctcgatg     5340 aggaagtgtc cccgaaattt gatcatatgc gccagcgcga gatagatcaa ccgcaagtca    5400
gccttatcag tactgtctac aagcttcttc ctcagatgat atatggttgg gtacttttca    5460
tggtacgcca cctcgtccac gatattgcca aagattgggt ggcgctcgtg cttttatcc     5520 tcctccacca aaaggactc ctccagccta tggaagaaag agtcatccac cttagccatc     5580
tcattactaa agatctcctg caggtagcag atccgattct ttctgcgggt atatctgcgc    5640
cgtgctgttc ttttgagccg cgtggcttcg gcggtttccc cggagtcgaa caggagggcg    5700
ccaatgaggt tcttctttat gctgtggcga tcggtattgc ccagaacttt gaattttttg    5760
ctcggcacct tgtactcgtc cgtaatgacg gcccagccga cgctgtttgt gccgatatcg    5820
agcccaatgg agtacttctt gtccatgggt acctttctcc tctttaatga attctgtgtg    5880
aaattgttat ccgctcacaa ttgaatctat cataattgtg agcgctcaca attgtaaagg    5940
ttagatctaa aactagtggc agcggctaac taagcggcct gctgactttc tcgccgatca    6000
aaaggcattt tgctattaag ggattgacga gggcgtatct cgcagtaag atgcggcatt     6060 gttgtgtgga aatgtgaggt tttagagcta gaaatagcaa gttaaaataa ggctagtccg    6120
ttatcaactt gaaaaagtgg caccgagtcg gtgcttttttt taattcgaaa agcgctcaac   6180
gagcaggctt ttttggtcga cagacagtag tggcagcggc taactaagcg gcctgctgac    6240
tttctcgccg atcaaaaggc attttgctat taagggattg acgagggcgt atctgcgcag    6300
taagatgcgc cccgcatttg ttgtgtggaa tgtgaggttt tagagctaga aatagcaagt    6360
taaaataagg ctagtccgtt atcaacttga aaaagtggca ccgagtcggt gctttttta     6420 attcgaaaag cctgctcaac gagcaggctt ttttggtcga cagttcatag gtgattgctc    6480
aggacatttc tgttagaagg aatcgttttc cttactttc cttacgcaca agagttccgt     6540
agctgttcaa gtttgtgttt caactgttct cgtcgttccc gcaacaagtc ctcttcagaa    6600
atgagctttt gctc                                                      6614
```

<210> SEQ ID NO 4
<211> LENGTH: 6614
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<221> NAME/KEY: modified_base
<222> LOCATION: (6064)..(6064)
<223> OTHER INFORMATION: a, c, t or g
<220> FEATURE:
<221> NAME/KEY: modified_base
<222> LOCATION: (6071)..(6071)
<223> OTHER INFORMATION: a, c, t or g
<220> FEATURE:
<221> NAME/KEY: modified_base
<222> LOCATION: (6076)..(6076)
<223> OTHER INFORMATION: a, c, t or g
<220> FEATURE:
<221> NAME/KEY: misc_feature
<222> LOCATION: (6061)..(6078)
<223> OTHER INFORMATION: This motif may comprise a sequence selected
      from SEQ ID NOS 5, 7, 9, 11, 13, 15, 17, 19, 21, 23, 25, or 27
<220> FEATURE:
<221> NAME/KEY: misc_feature
<222> LOCATION: (6319)..(6336)
<223> OTHER INFORMATION: This motif may comprise a sequence selected
      from SEQ ID NOS 6, 8, 10, 12, 14, 16, 18, 20, 22, 24, or 26

<400> SEQUENCE: 4

```
ctctgcttgg acggacagga tgtatgctgt ggcttttta aggataacta ccttgggggc      60
cttttcattg ttttccaact ccgggatctg gtcacgcagg gcaaaaaagc tccgttttag   120
ctcgttcctc ctctggcgct ccaagacgtt gtgtgttcgc ctcttgacat tctcctcggt   180
gtccgagggc cctgtgtgaa tttgttatcc gctcacaatt ccacacagac gtcgttgaca   240
attaatcatc ggcatagtat atcggcatag tataatacga caaggtgagg aactaaacca   300
tggccaagtt gaccagtgcc gttccggtgc tcaccgcgcg cgacgtcgcc ggagcggtcg   360
agttctggac cgaccggctc gggttctccc gggacttcgt ggaggacgac ttcgccggtg   420
tggtccggga cgacgtgacc ctgttcatca gcgcggtcca ggaccaggtg gtgccggaca   480
acaccctggc ctgggtgtgg gtgcgcgcc tggacgagct gtacgccgag tggtcggagg   540
tcgtgtccac gaacttccgg gacgcctccg ggccggccat gaccgagatc ggcgagcagc   600
cgtggggcg gagttcgcc ctgcgcgacc cggccggcaa ctgcgtgcac ttcgtggccg   660
aggagcagga ctgagagctc gcttggactc ctgttgatag atccagtaat gacctcagaa   720
ctccatctgg atttgttcag aacgctcggt tgccgccggg cgttttttat tggtgagaat   780
ccaagcacta gtaacaactt atatcgtatg gggctgactt caggtgctac atttgaagag   840
ataaattgca ctgaaatcta gtaatatttt atctgattaa taagatgatc ttcttgagat   900
cgttttggtc tgcgcgtaat ctcttgctct gaaaacgaaa aaaccgcctt gcagggcggt   960
ttttcgaagg ttctctgagc taccaactct ttgaaccgag gtaactggct tggaggagcg  1020
cagtcaccaa aacttgtcct ttcagtttag ccttaaccgg cgcatgactt caagactaac  1080
tcctctaaat caattaccag tggctgctgc cagtggtgct tttgcatgtc tttccgggtt  1140
ggactcaaga cgatagttac cggataaggc gcagcggtcg gactgaacgg ggggttcgtg  1200
catacagtcc agcttggagc gaactgccta cccggaactg agtgtcaggc gtggaatgag  1260
acaaacgcgg ccataacagc ggaatgacac cggtaaaccg aaaggcagga acaggagagc  1320
gcacgaggga gccgccaggg ggaaacgcct ggtatcttta tagtcctgtc gggtttcgcc  1380
accactgatt tgagcgtcag atttcgtgat gcttgtcagg ggggcggagc ctatggaaaa  1440
acggctttgc cgcggccctc tcacttccct gttaagtatc ttcctggcat cttccaggaa  1500
atctccgccc cgttcgtaag ccatttccgc tcgccgcagt cgaacgaccg agcgtagcga  1560
gtcagtgagc gaggaagcgg aatatatccc ctaggtctag gcggcggat tgtcctact   1620
caggagagcg ttcaccgaca acaacagat aaaacgaaag gcccagtctt tcgactgagc  1680
```

```
ctttcgtttt atttgatgcc tctagattac accttcctct tcttcttggg gtcagccctg    1740
ctgtctccac cgagctgaga gaggtcgatt cttgtttcat agagcccgt aattgactga     1800 tgaatcagtg tggcgtccag gacctccttt gtagaggtgt accgctttct gtctatggtg    1860
gtgtcgaagt acttgaaggc tgcaggcgcg cccaagttgg tcagagtaaa caagtggata    1920
atgttttctg cctgctccct gatgggctta tccctgtgct tattgtaagc agaaagcacc    1980
ttatcgaggt tagcgtcggc gaggatcact cttttggaga attcgcttat ttgctcgatg    2040
atctcatcaa ggtagtgttt gtgttgttcc acgaacagct gcttctgctc attatcttcg    2100
ggagacccct tgagcttttc atagtggctg gccagataca agaaattaac gtatttagag    2160
ggcagtgcca gctcgttacc tttctgcagc tcgcccgcac tagcgagcat tcgtttccgg    2220
ccgttttcaa gctcaaagag agagtacttg ggaagcttaa tgatgaggtc ttttttgacc    2280
tctttatatc ctttcgcctc gagaaagtcg atggggtttt tttcgaagct tgatcgctcc    2340
atgattgtga tgcccagcag ttccttgacg cttttgagtt ttttagactt cccttttctcc   2400 actttggcca caaccagtac actgtaagcg actgtaggag aatcgaatcc gccgtatttc    2460
ttggggtccc aatcttttt gcgtgcgatc agcttgtcgc tgttccttttt cgggaggata    2520 ctttccttgg agaagcctcc ggtctgtact tcggtctttt taacgatgtt cacctgcggc    2580
atggacagga cctccggac tgtcgcgaaa tccctaccct tgtcccacac gatttctcct    2640
gtttctccgt ttgtttcgat aagtggtcgc ttccgaatct ctccattggc cagtgtaatc    2700
tcggtcttaa aaaattcat aatattgctg taaagaagt acttagcggt ggccttgcct     2760
atttcctgct cagactttgc gatcatttc ctaacatcgt acactttata gtctccgtaa    2820
acaaattcag attcaagctt gggatatttt ttgataagtg cagtgcctac cactgcattc    2880
aggtaggcat catgcgcatg gtggtaattg ttgatctctc tcaccttata aaactgaaag    2940
tcctttctga aatctgagac cagcttagac ttcagagtaa taactttcac ctctcgaatc    3000
agtttgtcat tttcatcgta cttggtgttc atgcgtgaat cgagaatttg ggccacgtgc    3060
ttggtgatct ggcgtgtctc aacaagctgc cttttgatga agccggcttt atccaactca    3120
gacaggccac ctcgttcagc cttagtcaga ttatcgaact tccgttgtgt gatcagtttg    3180
gcgttcagca gctgccgcca ataatttttc attttcttga caacttcttc tgagggacg    3240 ttatcactct tccctctatt tttatcggat cttgtcaaca cttttattatc aatagaatca   3300 tctttgagaa aagactgggg cacgatatga tccacgtcgt agtcggagag ccgattgatg    3360
tccagttcct gatccacgta catgtccctg ccgttctgca ggtagtacag gtagagcttc    3420
tcattctgaa gctgggtgtt ttcaactggg tgttccttaa ggatttggga ccccagttct    3480
tttataccct cttcaatcct cttcatcctt tccctactgt tcttctgtcc cttctgggta    3540
gtttggttct ctcgggccat ctcgataacg atattctcgg gcttatgcct tcccattact    3600
ttgacgagtt catccacgac cttaacggtc tgcagtattc cttttttgat agctgggcta    3660
cctgcaagat tagcgatgtg ctcgtgaaga ctgtcccct ggccagaaac ttgtgctttc    3720
tggatgtcct ccttaaaggt gagagagtca tcatggatca actgcatgaa gttccggttg    3780
gcaaatccat cggacttaag aaaatccagg attgtctttc cactctgctt gtctcggatc    3840
ccattgatca gttttcttga cagccgcccc catcctgtat atcggcgcct cttgagctgt    3900
ttcatgactt tgtcgtcgaa gagatgagcg taagttttca agcgttcttc aatcatctcc    3960
ctatcttcaa acaacgtaag ggtgaggaca atgtcctcaa gaatgtcctc gttctcctca    4020
```

| | |
|---|---|
| ttgtccagga agtccttgtc tttaatgatt tcaggagat cgtgatacgt tcccagggat | 4080 |
| gcgttgaagc gatcctccac tccgctgatt caacagagt cgaaacattc aatcttttg | 4140 |
| aaatagtctt ctttgagctg tttcacggta actttccggt tcgtcttgaa gaggaggtcc | 4200 |
| acgatagctt tcttctgctc tccagacagg aatgctggct ttctcatccc ttctgtgacg | 4260 |
| tatttgacct tggtgagctc gttataaact gtgaagtact cgtacagcag agagtgttta | 4320 |
| ggaagcacct tttcgttagg cagattttta tcaaagttag tcatcctttc gatgaaggac | 4380 |
| tgggcagagg ccccttatc cacgacttcc tcgaagttcc agggagtgat ggtctcttct | 4440 |
| gatttgcgag tcatccacgc gaatctggaa tttccccggg cgaggggggcc tacatagtag | 4500 |
| ggtatccgaa atgtgaggat tttctcaatc tttccctgt tatctttcaa aaagggggtag | 4560 |
| aaatcctctt gccgcctgag gatagcgtgc agttcgccca ggtgaatctg gtgggggatg | 4620 |
| cttccattgt cgaaagtgcg ctgtttgcgc aacagatctt ctctgttaag ctttaccagc | 4680 |
| agctcctcgg tgccgtccat ttttccaag atgggcttaa taaatttgta aaattcctcc | 4740 |
| tggcttgctc cgccgtcaat gtatccggcg tagccatttt tagactgatc gaagaaaatt | 4800 |
| tccttgtact tctcaggcag ttgctgtctg acaagggcct tcagcaaagt caagtcttgg | 4860 |
| tggtgctcat catagcgctt gatcatacta gcgctcagcg gagctttggt gatctccgtg | 4920 |
| ttcactcgca gaatatcact cagcagaatg gcgtctgaca ggttctttgc cgccaaaaaa | 4980 |
| aggtctgcgt actggtcgcc gatctgggcc agcagattgt cgagatcatc atcgtaggtg | 5040 |
| tctttgctca gttgaagctt ggcatcttcg gccaggtcga agttagattt aaagttgggg | 5100 |
| gtcagcccga gtgacagggc gataagatta ccaaacaggc cgttcttctt ctccccaggg | 5160 |
| agctgtgcga tgaggttttc gagccgccgg gatttggaca gcctagcgct caggattgct | 5220 |
| ttggcgtcaa ctccggatgc gttgatcggg ttctcttcga aaagctgatt gtaagtctga | 5280 |
| accagttgga taaagagttt gtcgacatcg ctgttgtctg ggttcaggtc cccctcgatg | 5340 |
| aggaagtgtc cccgaaattt gatcatatgc gccagcgcga gatagatcaa ccgcaagtca | 5400 |
| gccttatcag tactgtctac aagcttcttc ctcagatgat atatggttgg gtacttttca | 5460 |
| tggtacgcca cctcgtccac gatattgcca aagattgggt ggcgctcgtg ctttttatcc | 5520 |
| tcctccacca aaaaggactc ctccagccta tggaagaaag agtcatccac cttagccatc | 5580 |
| tcattactaa agatcctctg caggtagcag atccgattct ttctgcgggt atatctgcgc | 5640 |
| cgtgctgttc ttttgagccg cgtggcttcg gcggtttccc cggagtcgaa caggagggcg | 5700 |
| ccaatgaggt tcttctttat gctgtggcga tcggtattgc ccagaacttt gaattttttg | 5760 |
| ctcggcacct tgtactcgtc cgtaatgacg gcccagccga cgctgtttgt gccgatatcg | 5820 |
| agcccaatgg agtacttctt gtccatgggt acctttctcc tctttaatga attctgtgtg | 5880 |
| aaattgttat ccgctcacaa ttgaatctat cataattgtg agcgctcaca attgtaaagg | 5940 |
| ttagatctaa aactagtggc agcggctaac taagcggcct gctgactttc tcgccgatca | 6000 |
| aaaggcattt tgctattaag ggattgacga gggcgtatct gcgcagtaag atgcggcatt | 6060 |
| ccangatggg naccanccgt tttagagcta gaaatagcaa gttaaaataa ggctagtccg | 6120 |
| ttatcaactt gaaaaagtgg caccgagtcg gtgcttttt taattcgaaa agcgctcaac | 6180 |
| gagcaggctt ttttggtcga cagacagtag tggcagcggc taactaagcg gcctgctgac | 6240 |
| tttctcgccg atcaaaaggc attttgctat taagggattg acgagggcgt atctgcgcag | 6300 |
| taagatgcgc cccgcattac cagrwkggsm mcmmccgttt tagagctaga aatagcaagt | 6360 |
| taaaataagg ctagtccgtt atcaacttga aaaagtggca ccgagtcggt gcttttttta | 6420 |

```
attcgaaaag cctgctcaac gagcaggctt ttttggtcga cagttcatag gtgattgctc    6480
aggacatttc tgttagaagg aatcgttttc cttactttc cttacgcaca agagttccgt    6540
agctgttcaa gtttgtgttt caactgttct cgtcgtttcc gcaacaagtc ctcttcagaa    6600
atgagctttt gctc                                                      6614
```

```
<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ccaggatggg caccaacc                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
accaggatgg gcaccacc                                                  18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
ccaggatggg caccagcc                                                  18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
accaggatgg gcaccacc                                                  18

<210> SEQ ID NO 9
<211> LENGTH: 18
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
ccaggatggg caccaccc                                                    18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
accaggatgg gcaccacc                                                    18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
ccaggatggg caccatcc                                                    18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
accaggatgg gcaccacc                                                    18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
ccaggatggg aaccaccc                                                    18

<210> SEQ ID NO 14
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
accaggatgg gaccaccc                                                    18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
ccaggatggg gaccaccc                                                    18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
accaggatgg gaccaccc                                                    18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
ccaggatggg caccaccc                                                    18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
accaggatgg gaccaccc                                                    18

<210> SEQ ID NO 19
<211> LENGTH: 18
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
ccaggatggg taccaccc                                                    18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
accaggatgg gaccaccc                                                    18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
ccaagatggg caccaccc                                                    18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
accagatggg caccaccc                                                    18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
ccaggatggg caccaccc                                                    18

<210> SEQ ID NO 24
<211> LENGTH: 18

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
accagatggg caccaccc                                                   18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
ccacgatggg caccaccc                                                   18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
accagatggg caccaccc                                                   18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
ccatgatggg caccaccc                                                   18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
accagatggg caccaccc                                                   18

<210> SEQ ID NO 29

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: Any unnatural nucleotide

<400> SEQUENCE: 29
tcacacaatg tagncatcac gg                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Any unnatural nucleotide

<400> SEQUENCE: 30
accaggatgg gcaccanccc gg                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: Any unnatural nucleotide

<400> SEQUENCE: 31
accangatgg gcaccacccc gg                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(13)
<223> OTHER INFORMATION: Any unnatural nucleotide

<400> SEQUENCE: 32
tcacacaatg tanagatcac gg                                              22
```

```
<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Any unnatural nucleotide

<400> SEQUENCE: 33
accaggatgg gcaccanccc gg                                              22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(13)
<223> OTHER INFORMATION: Any unnatural nucleotide

<400> SEQUENCE: 34
tgttgtgtgg aantgtgagc gg                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: Any unnatural nucleotide

<400> SEQUENCE: 35
ttgtcactac tctgaccngc gg                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: Any unnatural nucleotide

<400> SEQUENCE: 36
ttgtcactac tctgaccnag gg                                              22
```

```
<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: Any unnatural nucleotide

<400> SEQUENCE: 37
tcacacaatg tacncatcac gg                                                  22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: Any unnatural nucleotide

<400> SEQUENCE: 38
accangatgg gcaccacccc gg                                                  22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: Any unnatural nucleotide

<400> SEQUENCE: 39
tcacacaatg tatngatcac gg                                                  22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: Any unnatural nucleotide

<400> SEQUENCE: 40
tcacacaatg tatnaatcac gg                                                  22
```

```
<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: Any unnatural nucleotide

<400> SEQUENCE: 41
accaggatgg gnaccacccc gg                                                  22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(13)
<223> OTHER INFORMATION: Any unnatural nucleotide

<400> SEQUENCE: 42
attcacaata ctntctttaa gg                                                  22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: g, a, u, c or unnatural nucleotides NaM -
      (2R,3S,5R)-2-(hydroxymethyl)-5-(1-methoxynaphthalen-2-
      yl)tetrahydro-furan-3-ol or TPT3 - 6-((2R,4S,5R)-4-hydroxy-5
      (hydroxymethyl) tetrahydrofuran-2-yl)thieno[2,3-c]pyridine-7(6H)-
      thione

<400> SEQUENCE: 43
gaccaggatg ggcaccancc                                                     20

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
```

```
<223> OTHER INFORMATION: c, t, a, g or unnatural nucleotides NaM -
      (2R,3S,5R)-2-(hydroxymethyl)-5-(1-methoxynaphthalen-2-
      yl)tetrahydro-furan-3-ol or TPT3 - 6-((2R,4S,5R)-4-hydroxy-5
      (hydroxymethyl) tetrahydrofuran-2-yl)thieno[2,3-c]pyridine-7(6H)-
      thione

<400> SEQUENCE: 44
gaccaggatg ggcaccancc agg                                            23

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(13)
<223> OTHER INFORMATION: g, a, u, c or unnatural nucleotides NaM -
      (2R,3S,5R)-2-(hydroxymethyl)-5-(1-methoxynaphthalen-2-
      yl)tetrahydro-furan-3-ol or TPT3 - 6-((2R,4S,5R)-4-hydroxy-5
      (hydroxymethyl) tetrahydrofuran-2-yl)thieno[2,3-c]pyridine-7(6H)-
      thione

<400> SEQUENCE: 45
gaccaggatg ggnaccaccc                                                20

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: c, t, a, g or unnatural nucleotides NaM -
      (2R,3S,5R)-2-(hydroxymethyl)-5-(1-methoxynaphthalen-2-
      yl)tetrahydro-furan-3-ol or TPT3 - 6-((2R,4S,5R)-4-hydroxy-5
      (hydroxymethyl) tetrahydrofuran-2-yl)thieno[2,3-c]pyridine-7(6H)-
      thione

<400> SEQUENCE: 46
gaccaggatg ggnaccaccc agg                                            23

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
gaccaggatg ggcaccaacc                                                20

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: Unnatural nucleotide dTPT3TP - (((2R,3S,5R)-3-
      hydroxy-5-(7-thioxothieno [2,3-c]pyridin-6(7H)-yl)tetrahydrofuran-
      2-yl)methyltetrahydrogen triphosphate)

<400> SEQUENCE: 48
guauguugug uggaanugug ag                                                  22

<210> SEQ ID NO 49
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gaccaggaug ggcaccaccc                                                     20

<210> SEQ ID NO 50
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
guauguugug uggaaaugug ag                                                  22

<210> SEQ ID NO 51
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
guugugugga aaugugag                                                       18

<210> SEQ ID NO 52
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uguugugugg aaugugag                                                       18

<210> SEQ ID NO 53
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(12)
```

<400> SEQUENCE: 53 tca cat ttc cac a                                                           13
Ser His Phe His
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser His Phe His
1

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: Any unnatural nucleotide

<400> SEQUENCE: 55
ccaggatggg caccancccg g                                                     21

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: a, c, u or g

<400> SEQUENCE: 56
ccaggatggg caccancc                                                         18

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (11)..(11)
<223> OTHER INFORMATION: Any unnatural nucleotide

```
<400> SEQUENCE: 57
ccaggatggg naccaccccg g                                            21

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (11)..(11)
<223> OTHER INFORMATION: a, c, u or g

<400> SEQUENCE: 58
ccaggatggg naccaccc                                                18

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: Any unnatural nucleotide

<400> SEQUENCE: 59
ccangatggg caccaccccg g                                            21

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: a, c, u or g

<400> SEQUENCE: 60
ccangatggg caccaccc                                                18

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
```

<223> OTHER INFORMATION: Any unnatural nucleotide

<400> SEQUENCE: 61
ccaggatggg caccancccg g                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (11)..(11)
<223> OTHER INFORMATION: Any unnatural nucleotide

<400> SEQUENCE: 62
ccaggatggg naccaccccg g                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: Any unnatural nucleotide

<400> SEQUENCE: 63
ccangatggg caccaccccg g                                              21

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: Any unnatural nucleotide

<400> SEQUENCE: 64
tcacacaatg tagngatcac gg                                             22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base

```
<222> LOCATION: (12)..(12)
<223> OTHER INFORMATION: Any unnatural nucleotide

<400> SEQUENCE: 65
accaggatgg gnaccacccc gg                                              22

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: a, c, t or g

<400> SEQUENCE: 66
gaccaggatg ggcaccancc                                                 20

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: a, c, t or g

<400> SEQUENCE: 67
gaccaggatg ggcaccancc agg                                             23

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a, c, t or g

<400> SEQUENCE: 68
gaccaggatg ggnaccaccc                                                 20

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a, c, t or g

<400> SEQUENCE: 69
gaccaggatg ggnaccaccc agg                                             23

<210> SEQ ID NO 70
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 70
gaccaggatg ggcaccaacc                                               20

<210> SEQ ID NO 71
<211> LENGTH: 22
<212> TYPE: RNA
<213> ORGANISM: Unknown
<220> FEATURE:
<223> OTHER INFORMATION: Description of Unknown:
      target sequence

<400> SEQUENCE: 71
guauguugug uggaayugug ag                                            22

<210> SEQ ID NO 72
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gaccaggaug ggcaccaccc                                               20

<210> SEQ ID NO 73
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
guauguugug uggaaaugug ag                                            22

<210> SEQ ID NO 74
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
guugugugga aaugugag                                                 18

<210> SEQ ID NO 75
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uguugugugg aaugugag                                                 18

<210> SEQ ID NO 76
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 76
ccaggatggg caccaycccg g                                              21

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a, c, t or g

<400> SEQUENCE: 77
ccaggatggg caccancc                                                  18

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ccaggatggg yaccacccg g                                               21

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: a, c, t or g

<400> SEQUENCE: 79
ccaggatggg naccaccc                                                  18

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ccaygatggg caccaccccg g                                              21

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
```

<223> OTHER INFORMATION: a, c, t or g

<400> SEQUENCE: 81
ccangatggg caccaccc                                                    18

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a, c, t or g

<400> SEQUENCE: 82
ccaggatggg caccancccg g                                                21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: a, c, t or g

<400> SEQUENCE: 83
ccaggatggg naccacccg g                                                 21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t or g

<400> SEQUENCE: 84
ccangatggg caccacccg g                                                 21

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t or g

<400> SEQUENCE: 85
tcacacaatg tagngatcac gg                                               22

<210> SEQ ID NO 86
<211> LENGTH: 22
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 86
accaggatgg gyaccacccc gg                                              22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t or g

<400> SEQUENCE: 87
tcacacaatg tagncatcac gg                                              22

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
accaggatgg gcaccayccc gg                                              22

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
accaygatgg gcaccacccc gg                                              22

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a, c, t or g

<400> SEQUENCE: 90
tcacacaatg tanagatcac gg                                              22

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
```

<223> OTHER INFORMATION: a, c, t or g

<400> SEQUENCE: 91
accaggatgg gcaccanccc gg                                               22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a, c, t or g

<400> SEQUENCE: 92
tgttgtgtgg aantgtgagc gg                                               22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ttgtcactac tctgaccygc gg                                               22

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: a, c, t or g

<400> SEQUENCE: 94
ttgtcactac tctgaccnag gg                                               22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t or g

<400> SEQUENCE: 95
tcacacaatg tacncatcac gg                                               22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (5)..(5)
<223> OTHER INFORMATION: a, c, t or g

<400> SEQUENCE: 96
accangatgg gcaccacccc gg                                             22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t or g

<400> SEQUENCE: 97
tcacacaatg tatngatcac gg                                             22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tcacacaatg tatyaatcac gg                                             22

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t or g

<400> SEQUENCE: 99
accaggatgg gnaccacccc gg                                             22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a, c, t or g

<400> SEQUENCE: 100
attcacaata ctntctttaa gg                                             22
```

PRODUCTION OF UNNATURAL NUCLEOTIDES USING A CRISPR/CAS9 SYSTEM

CROSS-REFERENCE

This application is the U.S. National Stage entry of International Application No. PCT/US2016/067353, filed Dec. 16, 2016, which claims the benefit of U.S. Provisional Application No. 62/269,890, filed on Dec. 18, 2015, both of which are incorporated herein by reference in their entireties.

STATEMENT OF GOVERNMENT LICENSE RIGHTS

This invention was made with government support under GM060005 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 28, 2021, is named "36271-803 831 SL" and is 67,890 bytes in size.

BACKGROUND OF THE INVENTION

The ability to sequence-specifically synthesize/amplify oligonucleotides (DNA or RNA) with polymerases, for example by PCR or isothermal amplification systems (e.g., transcription with T7 RNA polymerase), has revolutionized biotechnology. In addition to all of the potential applications in nanotechnology, this has enabled a diverse range of new technologies such as the in vitro evolution via SELEX (Systematic Evolution of Ligands by Exponential Enrichment) of RNA and DNA aptamers and enzymes. See, for example, Oliphant A R, Brandl C J & Struhl K (1989), Defining the sequence specificity of DNA-binding proteins by selecting binding sites from random-sequence oligonucleotides: analysis of yeast GCN4 proteins, *Mol. Cell Biol.*, 9:2944-2949; Tuerk C & Gold L (1990), Systematic evolution of ligands by exponential enrichment: RNA ligands to bacteriophage T4 DNA polymerase, Science, 249:505-510; Ellington A D & Szostak J W (1990), In vitro selection of RNA molecules that bind specific ligands, *Nature*, 346:818-822.

In some aspects, these applications are restricted by the limited chemical/physical diversity present in the natural genetic alphabet (the four natural nucleotides A, C, G, and T in DNA, and the four natural nucleotides A, C, G, and U in RNA). Disclosed herein is a method of generating nucleic acids that contains an expanded genetic alphabet.

SUMMARY OF THE INVENTION

Described herein, in certain embodiments, are methods, cells, engineered microorganisms, plasmids, and kits for increased production of a nucleic acid molecule that comprises an unnatural nucleotide. In some embodiments, also described herein include methods, cells, engineered microorganisms, plasmids, and kits that utilizes a CRISPR/Cas editing system for increased production of a nucleic acid molecule that comprises an unnatural nucleotide. In some embodiments, further described herein include methods, cells, engineered microorganisms, plasmids, and kits that utilizes a CRISPR/Cas editing system for retention of a nucleic acid molecule that comprises an unnatural nucleotide.

Disclosed herein, in certain embodiments, is an engineered cell comprising: (a) a first nucleic acid molecule encoding a Cas9 polypeptide or variants thereof; (b) a second nucleic acid molecule encoding a single guide RNA (sgRNA) comprising a crRNA-tracrRNA scaffold; and (c) a third nucleic acid molecule comprising an unnatural nucleotide; wherein the first nucleic acid molecule, the second nucleic acid molecule, and the third nucleic acid molecule are encoded in one or more plasmids, and the sgRNA encoded by the second nucleic acid molecule comprises a target motif that recognizes a modification at the unnatural nucleotide position within the third nucleic acid molecule. In some embodiments, the modification at the unnatural nucleotide position within the third nucleic acid molecule generates a modified third nucleic acid molecule. In some embodiments, the modification is a substitution. In some embodiments, the modification is a deletion. In some embodiments, the modification is an insertion. In some embodiments, the sgRNA encoded by the second nucleic acid molecule further comprises a protospacer adjacent motif (PAM) recognition element. In some embodiments, the PAM element is adjacent to the 3' terminus of the target motif. In some embodiments, the target motif is between 15 to 30 nucleotides in length. In some embodiments, the target motif is about 15, 16, 17, 18, 19, 20, 21, or 22 nucleotides in length. In some embodiments, a nucleotide within the target motif that pairs with the modification at the unnatural nucleotide position within the third nucleic acid molecule is located between 3 to 22, between 5 to 20, between 5 to 18, between 5 to 15, between 5 to 12, or between 5 to 10 nucleotides from the 5' terminus of PAM. In some embodiments, a nucleotide within the target motif that pairs with the modification at the unnatural nucleotide position within the third nucleic acid molecule is located about 3, 4, 5, 6, 7, 8, 9, 10, 11, 12, 13, 14, or 15 nucleotides from the 5' terminus of PAM. In some embodiments, the combination of Cas9 polypeptide or variants thereof and sgRNA modulates replication of the modified third nucleic acid molecule. In some embodiments, the combination of Cas9 polypeptide or variants thereof and sgRNA decreases the replication rate of the modified third nucleic acid molecule by about 80%, 85%, 95%, 99%, or higher. In some embodiments, the production of the third nucleic acid molecule in the cell increases by about 50%, 60%, 70%, 80%, 90%, 95%, 96%, 97%, 98%, 99%, or higher. In some embodiments, the Cas9 polypeptide or variants thereof generate a double-stranded break. In some embodiments, the Cas9 polypeptide is a wild-type Cas9. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, 0-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of

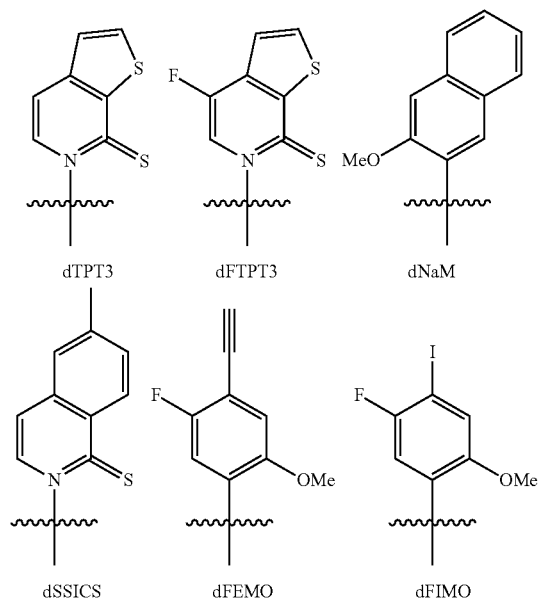

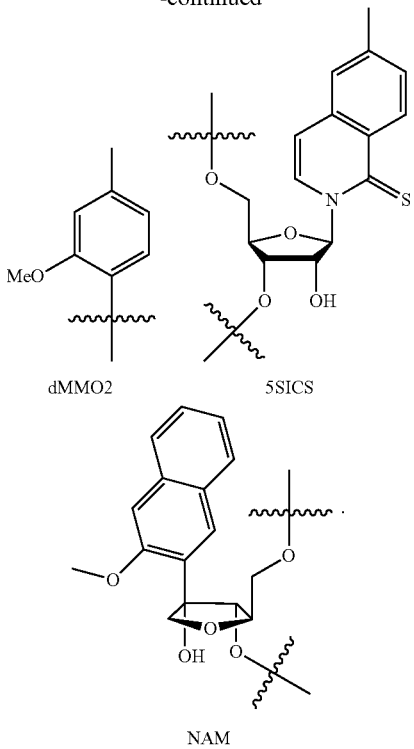

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$, alkyl, C$_2$-C$_{10}$ alkenyl, C$_2$-C$_{10}$ alkynyl, —O[(CH$_2$)nO]mCH$_3$, —O(CH$_2$)nOCH3, —O(CH$_2$)nNH$_2$, —O(CH$_2$)nCH$_3$, —O(CH$_2$)n-ONH$_2$, and —O(CH$_2$)nON[(CH$_2$)n CH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the unnatural nucleotide further comprises an unnatural backbone. In some embodiments, the unnatural backbone is selected from the group consisting of a phosphorothioate, chiral phosphorothioate, phosphorodithioate, phosphotriester, aminoalkylphosphotriester, C$_1$-C$_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates. In some embodiments, the sgRNA has less than about 20%, 15%, 10%, 5%, 3%, 1%, or less off-target binding rate. In some embodiments, the cell further comprises an additional nucleic acid molecule that encodes an additional single guide RNA (sgRNA) comprising a crRNAtracrRNA scaffold. In some embodiments, the third nucleic acid molecule further comprises an additional unnatural nucleotide. In some embodiments, the cell is a prokaryotic cell. In some embodiments, the cell is *E. coli*. In some embodiments, the cell is a fungal cell. In some embodiments, the cell is a yeast cell. In some embodiments, the cell is a eukaryotic cell. In some embodiments, the cell generates a stable cell line. In some embodiments, disclosed herein is an engineered cell comprising: (a) a first nucleic acid molecule encoding a Cas9 polypeptide or variants thereof, (b) a second nucleic acid molecule encoding two or more single guide RNAs (sgRNAs) wherein each sgRNA comprises a crRNA-tracrRNA scaffold; and (c) a third nucleic acid molecule comprising an unnatural nucleotide; wherein the first nucleic acid molecule, the second nucleic acid molecule, and the third nucleic acid molecule are encoded in one or more plasmids, and each of the sgRNAs encoded by the second nucleic acid molecule comprises a target motif that recognizes a modification at the unnatural nucleotide position within the third nucleic acid molecule.

Disclosed herein, in certain embodiments, is an in vivo method of increasing the production of a nucleic acid molecule containing an unnatural nucleotide, comprising incubating a cell with: (a) a first nucleic acid molecule encoding a Cas9 polypeptide or variants thereof; (b) a second nucleic acid molecule encoding a single guide RNA (sgRNA) comprising a crRNA-tracrRNA scaffold; and (c) a third nucleic acid molecule comprising an unnatural nucleotide; wherein a modification at the unnatural nucleotide position within the third nucleic acid molecule generates a modified third nucleic acid molecule, and the combination of the Cas9 polypeptide or variants thereof and sgRNA modulates replication of the modified third nucleic acid molecule to increase the production of the nucleic acid molecule containing an unnatural nucleotide. In some embodiments, the modification is a substitution. In some embodiments, the modification is a deletion. In some embodiments, the modification is an insertion. In some embodiments, the sgRNA encoded by the second nucleic acid molecule comprises a target motif that recognizes a modification at the unnatural nucleotide position within the third nucleic acid molecule. In some embodiments, the sgRNA encoded by the second nucleic acid molecule further comprises a protospacer adjacent motif (PAM) recognition element. In some embodiments, PAM is adjacent to the 3' terminus of the target motif. In some embodiments, the target motif is between 15 to 30 nucleotides in length. In some embodiments, the target motif is about 15, 16, 17, 18, 19, 20, 21, or 22 nucleotides in length. In some embodiments, a nucleotide within the target motif that pairs with the modification at the unnatural nucleotide position within the third nucleic acid molecule is located between 3 to 22, between 5 to 20, between 5 to 18, between 5 to 15, between 5 to 12, or between 5 to 10 nucleotides from the 5' terminus of PAM. In some embodiments, a nucleotide within the target motif that pairs with the modification at the unnatural nucleotide position within the third nucleic acid molecule is located about 3, 4, 5, 6, 7, 8, 9, 10, 11, 12, 13, 14, or 15 nucleotides from the 5' terminus of PAM. In some embodiments, the combination of Cas9 polypeptide or variants thereof and sgRNA modulates replication of the modified third nucleic acid molecule. In some embodiments, the combination of Cas9 polypeptide or variants thereof and sgRNA decreases the replication rate of the modified third nucleic acid molecule by about 80%, 85%, 95%, 99%, or higher. In some embodiments, the production of the third nucleic acid molecule increases by about 50%, 60%, 70%, 80%, 90%, 95%, 96%, 97%, 98%, 99%, or higher. In some embodiments, the Cas9 polypeptide or variants thereof generate a double-stranded break. In some embodiments, the Cas9 polypeptide is a wild-type Cas9. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, 0-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido [5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido [4,5-b]indol-2-one), pyridoindole cytidine (H-pyrido [3',2':4,5]pyrrolo[2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N_6$-isopentenyladenine, 1-methylguanine, 1-methylinosine, 2,2-dimethylguanine, 2-methyladenine, 2-methylguanine, 3-methylcytosine, 5-methylcytosine, $N_6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-$N_6$-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of

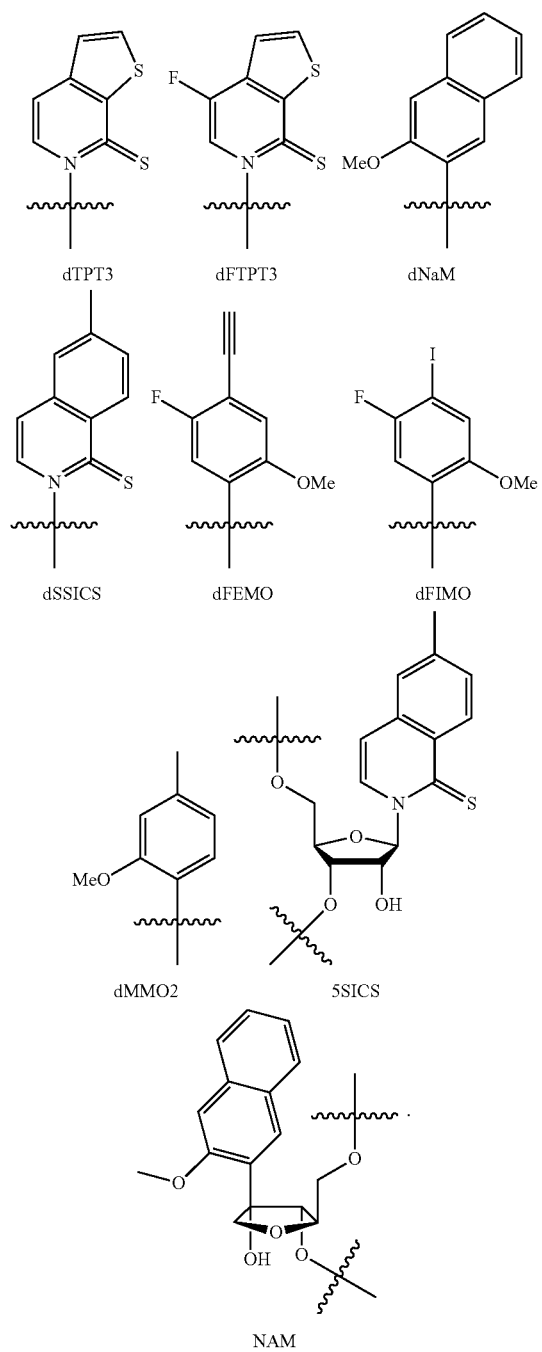

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$ alkyl, C$_2$-C$_{10}$ alkenyl, C$_2$-C$_{10}$ alkynyl, —O[(CH$_2$)nO]mCH$_3$, —O(CH$_2$)nOCH3, —O(CH$_2$)nNH$_2$, —O(CH$_2$)nCH$_3$, —O(CH$_2$)n-ONH$_2$, and —O(CH$_2$)nON[(CH$_2$)n CH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the unnatural nucleotide further comprises an unnatural backbone. In some embodiments, the unnatural backbone is selected from the group consisting of a phosphorothioate, chiral phosphorothioate, phosphorodithioate, phosphotriester, aminoalkylphosphotriester, C$_1$-C$_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates. In some embodiments, the sgRNA has less than about 20%, 15%, 10%, 5%, 3%, 1%, or less off-target binding rate. In some embodiments, the method further comprises an additional nucleic acid molecule that encodes an additional single guide RNA (sgRNA) comprising a crRNA-tracrRNA scaffold. In some embodiments, the third nucleic acid molecule further comprises an additional unnatural nucleotide. In some embodiments, the first nucleic acid molecule, the second nucleic acid molecule, and the third nucleic acid molecule are encoded in one or more plasmids. In some embodiments, the incubating further comprises a transformation step. In some embodiments, the cell is a prokaryotic cell. In some embodiments, the cell is *E. coli*. In some embodiments, the cell is a fungal cell. In some embodiments, the cell is a yeast cell. In some embodiments, the cell is a eukaryotic cell. In some embodiments, the cell generates a stable cell line. In some embodiments, is an in vivo method of increasing the production of a nucleic acid molecule containing an unnatural nucleotide, comprising incubating a cell with: (a) a first nucleic acid molecule encoding a Cas9 polypeptide or variants thereof; (b) a second nucleic acid molecule encoding two or more single guide RNAs (sgRNAs) wherein each sgRNA comprises a crRNA-tracrRNA scaffold; and (c) a third nucleic acid molecule comprising an unnatural nucleotide; wherein a modification at the unnatural nucleotide position within the third nucleic acid molecule generates a modified third nucleic acid molecule, and the combination of the Cas9 polypeptide or variants thereof and the two or more sgRNAs modulates replication of the modified third nucleic acid molecule to increase the production of the nucleic acid molecule containing an unnatural nucleotide.

Disclosed herein, in certain embodiments, is a nucleic acid molecule containing an unnatural nucleotide produced by a process comprising incubating a cell with: (a) a first nucleic acid molecule encoding a Cas9 polypeptide or variants thereof (b) a second nucleic acid molecule encoding a single guide RNA (sgRNA) comprising a crRNA-tracrRNA scaffold; and (c) a third nucleic acid molecule comprising an unnatural nucleotide; wherein a modification at the unnatural nucleotide position within the third nucleic acid molecule generates a modified third nucleic acid molecule, and the combination of the Cas9 polypeptide or variants thereof and sgRNA modulates replication of the modified third nucleic acid molecule leading to production of the nucleic acid molecule containing an unnatural nucleotide. In some embodiments, the modification is a substitution. In some embodiments, the modification is a deletion. In some embodiments, the modification is an insertion. In some embodiments, the sgRNA encoded by the second nucleic acid molecule comprises a target motif that recognizes a modification at the unnatural nucleotide position within the third nucleic acid molecule. In some embodiments, the sgRNA encoded by the second nucleic acid molecule further comprises a protospacer adjacent motif (PAM) recognition element. In some embodiments, PAM is adjacent to the 3' terminus of the target motif. In some embodiments, the target motif is between 15 to 30 nucleotides in length. In some embodiments, the target motif is about 15, 16, 17, 18, 19, 20, 21, or 22 nucleotides in length. In some embodiments, a nucleotide within the target motif that pairs with the modification at the unnatural nucleotide position within the third nucleic acid molecule is located between 3 to 22, between 5 to 20, between 5 to 18, between 5 to 15, between 5 to 12, or between 5 to 10 nucleotides from the 5' terminus of PAM. In some embodiments, a nucleotide within the target motif that pairs with the modification at the unnatural nucleotide position within the third nucleic acid molecule is located about 3, 4, 5, 6, 7, 8, 9, 10, 11, 12, 13, 14, or 15 nucleotides from the 5' terminus of PAM. In some embodiments, the combination of Cas9 polypeptide or variants thereof and sgRNA modulates replication of the modified third nucleic acid molecule. In some embodiments, the combination of Cas9 polypeptide or variants thereof and sgRNA decreases the replication rate of the modified third nucleic acid molecule by about 80%, 85%, 95%, 99%, or higher. In some embodiments, the production of the third nucleic acid molecule increases by about 50%, 60%, 70%, 80%, 90%, 95%, 96%, 97%, 98%, 99%, or higher. In some embodiments, the Cas9 polypeptide or variants thereof generate a double-stranded break. In some embodiments, the Cas9 polypeptide is a wild-type Cas9. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido [5,4-b][1,4]benzothiazin-2(3H)-one), G-clamps, phenoxazine cytidine (9-(2-aminoethoxy)-H-pyrimido[5,4-b][1, 4]benzoxazin-2(3H)-one), carbazole cytidine (2H-pyrimido [4,5-b]indol-2-one), pyridoindole cytidine (H-pyrido [3',2': 4,5]pyrrolo[2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of

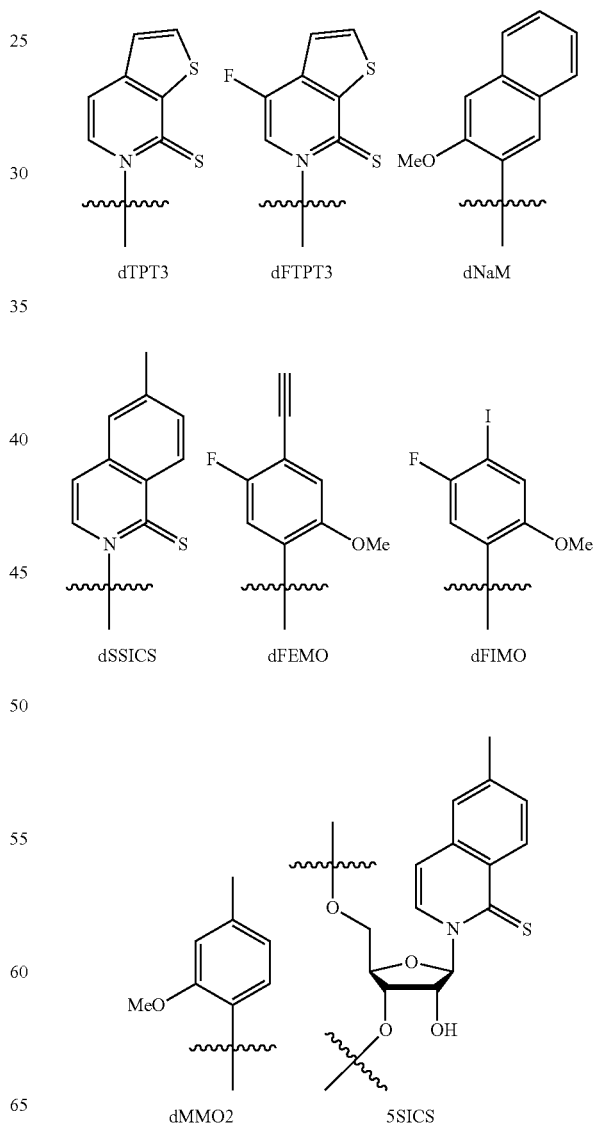

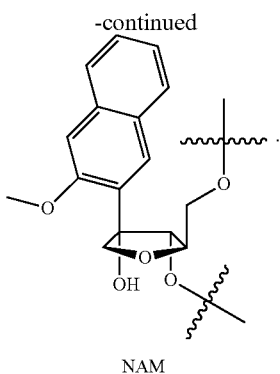

NAM

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH$_3$, 2'-O(CH$_2$)$_2$OCH$_3$ wherein the alkyl, alkenyl and alkynyl may be substituted or unsubstituted C$_1$-C$_{10}$ alkyl, C$_2$-C$_{10}$ alkenyl, C$_2$-C$_{10}$ alkynyl, —O[(CH$_2$)nO]mCH$_3$, —O(CH$_2$)nOCH3, —O(CH$_2$)nNH$_2$, —O(CH$_2$)nCH$_3$, —O(CH$_2$)n-ONH$_2$, and —O(CH$_2$)nON [(CH$_2$)n CH$_3$)]$_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the unnatural nucleotide further comprises an unnatural backbone. In some embodiments, the unnatural backbone is selected from the group consisting of a phosphorothioate, chiral phosphorothioate, phosphorodithioate, phosphotriester, aminoalkylphosphotriester, C$_1$-C$_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates. In some embodiments, the sgRNA has less than about 20%, 15%, 10%, 5%, 3%, 1%, or less off-target binding rate. In some embodiments, the nucleic acid molecule further comprises an additional nucleic acid molecule that encodes an additional single guide RNA (sgRNA) comprising a crRNA-tracrRNA scaffold. In some embodiments, the third nucleic acid molecule further comprises an additional unnatural nucleotide. In some embodiments, the first nucleic acid molecule, the second nucleic acid molecule, and the third nucleic acid molecule are encoded in one or more plasmids. In some embodiments, the incubating further comprises a transformation step. In some embodiments, the cell is a prokaryotic cell. In some embodiments, the cell is E. coli. In some embodiments, the cell is a fungal cell. In some embodiments, the cell is a yeast cell. In some embodiments, the cell is a eukaryotic cell. In some embodiments, the cell generates a stable cell line. In some embodiments, is a nucleic acid molecule containing an unnatural nucleotide produced by a process comprising incubating a cell with: (a) a first nucleic acid molecule encoding a Cas9 polypeptide or variants thereof; (b) a second nucleic acid molecule encoding two or more single guide RNAs (sgRNAs) wherein each sgRNA comprises a crRNA-tracrRNA scaffold; and (c) a third nucleic acid molecule comprising an unnatural nucleotide; wherein a modification at the unnatural nucleotide position within the third nucleic acid molecule generates a modified third nucleic acid molecule, and the combination of the Cas9 polypeptide or variants thereof and the two or more sgRNAs modulates replication of the modified third nucleic acid molecule leading to production of the nucleic acid molecule containing an unnatural nucleotide.

Disclosed herein, in certain embodiments, is a semi-synthetic organism produced by a process comprising incubating an organism with: (a) a first nucleic acid molecule encoding a Cas9 polypeptide or variants thereof; (b) a second nucleic acid molecule encoding a single guide RNAs (sgRNAs) wherein the sgRNA comprises a crRNA-tracrRNA scaffold; and (c) a third nucleic acid molecule comprising an unnatural nucleotide; wherein a modification at the unnatural nucleotide position within the third nucleic acid molecule generates a modified third nucleic acid molecule, and the combination of the Cas9 polypeptide or variants thereof and the sgRNA modulates replication of the modified third nucleic acid molecule leading to production of the semi-synthetic organism containing a nucleic acid molecule comprising an unnatural nucleotide. In some embodiments, the combination of Cas9 polypeptide or variants thereof and sgRNA decreases the replication rate of the modified third nucleic acid molecule by about 80%, 85%, 95%, 99%, or higher. In some embodiments, the modification is a substitution. In some embodiments, the modification is a deletion. In some embodiments, the modification is an insertion. In some embodiments, the organism further comprises an additional nucleic acid molecule that encodes an additional single guide RNA (sgRNA) comprising a crRNA-tracrRNA scaffold. In some embodiments, the organism is a cell. In some embodiments, the cell is a bacterial cell. In some embodiments, the cell is a fungal cell. In some embodiments, the cell is a yeast cell. In some embodiments, the cell is a eukaryotic cell. In some embodiments, the cell is a unicellular protozoan. In some embodiments, the cell generates a stable cell line.

Disclosed herein, in certain embodiments, is an isolated and purified plasmid comprising a sequence selected from SEQ ID NOs: 1-4. In some embodiments, the isolated and purified plasmid comprises a sequence of SEQ ID NO: 4. In some embodiments, the W motif of SEQ ID NO: 4 comprises a sequence selected from SEQ ID NOs: 5, 7, 9, 11, 13, 15, 17, 19, 21, 23, 25, or 27. In some embodiments, the Y motif of SEQ ID NO: 4 comprises a sequence selected from SEQ ID NOs: 6, 8, 10, 12, 14, 16, 18, 20, 22, 24, or 26.

Disclosed herein, in certain embodiments, is a kit comprising an isolated and purified plasmid of described above, and a nucleic acid molecule comprising an unnatural nucleotide.

Also described herein, in certain embodiments, is a kit comprising a stable cell line generated from a cell described above.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates the relative cleavage efficiency (RCE) of variations of an sgRNA target against a DNA template. FIGS. 1A and 1B disclose SEQ ID NOS 66-69, respectively, in order of appearance. FIG. 1C discloses SEQ ID NOS 70 and 67, respectively, in order of appearance.

FIG. 4 illustrates percent UBP retention upon using different sgRNAs. FIG. 4B discloses SEQ ID NOS 71-74 and 74-75, respectively, in order of appearance.

FIG. 5 exemplifies the major and minor mutations commonly observed in the target DNA. FIGS. 5A and 5B disclose SEQ ID NOS 53-54 and 53-54, respectively, in order of appearance.

FIG. 6 illustrates the percentage of dNaM-dTPT3 retention, in either the coding or noncoding strand, at three different positions relative to the same PAM within the hGFP gene (6 sequences total). FIG. 6 discloses SEQ ID NOS 76-82, 77, 83, 79, 84, and 81, respectively, in order of appearance.

FIG. 7 illustrates the 16 sequences examined in which the dNaM of a dNaM-dTPT3 UBP was flanked by all possible nucleotides. FIG. 7 discloses SEQ ID NOS 85-100, respectively, in order of appearance.

DETAILED DESCRIPTION OF THE INVENTION

Figure 1A:
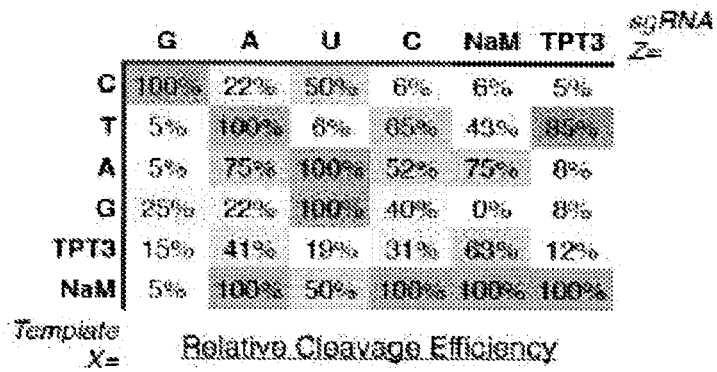
FIGS. 1A and 1B illustrate RCE given variations of a nucleotide, include using UBPs, at two different positions relative to a protospacer adjacent motif (PAM).

The development of an unnatural base pair (UBP) allowing cells to store and retrieve increased information has a profound effect in practical applications, including human health applications by facilitating the production of proteins containing unnatural amino acids for development as therapeutics. However, retention of the UBP within a population of cells is sequence-dependent and in some sequences, the UBP is not sufficiently maintained or maintained at a reduced level, for practical applications (e.g. protein expression). In some instances, mutations within the sequences at the position of the unnatural base are introduced during the replication process, resulting in reduced retention of UBP within a population of cells.

Disclosed herein, in certain embodiments, are methods, compositions, cells, engineered microorganisms, plasmids, and kits for increased production of a nucleic acid molecule that comprises an unnatural nucleotide. In some instances, disclosed herein is an engineered cell comprising: (a) a first nucleic acid molecule encoding a Cas9 polypeptide or variants thereof; (b) a second nucleic acid molecule encoding a single guide RNA (sgRNA) comprising a crRNA-tracrRNA scaffold; and (c) a third nucleic acid molecule comprising an unnatural nucleotide; wherein the first nucleic acid molecule, the second nucleic acid molecule, and the third nucleic acid molecule are encoded in one or more plasmids, and the sgRNA encoded by the second nucleic acid molecule comprises a target motif that recognizes a modification at the unnatural nucleotide position within the third nucleic acid molecule.

In some embodiments, also provided herein include an in vivo method of increasing the production of a nucleic acid molecule containing an unnatural nucleotide, comprising incubating a cell with: (a) a first nucleic acid molecule encoding a Cas9 polypeptide or variants thereof; (b) a second nucleic acid molecule encoding a single guide RNA (sgRNA) comprising a crRNA-tracrRNA scaffold; and (c) a third nucleic acid molecule comprising an unnatural nucleotide; wherein a modification at the unnatural nucleotide position within the third nucleic acid molecule generates a modified third nucleic acid molecule, and the combination of the Cas9 polypeptide or variants thereof and sgRNA modulates replication of the modified third nucleic acid molecule to increase the production of the nucleic acid molecule containing an unnatural nucleotide.

In some embodiments, further provided herein include a nucleic acid molecule containing an unnatural nucleotide produced by a process comprising incubating a cell with: (a) a first nucleic acid molecule encoding a Cas9 polypeptide or variants thereof; (b) a second nucleic acid molecule encoding a single guide RNA (sgRNA) comprising a crRNA-tracrRNA scaffold; and (c) a third nucleic acid molecule comprising an unnatural nucleotide; wherein a modification at the unnatural nucleotide position within the third nucleic acid molecule generates a modified third nucleic acid molecule, and the combination of the Cas9 polypeptide or variants thereof and sgRNA modulates replication of the modified third nucleic acid molecule leading to production of the nucleic acid molecule containing an unnatural nucleotide.

In some embodiments, additional provided herein include a semi-synthetic organism produced by a process comprising incubating an organism with: (a) a first nucleic acid molecule encoding a Cas9 polypeptide or variants thereof; (b) a second nucleic acid molecule encoding a single guide RNAs (sgRNAs) wherein the sgRNA comprises a crRNA-tracrRNA scaffold; and (c) a third nucleic acid molecule comprising an unnatural nucleotide; wherein a modification at the unnatural nucleotide position within the third nucleic acid molecule generates a modified third nucleic acid molecule, and the combination of the Cas9 polypeptide or variants thereof and the sgRNA modulates replication of the modified third nucleic acid molecule leading to production of the semi-synthetic organism containing a nucleic acid molecule comprising an unnatural nucleotide.

In some embodiments, also described herein include an isolated and purified plasmid comprising a sequence selected from SEQ ID NOs: 1-4, and kits comprising one or more of the plasmids and/or stable cell lines described herein.

CRISPR/CRISPR-Associated (Cas) Editing System

In some embodiments, methods, cells, and engineered microorganisms disclosed herein utilize a CRISPR/CRISPR-associated (Cas) system for modification of a nucleic acid molecule comprising an unnatural nucleotide. In some instances, the CRISPR/Cas system modulates retention of a modified nucleic acid molecule that comprises a modification at its unnatural nucleotide position. In some instances, the retention is a decrease in replication of the modified nucleic acid molecule. In some instances, the CRISPR/Cas system generates a double-stranded break within a modified nucleic acid molecule leading to degradation involving DNA repair proteins such as RecBCD and its associated nucleases.

In some embodiments, the CRISPR/Cas system involves (I) an integration of short regions of genetic material that are homologous to a nucleic acid molecule of interest comprising an unnatural nucleotide, called "spacers", in clustered arrays in the host genome, (2) expression of short guiding RNAs (crRNAs) from the spacers, (3) binding of the crRNAs to specific portions of the nucleic acid molecule of interest referred to as protospacers, and (4) degradation of protospacers by CRISPR-associated nucleases (Cas). In some cases, a Type-II CRISPR system has been described in the bacterium *Streptococcus pyogenes*, in which Cas9 and two non-coding small RNAs (pre-crRNA and tracrRNA (trans-activating CRISPR RNA)) act in concert to target and degrade a nucleic acid molecule of interest in a sequence-specific manner (Jinek et al "A Programmable Dual-RNA-Guided DNA Endonuclease in Adaptive Bacterial Immunity," Science 337(6096):816-821 (August 2012, epub Jun. 28, 2012)).

In some instances, the two noncoding RNAs are further fused into one single guide RNA (sgRNA). In some instances, the sgRNA comprises a target motif that recognizes a modification at the unnatural nucleotide position within a nucleic acid molecule of interest. In some embodiments, the modification is a substitution, insertion, or deletion. In some cases, the sgRNA comprises a target motif that recognizes a substitution at the unnatural nucleotide position within a nucleic acid molecule of interest. In some cases, the sgRNA comprises a target motif that recognizes a deletion at the unnatural nucleotide position within a nucleic acid molecule of interest. In some cases, the sgRNA comprises a target motif that recognizes an insertion at the unnatural nucleotide position within a nucleic acid molecule of interest.

In some cases, the target motif is between 10 to 30 nucleotides in length. In some instances, the target motif is between 15 to 30 nucleotides in length. In some cases, the target motif is about 11, 12, 13, 14, 15, 16, 17, 18, 19, 20, 21, 22, 23, 24, 25, 26, 27, 28, 29, or 30 nucleotides in length. In some cases, the target motif is about 15, 16, 17, 18, 19, 20, 21, or 22 nucleotides in length.

In some cases, the sgRNA further comprises a protospacer adjacent motif (PAM) recognition element. In some instances, PAM is located adjacent to the 3' terminus of the target motif. In some cases, a nucleotide within the target motif that forms Watson-Crick base pairing with the modification at the unnatural nucleotide position within the nucleic acid molecule of interest is located between 3 to 22, between 5 to 20, between 5 to 18, between 5 to 15, between 5 to 12, or between 5 to 10 nucleotides from the 5' terminus of PAM. In some cases, a nucleotide within the target motif that forms Watson-Crick base pairing with the modification at the unnatural nucleotide position within the nucleic acid molecule of interest is located about 3, 4, 5, 6, 7, 8, 9, 10, 11, 12, 13, 14, or 15 nucleotides from the 5' terminus of PAM.

In some instances, a CRISPR/Cas system utilizes a Cas9 polypeptide or a variant thereof. Cas9 is a double stranded nuclease with two active cutting sites, one for each strand of the double helix. In some instances, the Cas9 polypeptide or variants thereof generate a double-stranded break. In some cases, the Cas9 polypeptide is a wild-type Cas9. In some instances, the Cas9 polypeptide is an optimized Cas9 for expression in a cell and/or engineered microorganism described herein.

In some embodiments, the Cas9/sgRNA complex binds to a portion of the nucleic acid molecule of interest (e.g., DNA) that contains a sequence match to, for example, the 17-20 nucleotides of the sgRNA upstream of PAM. Once bound, two independent nuclease domains in Cas9 then each cleaves one of the DNA strands 3 bases upstream of the PAM, leaving a blunt end DNA double stranded break (DSB). The presence of DSB then results, in some instances, to degradation of the DNA of interest by RecBCD and its associated nucleases.

In some instances, the Cas9/sgRNA complex modulates retention of a modified nucleic acid molecule that comprises a modification at its unnatural nucleotide position. In some instances, the retention is a decrease in replication of the modified nucleic acid molecule. In some cases, the Cas9/sgRNA decreases the replication rate of the modified nucleic acid molecule by about 80%, 85%, 95%, 99%, or higher.

In some instances, the production of the nucleic acid molecule comprising an unnatural nucleotide increases by about 30%, 40%, 50%, 55%, 60%, 65%, 70%, 75%, 80%, 85%, 90%, 95%, 96%, 97%, 98%, 99%, or higher. In some instances, the production of the nucleic acid molecule comprising an unnatural nucleotide increases by about 50%, 60%, 70%, 80%, 90%, 95%, 96%, 97%, 98%, 99%, or higher.

In some cases, the retention of the nucleic acid molecule comprising an unnatural nucleotide increases by about 30%, 40%, 50%, 55%, 60%, 65%, 70%, 75%, 80%, 85%, 90%, 95%, 96%, 97%, 98%, 99%, or higher. In some instances, the retention of the nucleic acid molecule comprising an unnatural nucleotide increases by about 50%, 60%, 70%, 80%, 90%, 95%, 96%, 97%, 98%, 99%, or higher.

In some embodiments, the CRISPR/Cas system comprises two or more sgRNAs. In some instances, each of the two or more sgRNAs independently comprises a target motif that recognizes a modification at the unnatural nucleotide position within a nucleic acid molecule of interest. In some embodiments, the modification is a substitution, insertion, or deletion. In some cases, each of the two or more sgRNAs comprises a target motif that recognizes a substitution at the unnatural nucleotide position within a nucleic acid molecule of interest. In some cases, each of the two or more sgRNAs comprises a target motif that recognizes a deletion at the unnatural nucleotide position within a nucleic acid molecule of interest. In some cases, each of the two or more sgRNAs comprises a target motif that recognizes an insertion at the unnatural nucleotide position within a nucleic acid molecule of interest.

In some embodiments, the specificity of binding of the CRISPR components to the nucleic acid molecule of interest is controlled by the non-repetitive spacer elements in the pre-crRNA portion of sgRNA, which upon transcription along with the tracrRNA portion, directs the Cas9 nuclease to the protospacer:crRNA heteroduplex and induces double-strand breakage (DSB) formation. In some instances, the specificity of sgRNA is about 80%, 85%, 90%, 95%, 96%, 97%, 98%, 99%, or higher. In some instances, sgRNA has less than about 20%, 15%, 10%, 5%, 3%, 1%, or less off-target binding rate.

Nucleic Acid Molecules

In some embodiments, a nucleic acid (e.g., also referred to herein as nucleic acid molecule of interest) is from any source or composition, such as DNA, cDNA, gDNA (genomic DNA), RNA, siRNA (short inhibitory RNA), RNAi, tRNA, mRNA or rRNA (ribosomal RNA), for example, and is in any form (e.g., linear, circular, supercoiled, single-stranded, double-stranded, and the like). In some embodiments, nucleic acids comprise nucleotides, nucleosides, or polynucleotides. In some cases, nucleic acids comprise natural and unnatural nucleic acids. In some cases, a nucleic acid also comprises unnatural nucleic acids, such as DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Exemplary natural deoxyribonucleotides include dATP, dTTP, dCTP, dGTP, dADP, dTDP, dCDP, dGDP, dAMP, dTMP, dCMP, and dGMP. Exemplary natural ribonucleotides include ATP, UTP, CTP, GTP, ADP, UDP, CDP, GDP, AMP, UMP, CMP, and GMP. For RNA, the uracil base is uridine. A nucleic acid sometimes is a vector, plasmid, phagemid, autonomously replicating sequence (ARS), centromere, artificial chromosome, yeast artificial chromosome (e.g., YAC) or other nucleic acid able to replicate or be replicated in a host cell. In some cases, an unnatural nucleic acid is a nucleic acid analogue. In additional cases, an unnatural nucleic acid is from an extracellular source. In other cases, an unnatural nucleic acid is available to the intracellular space of an organism provided herein, e.g., a genetically modified organism.

Unnatural Nucleic Acids

A nucleotide analog, or unnatural nucleotide, comprises a nucleotide which contains some type of modification to either the base, sugar, or phosphate moieties. In some embodiments, a modification comprises a chemical modification. In some cases, modifications occur at the 3'OH or 5'OH group, at the backbone, at the sugar component, or at the nucleotide base. Modifications, in some instances, optionally include non-naturally occurring linker molecules and/or of interstrand or intrastrand cross links. In one aspect, the modified nucleic acid comprises modification of one or more of the 3'OH or 5'OH group, the backbone, the sugar component, or the nucleotide base, and/or addition of non-naturally occurring linker molecules. In one aspect, a modified backbone comprises a backbone other than a phosphodiester backbone. In one aspect, a modified sugar comprises a sugar other than deoxyribose (in modified DNA) or other than ribose (modified RNA). In one aspect, a modified base comprises a base other than adenine, guanine, cytosine or thymine (in modified DNA) or a base other than adenine, guanine, cytosine or uracil (in modified RNA).

In some embodiments, the nucleic acid comprises at least one modified base. In some instances, the nucleic acid comprises 2, 3, 4, 5, 6, 7, 8, 9, 10, 15, 20, or more modified bases. In some cases, modifications to the base moiety include natural and synthetic modifications of A, C, G, and T/U as well as different purine or pyrimidine bases. In some embodiments, a modification is to a modified form of adenine, guanine cytosine or thymine (in modified DNA) or a modified form of adenine, guanine cytosine or uracil (modified RNA).

A modified base of a unnatural nucleic acid includes, but is not limited to, uracil-5-yl, hypoxanthin-9-yl (I), 2-amino-adenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, 0-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C—CI1/4) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine([5,4-b][1,4]benzoxazin-2(3H)-one), phenothiazine cytidine (1H-pyrimido[5,4-b][1, 4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4, 5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thioguanine, 2-thio-thymine, 4-thio-thymine, 5-propynyl-uracil, 4-thio-uracil, $N_4$-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke- and Lebleu Eds., CRC Press, 1993, 273-288. Additional base modifications can be found, for example, in U.S. Pat.

No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acid in some cases include one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo[2.3-d]pyrimidin-5-yl, 2-amino-4-oxopyrolo [2, 3-d]pyrimidin-5-yl, 2-amino-4-oxopyrrolo[2.3-d]pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, a modified base of a unnatural nucleic acid is depicted below, wherein the wavy line identifies a point of attachment to the (deoxy)ribose or ribose.

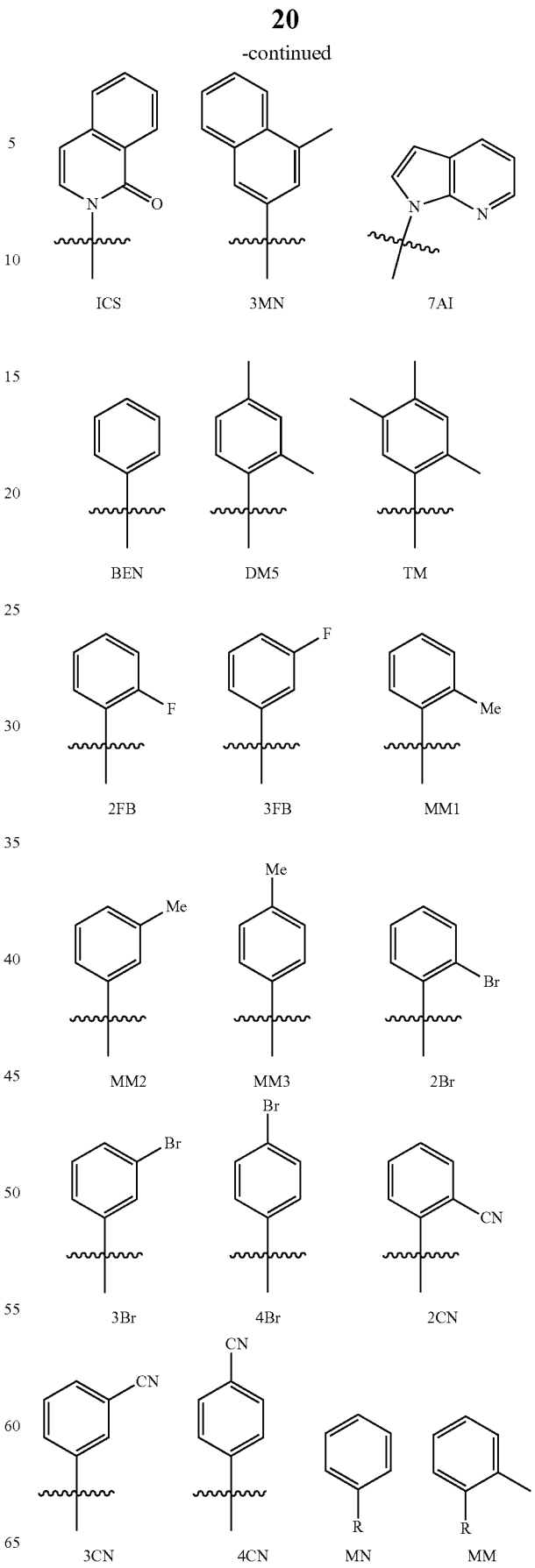

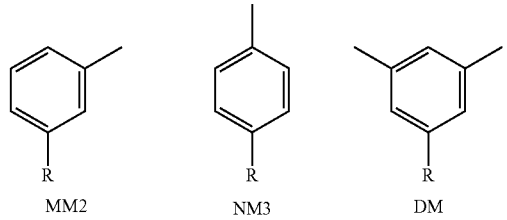
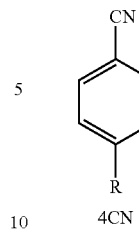
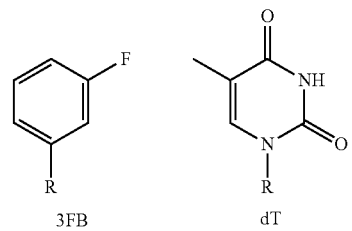
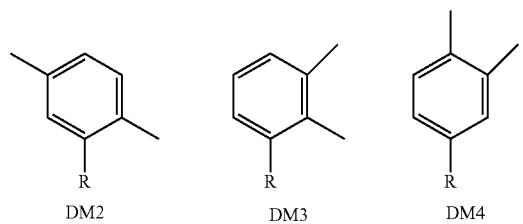
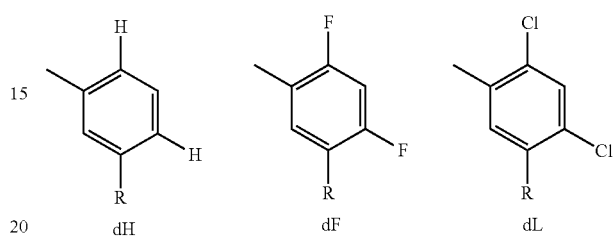
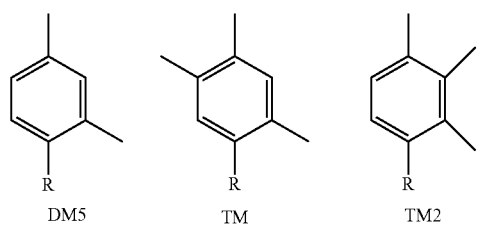
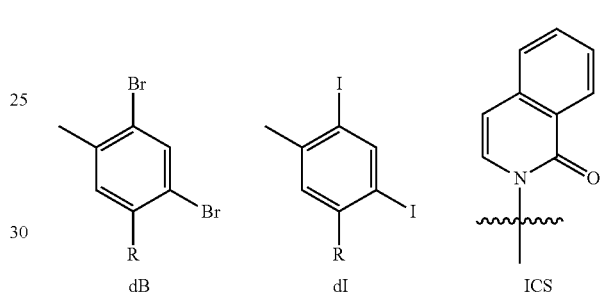
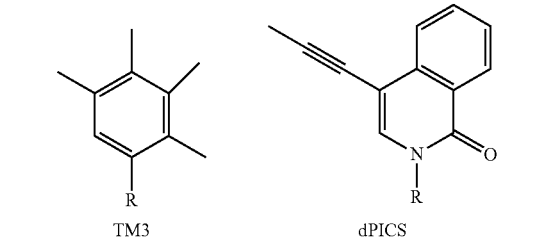
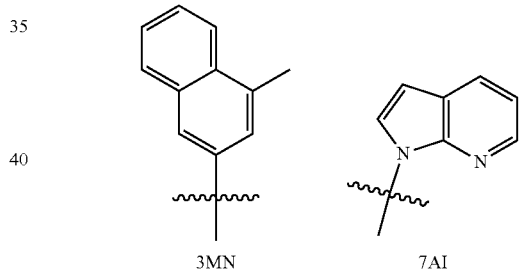
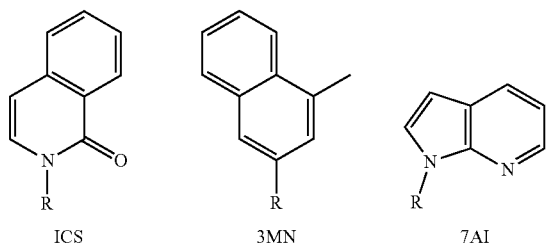
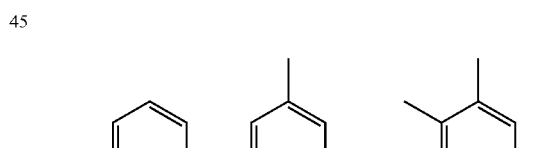
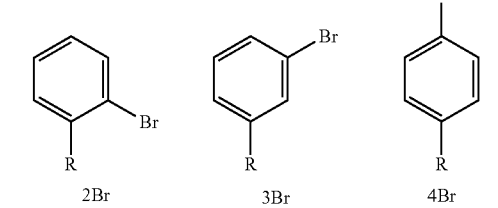
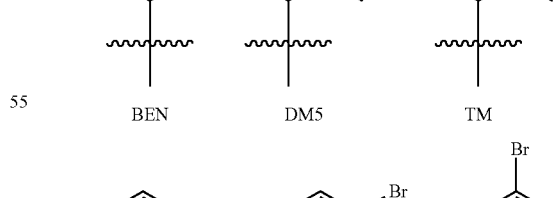
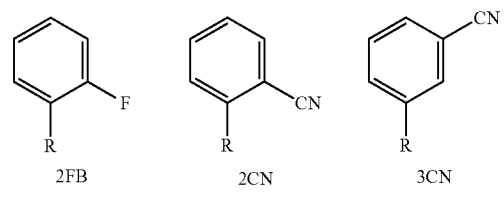
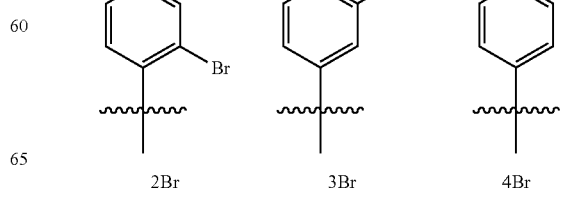

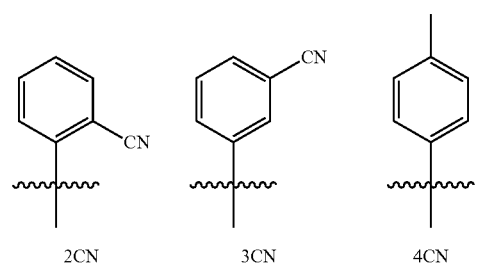
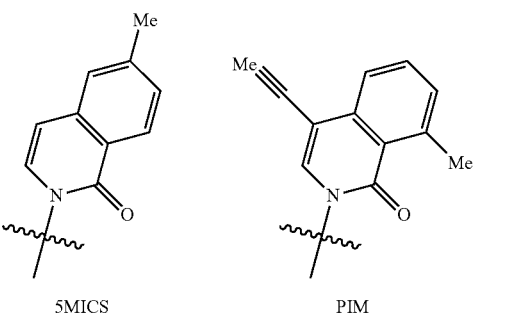
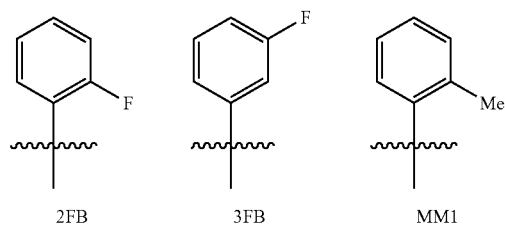
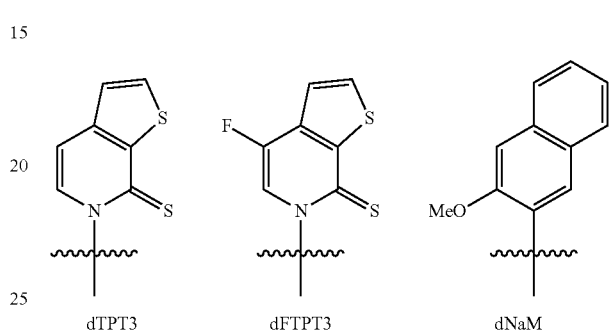
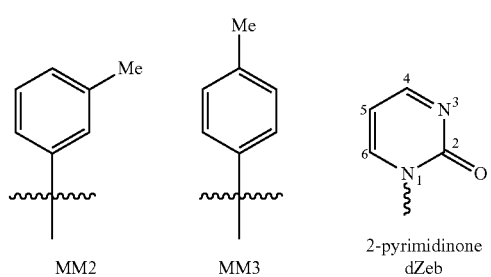
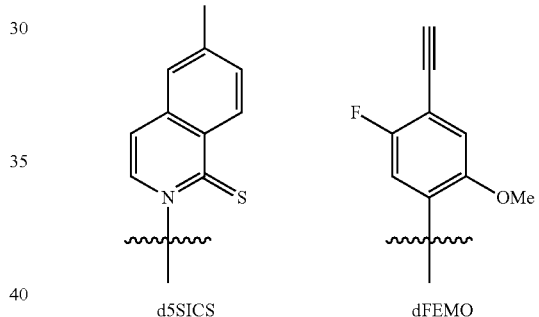
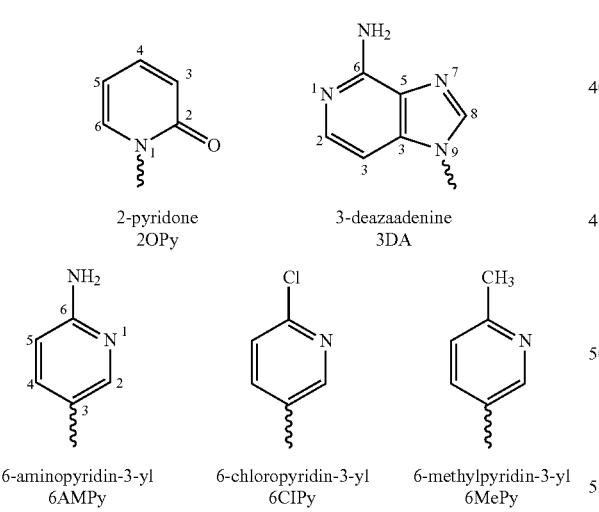
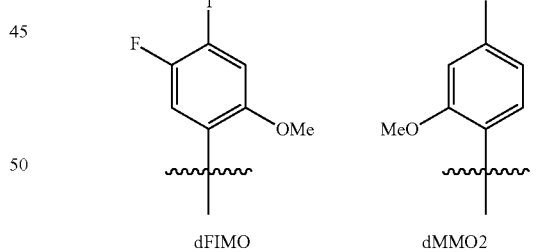
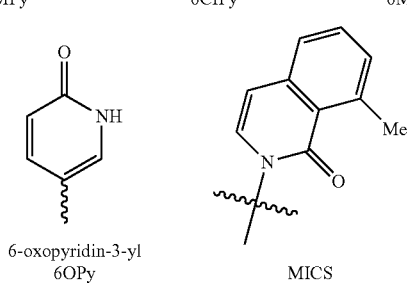
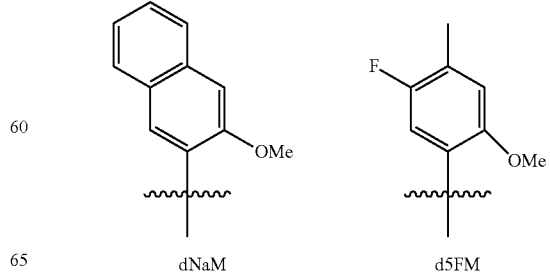

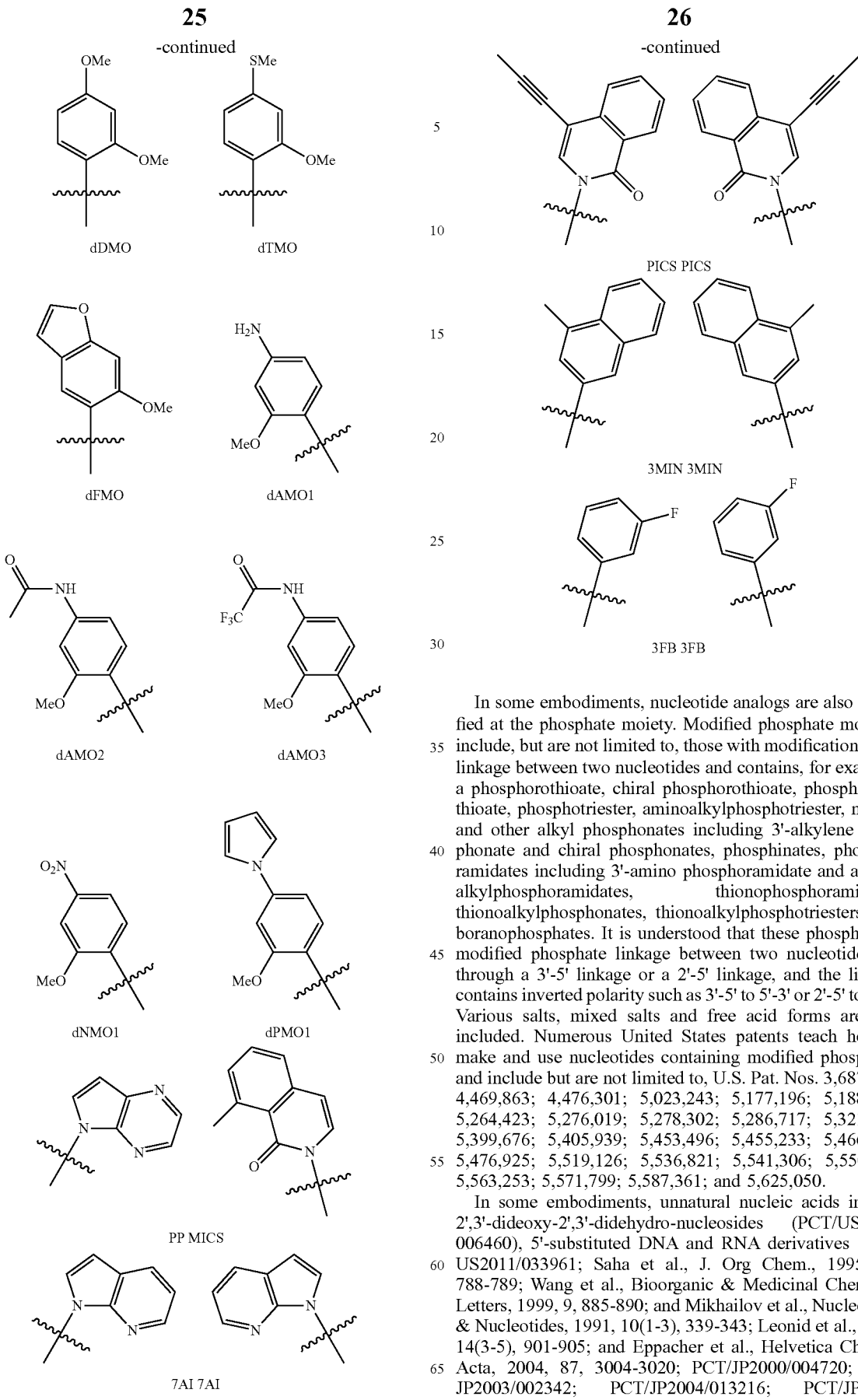

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, unnatural nucleic acids include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/

JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

In some embodiments, unnatural nucleic acids include modifications at the 5'-position and the 2'-position of the sugar ring (PCT/US94/02993), such as 5'-CH$_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers have been prepared for incorporation into oligonucleotides wherein the 3' linked nucleoside in the dimer (5' to 3') comprises a 2'-OCH$_3$ and a 5'-(S)—CH$_3$ (Mesmaeker et al., Synlett, 1997, 1287-1290). Unnatural nucleic acids can include 2'-substituted 5'-CH$_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group (SC(CH$_3$)$_3$) (and analogs thereof); a methyleneamino group (CH$_2$NH$_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substituent groups (including 5' and/or 2' substituent groups; bridging of two ring atoms to form bicyclic nucleic acids (BNA); replacement of the ribosyl ring oxygen atom with S, N(R), or C(R$_1$)(R$_2$) (R=H, C$_1$-C$_{12}$ alkyl or a protecting group); and combinations thereof. Examples of chemically modified sugars can be found in WO2008/101157, US2005/0130923, and WO2007/134181.

In some instances, a modified nucleic acid comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$, alkyl or C$_2$ to C$_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$ONH$_2$, and —O(CH$_2$)$_n$ON[(CH$_2$)$_n$CH$_3$)]$_2$, where n and m are from 1 to about 10.

Other modifications at the 2' position include but are not limited to: C$_1$ to C$_{10}$ lower alkyl, substituted lower alkyl, alkaryl, aralkyl, O-alkaryl, O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-OCH$_3$, and 2'-O(CH$_2$)$_2$OCH$_3$ substituent groups. The substituent at the 2' position can also be selected from allyl, amino, azido, thio, O-allyl, O—(C$_1$-C$_{10}$ alkyl), OCF$_3$, O(CH$_2$)$_2$SCH$_3$, O(CH$_2$)$_2$—O—

$N(R_m)(R_n)$, and $O-CH_2-C(=O)-N(R_m)(R_n)$, where each $R_m$ and $R_n$ is, independently, H or substituted or unsubstituted $C_1$-$C_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' and 4'-CH$(CH_2OCH_3)$—O-2', and analogs thereof (see, U.S. Pat. No. 7,399,845); 4'-$C(CH_3)(CH_3)$—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino ($-CH_2-N(CH_3)-O-CH_2-$), thiodiester ($-O-C(O)-S-$), thionocarbamate ($-O-C(O)(NH)-S-$); siloxane ($-O-Si(H)_2-O-$); and N,N*-dimethylhydrazine ($-CH_2-N(CH_3)-N(CH_3)$). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, N.Y.; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium l-di-O-hexadecyl-rac-glycero-S-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Nucleic Acid Base Pairing Properties

In some embodiments, an unnatural nucleic acid forms a base pair with another nucleic acid. In some embodiments, a stably integrated unnatural nucleic acid is an unnatural nucleic acid that can form a base pair with another nucleic acid, e.g., a natural or unnatural nucleic acid. In some embodiments, a stably integrated unnatural nucleic acid is an unnatural nucleic acid that can form a base pair with another unnatural nucleic acid (unnatural nucleic acid base pair (UBP)). For example, a first unnatural nucleic acid can form a base pair with a second unnatural nucleic acid. For example, one pair of unnatural nucleotide triphosphates that can base pair when incorporated into nucleic acids include a triphosphate of d5SICS (d5SICSTP) and a triphosphate of dNaM (dNaMTP). Such unnatural nucleotides can have a ribose or deoxyribose sugar moiety. In some embodiments, an unnatural nucleic acid does not substantially form a base pair with a natural nucleic acid (A, T, G, C). In some embodiments, a stably integrated unnatural nucleic acid can form a base pair with a natural nucleic acid.

In some embodiments, a stably integrated unnatural nucleic acid is an unnatural nucleic acid that can form a UBP, but does not substantially form a base pair with each of the four natural nucleic acids. In some embodiments, a stably integrated unnatural nucleic acid is an unnatural nucleic acid that can form a UBP, but does not substantially form a base pair with one or more natural nucleic acids. For example, a stably integrated unnatural nucleic acid may not substantially form a base pair with A, T, and, C, but can form a base pair with G. For example, a stably integrated unnatural nucleic acid may not substantially form a base pair with A, T, and, G, but can form a base pair with C. For example, a stably integrated unnatural nucleic acid may not substantially form a base pair with C, G, and, A, but can form a base pair with T. For example, a stably integrated unnatural nucleic acid may not substantially form a base pair with C, G, and, T, but can form a base pair with A. For example, a stably integrated unnatural nucleic acid may not substantially form a base pair with A and T, but can form a base pair with C and G. For example, a stably integrated unnatural nucleic acid may not substantially form a base pair with A and C, but can form a base pair with T and G. For example, a stably integrated unnatural nucleic acid may not substantially form a base pair with A and G, but can form a base pair with C and T. For example, a stably integrated unnatural nucleic acid may not substantially form a base pair with C and T, but can form a base pair with A and G. For example, a stably integrated unnatural nucleic acid may not substantially form a base pair with C and G, but can form a base pair with T and G. For example, a stably integrated unnatural nucleic acid may not substantially form a base pair with T and G, but can form a base pair with A and G. For example, a stably integrated unnatural nucleic acid may not substantially form a base pair with, G, but can form a base pair with A, T, and, C. For example, a stably integrated unnatural nucleic acid may not substantially form a base pair with, A, but can form a base pair with G, T, and, C. For example, a stably integrated unnatural nucleic acid may not substantially form a base pair with, T, but can form a base pair with G, A, and, C. For example, a stably integrated unnatural nucleic acid may not substantially form a base pair with, C, but can form a base pair with G, T, and, A.

Exemplary, unnatural nucleotides capable of forming an unnatural DNA or RNA base pair (UBP) under conditions in vivo includes, but is not limited to, 5SICS, d5SICS, NAM, dNaM, and combinations thereof. In some embodiments, unnatural nucleotides include:

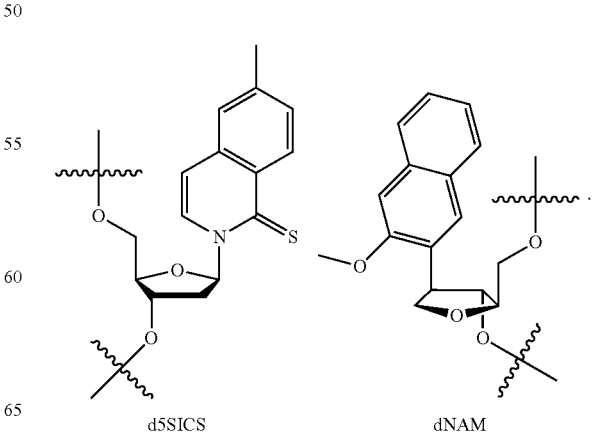

d5SICS          dNAM

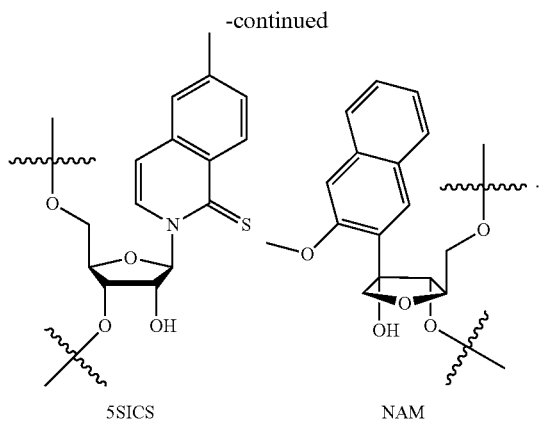

5SICS            NAM

Engineered Organism

In some embodiments, methods and plasmids disclosed herein is further used to generate engineered organism, e.g. an organism that incorporates and replicates an unnatural nucleotide or an unnatural nucleic acid base pair (UBP) with improved UBP retention and also transcribes and translates the nucleic acid containing the unnatural nucleotide or unnatural nucleic acid base pair into a protein containing an unnatural amino acid residue. In some instances, the organism is a semi-synthetic organism (SSO). In some instances, the SSO is a cell.

In some instances, the cell employed is genetically transformed with an expression cassette encoding a heterologous protein, e.g., a nucleotide triphosphate transporter capable of transporting unnatural nucleotide triphosphates into the cell, a CRISPR/Cas9 system to remove modifications at the unnatural nucleotide triphosphate positions, and/or a polymerase with high fidelity for an unnatural nucleic acid, so that the unnatural nucleotides are incorporated into cellular nucleic acids and e.g., form unnatural base pairs under in vivo conditions. In some instances, cells further comprise enhanced activity for unnatural nucleic acid uptake. In some cases, cells further comprise enhanced activity for unnatural nucleic acid import. In some cases, cells further comprise enhanced polymerase activity for unnatural nucleic acids.

In some embodiments, Cas9 and sgRNA are encoded on separate plasmids. In some instances, Cas9 and sgRNA are encoded on the same plasmid. In some cases, the nucleic acid molecule encoding Cas9, sgRNA, or a nucleic acid molecule comprising an unnatural nucleotide are located on one or more plasmids. In some instances, Cas9 is encoded on a first plasmid and the sgRNA and the nucleic acid molecule comprising an unnatural nucleotide are encoded on a second plasmid. In some instances, Cas9, sgRNA, and the nucleic acid molecule comprising an unnatural nucleotide are encoded on the same plasmid. In some instances, the nucleic acid molecule comprises two or more unnatural nucleotides.

In some instances, a first plasmid encoding Cas9 and sgRNA and a second plasmid encoding a nucleic acid molecule comprising an unnatural nucleotide are introduced into an engineered microorganism. In some instances, a first plasmid encoding Cas9 and a second plasmid encoding sgRNA and a nucleic acid molecule comprising an unnatural nucleotide are introduced into an engineered microorganism. In some instances, a plasmid encoding Cas9, sgRNA and a nucleic acid molecule comprising an unnatural nucleotide is introduced into an engineered microorganism. In some instances, the nucleic acid molecule comprises two or more unnatural nucleotides.

In some embodiments, a living cell is generated that incorporates within its nucleic acids at least one unnatural nucleotide and/or at least one unnatural base pair (UBP). In some instances, the unnatural base pair includes a pair of unnatural mutually base-pairing nucleotides capable of forming the unnatural base pair under in vivo conditions, when the unnatural mutually base-pairing nucleotides, as their respective triphosphates, are taken up into the cell by action of a nucleotide triphosphate transporter. The cell can be genetically transformed by an expression cassette encoding a nucleotide triphosphate transporter so that the nucleotide triphosphate transporter is expressed and is available to transport the unnatural nucleotides into the cell. The cell can be genetically transformed by an expression cassette encoding a polymerase so that the polymerase is expressed and is available to incorporate unnatural nucleotides into the cell's nucleic acids. The cell can be a prokaryotic or eukaryotic cell, and the pair of unnatural mutually base-pairing nucleotides, as their respective triphosphates, can be a triphosphate of d5SICS (d5SICSTP) and a triphosphate of dNaM (dNaMTP).

In some embodiments, cells are genetically transformed cells with a nucleic acid, e.g., an expression cassette encoding a nucleotide triphosphate transporter capable of transporting such unnatural nucleotides into the cell. A cell can comprise a heterologous nucleotide triphosphate transporter, where the heterologous nucleotide triphosphate transporter can transport natural and unnatural nucleotide triphosphates into the cell. A cell can comprise a heterologous polymerase, where the heterologous polymerase has activity for an unnatural nucleic acid.

In some cases, a method described herein also include contacting a genetically transformed cell with the respective triphosphate forms unnatural nucleotides, in the presence of potassium phosphate and/or an inhibitor of phosphatases or nucleotidases. During or after such contact, the cell can be placed within a life-supporting medium suitable for growth and replication of the cell. The cell can be maintained in the life-supporting medium so that the respective triphosphate forms of unnatural nucleotides are incorporated into nucleic acids within the cells, and through at least one replication cycle of the cell. The pair of unnatural mutually base-pairing nucleotides as a respective triphosphate, can comprise a triphosphate of d5SICS (d5SICSTP) and a triphosphate of dNaM (dNaMTP), the cell can be E. coli, and the d5SICSTP and dNaMTP can be efficiently imported into E. coli by the transporter PtNTT2, wherein an E. coli polymerase, such as Pol I, can efficiently use the unnatural triphosphates to replicate DNA, thereby incorporating unnatural nucleotides and/or unnatural base pairs into cellular nucleic acids within the cellular environment.

By practice of a method of the invention, the person of ordinary skill can obtain a population of a living and propagating cells that has at least one unnatural nucleotide and/or at least one unnatural base pair (UBP) within at least one nucleic acid maintained within at least some of the individual cells, wherein the at least one nucleic acid is stably propagated within the cell, and wherein the cell expresses a nucleotide triphosphate transporter suitable for providing cellular uptake of triphosphate forms of one or more unnatural nucleotides when contacted with (e.g., grown in the presence of) the unnatural nucleotide(s) in a life-supporting medium suitable for growth and replication of the organism.

After transport into the cell by the nucleotide triphosphate transporter, the unnatural base-pairing nucleotides are incorporated into nucleic acids within the cell by cellular machinery, e.g., the cell's own DNA and/or RNA polymerases, a heterologous polymerase, or a polymerase that has been evolved using directed evolution (Chen T, Romesberg F E, FEBS Lett. 2014 Jan. 21; 588(2):219-29; Betz K et al., J Am Chem Soc. 2013 Dec. 11; 135(49):18637-43). The unnatural nucleotides can be incorporated into cellular nucleic acids such as genomic DNA, genomic RNA, mRNA, structural RNA, microRNA, and autonomously replicating nucleic acids (e.g., plasmids, viruses, or vectors).

In some cases, genetically engineered cells are generated by introduction of nucleic acids, e.g., heterologous nucleic acids, into cells. Any cell described herein can be a host cell and can comprise an expression vector. In one embodiment, the host cell is a prokaryotic cell. In another embodiment, the host cell is E. coli. In some embodiments, a cell comprises one or more heterologous polynucleotides. Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances the addition of carrier molecules (e.g., bis-benzimdazolyl compounds, for example, see U.S. Pat. No. 5,595, 899) can increase the uptake of DNA in cells typically though to be difficult to transform by conventional methods. Conventional methods of transformation are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

In some instances, genetic transformation is obtained using direct transfer of an expression cassette, in but not limited to, plasmids, viral vectors, viral nucleic acids, phage nucleic acids, phages, cosmids, and artificial chromosomes, or via transfer of genetic material in cells or carriers such as cationic liposomes. Such methods are available in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991).

For example, a nucleotide triphosphate transporter or polymerase nucleic acid molecule, expression cassette and/ or vector can be introduced to a cell by any method including, but not limited to, calcium-mediated transformation, electroporation, microinjection, lipofection, particle bombardment and the like.

In some cases, a cell comprises unnatural nucleotide triphosphates incorporated into one or more nucleic acids within the cell. For example, the cell can be a living cell capable of incorporating at least one unnatural nucleotide within DNA or RNA maintained within the cell. The cell can also incorporate at least one unnatural base pair (UBP) comprising a pair of unnatural mutually base-pairing nucleotides into nucleic acids within the cell under in vivo conditions, wherein the unnatural mutually base-pairing nucleotides, e.g., their respective triphosphates, are taken up by the cell by action of a nucleotide triphosphate transporter, the gene for which is present (e.g., was introduced) into the cell by genetic transformation. For example, upon incorporation into the nucleic acid maintained within s cell, d5SICS and dNaM can form a stable unnatural base pair that can be stably propagated by the DNA replication machinery of an organism, e.g., when grown in a life-supporting medium comprising d5SICS and dNaM.

In some cases, cells are capable of replicating an unnatural nucleic acid. Such methods can include genetically transforming the cell with an expression cassette encoding a nucleotide triphosphate transporter capable of transporting into the cell, as a respective triphosphate, one or more unnatural nucleotides under in vivo conditions. Alternatively, a cell can be employed that has previously been genetically transformed with an expression cassette that can express an encoded nucleotide triphosphate transporter. The method can also include contacting or exposing the genetically transformed cell to potassium phosphate and the respective triphosphate forms of at least one unnatural nucleotide (for example, two mutually base-pairing nucleotides capable of forming the unnatural base pair (UBP)) in a life-supporting medium suitable for growth and replication of the cell, and maintaining the transformed cell in the life-supporting medium in the presence of the respective triphosphate forms of at least one unnatural nucleotide (for example, two mutually base-pairing nucleotides capable of forming the unnatural base pair (UBP)) under in vivo conditions, through at least one replication cycle of the cell.

In some embodiments, a cell comprises a stably incorporated unnatural nucleic acid. Some embodiments comprise a cell (e.g., as E. coli) that stably incorporates nucleotides other than A, G, T, and C within nucleic acids maintained within the cell. For example, the nucleotides other than A, G, T, and C can be d5SICS and dNaM, which upon incorporation into nucleic acids of the cell, can form a stable unnatural base pair within the nucleic acids. In one aspect, unnatural nucleotides and unnatural base pairs can be stably propagated by the replication apparatus of the organism, when an organism transformed with the gene for the triphosphate transporter, is grown in a life-supporting medium that includes potassium phosphate and the triphosphate forms of d5SICS and dNaM.

In some cases, a cell comprises an expanded genetic alphabet. A cell can comprise a stably incorporated unnatural nucleic acid. In some embodiments, a cell with an expanded genetic alphabet comprises an unnatural nucleic acid that can form a base pair (bp) with another nucleic acid, e.g., a natural or unnatural nucleic acid. In some embodiments, a cell with an expanded genetic alphabet comprises an unnatural nucleic acid that is hydrogen bonded to another nucleic acid. In some embodiments, a cell with an expanded genetic alphabet comprises an unnatural nucleic acid that is not hydrogen bonded to another nucleic acid to which it is base paired. In some embodiments, a cell with an expanded genetic alphabet comprises an unnatural nucleic acid that base pairs to another nucleic acid via hydrophobic interactions. In some embodiments, a cell with an expanded genetic alphabet comprises an unnatural nucleic acid that base pairs to another nucleic acid via non-hydrogen bonding interactions. A cell with an expanded genetic alphabet can be a cell that can copy a homologous nucleic acid to form a nucleic acid comprising an unnatural nucleic acid. A cell with an expanded genetic alphabet can be a cell comprising an unnatural nucleic acid base paired with another unnatural nucleic acid (unnatural nucleic acid base pair (UBP)).

In some embodiments, cells form unnatural DNA base pairs (UBPs) from the imported unnatural nucleotides under in vivo conditions. In some embodiments potassium phosphate and/or inhibitors of phosphatase and/or nucleotidase activities can facilitate transport of unnatural nucleic acids. The methods include use of a cell that expresses a heterologous nucleotide triphosphate transporter. When such a cell is contacted with one or more nucleotide triphosphates, the nucleotide triphosphates are transported into the cell. The cell can be in the presence of potassium phosphate and/or inhibitors of phosphatase and nucleotidase. Unnatural nucleotide triphosphates can be incorporated into nucleic acids within the cell by the cell's natural machinery and, for example, can mutually base-pair to form unnatural base pairs within the nucleic acids of the cell.

In some embodiments, a UBP can be incorporated into a cell or population of cells when exposed to unnatural triphosphates. In some embodiments a UBP can be incorporated into a cell or population of cells when substantially consistently exposed to unnatural triphosphates. In some embodiments, replication of a UBP does not result in a substantially reduced growth rate. In some embodiments, replication expression of a heterologous protein, e.g., a nucleotide triphosphate transport does not result in a substantially reduced growth rate.

In some embodiments, induction of expression of a heterologous gene, e.g., an NTT, in a cell can result in slower cell growth and increased unnatural nucleic acid uptake compared to the growth and uptake of a cell without induction of expression of the heterologous gene. In some embodiments, induction of expression of a heterologous gene, e.g., an NTT, in a cell can result in increased cell growth and increased unnatural nucleic acid uptake compared to the growth and uptake of a cell without induction of expression of the heterologous gene.

In some embodiments, a UBP is incorporated during a log growth phase. In some embodiments, a UBP is incorporated during a non-log growth phase. In some embodiments, a UBP is incorporated during a substantially linear growth phase. In some embodiments a UBP is stably incorporated into a cell or population of cells after growth for a time period. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 or more duplications. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, or 24 hours of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days of growth. For example, a UBP can be stably incorporated into a cell or population of cells after growth for at least about 1, 2, 3, 4, 5, 6 7, 8, 9, 10, 11, or 12 months of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50 years of growth.

In some embodiments, a cell further utilizes a polymerase described herein to generate a mutant mRNA which contains a mutant codon that comprises one or more unnatural nucleic acid base. In some instances, a cell further utilizes a polymerase disclosed herein to generate a mutant tRNA which contains a mutant anticodon that comprises one or more unnatural nucleic acid base. In some instances, the mutant anticodon represents an unnatural amino acid. In some instances, the anticodon of the mutant tRNA pairs with the codon of the mutant mRNA during translation to synthesis a protein that contains an unnatural amino acid.

As used herein, an amino acid residue can refer to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes, without limitation, α-amino acids, natural amino acids, non-natural amino acids, and amino acid analogs.

The term "α-amino acid" can refer to a molecule containing both an amino group and a carboxyl group bound to a carbon which is designated the α-carbon.

The term "β-amino acid" can refer to a molecule containing both an amino group and a carboxyl group in a β configuration.

"Naturally occurring amino acid" can refer to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive(10%) neutral(90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acid" can be glycine, alanine, proline, and analogs thereof "Large hydrophobic amino acids" can be valine, leucine, isoleucine, phenylalanine, methionine, tryptophan, and analogs thereof "Polar amino acids" can be serine, threonine, asparagine, glutamine, cysteine, tyrosine, and analogs thereof "Charged amino acids" can be lysine, arginine, histidine, aspartate, glutamate, and analogs thereof.

An "amino acid analog" can be a molecule which is structurally similar to an amino acid and which can be substituted for an amino acid in the formation of a peptidomimetic macrocycle Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

A "non-natural amino acid" can be an amino acid which is not one of the twenty amino acids commonly found in peptides synthesized in nature, and known by the one letter abbreviations A, R, N, C, D, Q, E, G, H, I, L, K, M, F, P, S, T, W, Y and V.

Amino acid analogs can include β-amino acid analogs. Examples of β-amino acid analogs include, but are not limited to, the following: cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl) butyric acid; (S)-3-amino-4-(4-cyanophenyl)-butyric acid; (S)-3-amino-4-(4-fluorophenyl) butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; homoaspartic acid γ-benzyl ester; L-β-homoglutamic acid 6-benzyl ester; L-β-homoisoleucine; L-β-homoleucine; L-β-homomethionine; L-β-homophenylalanine; L-β-homoproline; homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Amino acid analogs can include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; 13-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanin; β-cyclohexyl-D-alanine; β-cyclohexyl-L-alanine; β-cyclopenten-1-yl-alanine; β-cyclopentyl-alanine; β-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH.dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH.dicyclohexylammonium salt; cyclopentyl-Gly-OH.dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine-dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl)glycine; L-2-amino-3-(dimethylamino)-propionic acid; L-2-aminocaproic acid dicyclohexyl-ammonium salt; L-2-indanylglycine; L-allylglycine.dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid;

(N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogs can include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; Lys(Me)$_2$-OH; Lys(N$_3$)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxo-cyclohex-1-ylidene)ethyl)-D-ornithine; (Nδ-1-(4,4-dimethyl-2,6-dioxo-cyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg(Me)$_2$-OH (asymmetrical); Arg(Me)$_2$-OH (symmetrical); Lys(ivDde)-OH; Lys(Me)$_2$-OH·HCl; Lys(Me3)-OH chloride; Nω-nitro-D-arginine; and Nω-nitro-L-arginine.

Amino acid analogs can include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

Amino acid analogs can include analogs of cysteine and methionine. Examples of amino acid analogs of cysteine and methionine include, but are not limited to, Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridypethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

Amino acid analogs can include analogs of phenylalanine and tyrosine. Examples of amino acid analogs of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2;4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl) amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Amino acid analogs can include analogs of proline. Examples of amino acid analogs of proline include, but are not limited to, 3,4-dehydro-proline, 4-fluoro-proline, cis-4-hydroxy-proline, thiazolidine-2-carboxylic acid, and trans-4-fluoro-proline.

Amino acid analogs can include analogs of serine and threonine. Examples of amino acid analogs of serine and threonine include, but are not limited to, 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Amino acid analogs can include analogs of tryptophan. Examples of amino acid analogs of tryptophan include, but are not limited to, the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

Amino acid analogs can be racemic. In some instances, the D isomer of the amino acid analog is used. In some cases, the L isomer of the amino acid analog is used. In some instances, the amino acid analog comprises chiral centers that are in the R or S configuration. Sometimes, the amino group(s) of a β-amino acid analog is substituted with a protecting group, e.g., tert-butyloxycarbonyl (BOC group), 9-fluorenylmethyloxycarbonyl (FMOC), tosyl, and the like. Sometimes, the carboxylic acid functional group of a β-amino acid analog is protected, e.g., as its ester derivative. In some cases, the salt of the amino acid analog is used.

In some embodiments, an unnatural amino acid is an unnatural amino acid described in Liu C. C., Schultz, P. G. Annu. Rev. Biochem. 2010, 79, 413.

Cell Types

In some embodiments, many types of cells/microorganisms are used, e.g., for transforming or genetically engineering. In some embodiments, a cell is a prokaryotic or eukaryotic cell. In some cases, the cell is a microorganism such as a bacterial cell, fungal cell, yeast, or unicellular protozoan. In other cases, the cell is a eukaryotic cell, such as a cultured animal, plant, or human cell. In additional cases, the cell is present in an organism such as a plant or animal.

In some embodiments, an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba). In some embodiments, an engineered microorganism is a fungus. In some embodiments, an engineered organism is a yeast.

Any suitable yeast may be selected as a host microorganism, engineered microorganism, genetically modified organism or source for a heterologous or modified polynucleotide. Yeast include, but are not limited to, *Yarrowia* yeast (e.g., *Y. lipolytica* (formerly classified as *Candida lipolytica*)), *Candida* yeast (e.g., *C. revkaufi, C. viswanathii, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris*) and *Lipomyces* yeast (e.g., *L. starkeyii, L. lipoferus*). In some embodiments, a suitable yeast is of the genus *Arachniotus, Aspergillus, Aureobasidium, Auxarthron, Blastomyces, Candida, Chrysosporuim, Chrysosporuim Debaryomyces, Coccidiodes, Cryptococcus, Gymnoascus, Hansenula, Histoplasma, Issatchenkia, Kluyveromyces, Lipomyces, Lssatchenkia, Microsporum, Myxotrichum, Myxozyma, Oidiodendron, Pachysolen, Penicillium, Pichia, Rhodosporidium, Rhodotorula, Rhodotorula, Saccharomyces, Schizosaccharomyces, Scopulariopsis, Sepedonium, Trichosporon,* or *Yarrowia*. In some embodiments, a suitable yeast is of the species *Arachniotus flavoluteus, Aspergillus flavus, Aspergillus fumigatus, Aspergillus niger, Aureobasidium pullulans, Auxarthron thaxteri, Blastomyces dermatitidis, Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii, Chrysosporuim keratinophilum, Coccidiodes immitis, Cryptococcus albidus* var. *diffluens, Cryptococcus laurentii, Cryptococcus neofomans, Debaryomyces hansenii, Gymnoascus dugwayensis, Hansenula anomala, Histoplasma capsulatum, Issatchenkia occidentalis, Isstachenkia orientalis, Kluyveromyces lactis, Kluyveromyces marxianus, Kluyveromyces thermotolerans, Kluyveromyces waltii, Lipomyces lipoferus, Lipomyces starkeyii, Microsporum gypseum, Myxotrichum deflexum, Oidiodendron echinulatum, Pachysolen tannophilis, Penicillium notatum, Pichia anomala, Pichia pastoris, Pichia stipitis, Rhodosporidium toruloides, Rhodotorula glutinus, Rhodotorula graminis, Saccharomyces cerevisiae, Saccharomyces kluyveri, Schizosaccharomyces pombe, Scopulariopsis acremonium, Sepedonium chrysospermum, Trichosporon cutaneum, Trichosporon pullans, Yarrowia lipolytica,* or *Yarrowia lipolytica* (formerly classified as *Candida lipolytica*). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *Candida* species (i.e., *Candida* spp.) yeast. Any suitable *Candida* species can be used and/or genetically modified for production of a fatty dicarboxylic acid (e.g., octanedioic acid, decanedioic acid, dodecanedioic acid, tetradecanedioic acid, hexadecanedioic acid, octadecanedioic acid, eicosanedioic acid). In some embodiments, suitable *Candida* species include, but are not limited to *Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii* and any other *Candida* spp. yeast described herein. Non-limiting examples of *Candida* spp. strains include, but are not limited to, sAA001 (ATCC20336), sAA002 (ATCC20913), sAA003 (ATCC20962), sAA496 (US2012/0077252), sAA106 (US2012/0077252), SU-2 (ura3-/ura3-), H5343 (beta oxidation blocked; U.S. Pat. No. 5,648,247) strains. Any suitable strains from *Candida* spp. yeast may be utilized as parental strains for genetic modification.

Yeast genera, species and strains are often so closely related in genetic content that they can be difficult to distinguish, classify and/or name. In some cases strains of *C. lipolytica* and *Y. lipolytica* can be difficult to distinguish, classify and/or name and can be, in some cases, considered the same organism. In some cases, various strains of *C. tropicalis* and *C. viswanathii* can be difficult to distinguish, classify and/or name (for example see Arie et. al., J. Gen. Appl. Microbiol., 46, 257-262 (2000). Some *C. tropicalis* and *C. viswanathii* strains obtained from ATCC as well as from other commercial or academic sources can be considered equivalent and equally suitable for the embodiments described herein. In some embodiments, some parental strains of *C. tropicalis* and *C. viswanathii* are considered to differ in name only.

Any suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), *Thraustochytrium* fungi, *Schizochytrium* fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), *Acinetobacter* bacteria, *Norcardia* baceteria, *Xanthobacter* bacteria, *Escherichia* bacteria (e.g., *E. coli* (e.g., strains DH10B, Stb12, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Megasphaera* bacteria (e.g., *Megasphaera elsdenii*). Bacteria also include, but are not limited to, photosynthetic bacteria (e.g., green non-sulfur bacteria (e.g., *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*)).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; mammalian cells (e.g., NIH3T3, 293, CHO, COS, VERO, C127, BHK, Per-C6, Bowes melanoma and HeLa cells); and plant cells (e.g., *Arabidopsis thaliana, Nicotania tabacum, Cuphea acinifolia, Cuphea aequipetala, Cuphea angustifolia, Cuphea appendiculata, Cuphea avigera, Cuphea avigera* var. *pulcherrima, Cuphea axilliflora, Cuphea bahiensis, Cuphea baillonis, Cuphea brachypoda, Cuphea bustamanta, Cuphea calcarata, Cuphea calophylla, Cuphea calophylla* subsp. *mesostemon, Cuphea carthagenensis, Cuphea circaeoides, Cuphea confertiflora, Cuphea cordata, Cuphea crassiflora, Cuphea cyanea, Cuphea decandra, Cuphea denticulata, Cuphea disperma, Cuphea epilobiifolia, Cuphea ericoides, Cuphea flava, Cuphea flavisetula, Cuphea fuchsiifolia, Cuphea gaumeri, Cuphea glutinosa, Cuphea heterophylla, Cuphea hookeriana, Cuphea hyssopifolia* (Mexican-heather), *Cuphea hyssopoides, Cuphea ignea, Cuphea ingrata, Cuphea jorullensis, Cuphea lanceolata, Cuphea linarioides, Cuphea llavea, Cuphea lophostoma, Cuphea lutea, Cuphea lutescens, Cuphea melanium, Cuphea melvilla, Cuphea micrantha, Cuphea micropetala, Cuphea mimuloides, Cuphea nitidula, Cuphea palustris, Cuphea parsonsia, Cuphea pascuorum, Cuphea paucipetala, Cuphea procumbens, Cuphea pseudosilene, Cuphea pseudovaccinium, Cuphea pulchra, Cuphea racemosa, Cuphea repens, Cuphea salicifolia, Cuphea salvadorensis, Cuphea schumannii, Cuphea sessiliflora, Cuphea sessilifolia, Cuphea setosa, Cuphea spectabilis, Cuphea spermacoce, Cuphea splendida, Cuphea splendida* var. *viridiflava, Cuphea strigulosa, Cuphea subuligera, Cuphea teleandra, Cuphea thymoides, Cuphea tolucana, Cuphea urens, Cuphea utriculosa, Cuphea viscosissima, Cuphea watsoniana, Cuphea wrightii, Cuphea lanceolata*).

Microorganisms or cells used as host organisms or source for a heterologous polynucleotide are commercially available. Microorganisms and cells described herein, and other suitable microorganisms and cells are available, for example, from Invitrogen Corporation, (Carlsbad, Calif.), American Type Culture Collection (Manassas, Va.), and Agricultural Research Culture Collection (NRRL; Peoria, Ill.). Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Polymerase

A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases.

The ability to improve specificity, processivity, or other features of polymerases unnatural nucleic acids would be highly desirable in a variety of contexts where, e.g., unnatural nucleic acid incorporation is desired, including amplification, sequencing, labeling, detection, cloning, and many others. The present invention provides polymerases with modified properties for unnatural nucleic acids, methods of making such polymerases, methods of using such polymerases, and many other features that will become apparent upon a complete review of the following.

In some instances, disclosed herein includes polymerases that incorporate unnatural nucleic acids into a growing template copy, e.g., during DNA amplification. In some embodiments, polymerases can be modified such that the active site of the polymerase is modified to reduce steric entry inhibition of the unnatural nucleic acid into the active site. In some embodiments, polymerases can be modified to provide complementarity with one or more unnatural features of the unnatural nucleic acids. Such polymerases can be expressed or engineered in cells for stably incorporating a UBP into the cells. Accordingly, the invention includes compositions that include a heterologous or recombinant polymerase and methods of use thereof Polymerases can be modified using methods pertaining to protein engineering. For example, molecular modeling can be carried out based on crystal structures to identify the locations of the polymerases where mutations can be made to modify a target activity. A residue identified as a target for replacement can be replaced with a residue selected using energy minimization modeling, homology modeling, and/or conservative amino acid substitutions, such as described in Bordo, et al. J Mol Biol 217: 721-729 (1991) and Hayes, et al. Proc Natl Acad Sci, USA 99: 15926-15931 (2002).

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. In some embodiments, a polymerase is a wild type polymerase. In some embodiments, a polymerase is a modified, or mutant, polymerase.

Polymerases, with features for improving entry of unnatural nucleic acids into active site regions and for coordinating with unnatural nucleotides in the active site region, can also be used. In some embodiments, a modified polymerase has a modified nucleotide binding site.

In some embodiments, a modified polymerase has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid. In some embodiments, a modified or wild type polymerase has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified sugar. In some embodiments, a modified or wild type polymerase has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward a nucleic acid comprising a triphosphate and/or the unnatural nucleic acid without the triphosphate. For example, a modified or wild type polymerase can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid with a diphosphate or monophosphate, or no phosphate, or a combination thereof.

In some embodiments, a modified or wild type polymerase has a relaxed specificity for an unnatural nucleic acid. In some embodiments, a modified or wild type polymerase has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid.

Absence of exonuclease activity can be a wild type characteristic or a characteristic imparted by a variant or engineered polymerase. For example, an exo minus Klenow fragment is a mutated version of Klenow fragment that lacks 3' to 5' proofreading exonuclease activity.

The method of the invention may be used to expand the substrate range of any DNA polymerase which lacks an intrinsic 3 to 5' exonuclease proofreading activity or where a 3 to 5' exonuclease proofreading activity has been disabled, e.g. through mutation. Examples of DNA polymerases include polA, polB (see e.g. Parrel & Loeb, Nature Struc Biol 2001) polC, polD, polY, polX and reverse transcriptases (RT) but preferably are processive, high-fidelity polymerases (PCT/GB2004/004643). In some embodiments a modified or wild type polymerase substantially lacks 3' to 5' proofreading exonuclease activity. In some embodiments a modified or wild type polymerase substantially lacks 3' to 5' proofreading exonuclease activity for an unnatural nucleic acid. In some embodiments, a modified or wild type polymerase has a 3' to 5' proofreading exonuclease activity. In some embodiments, a modified or wild type polymerase has a 3' to 5' proofreading exonuclease activity for a natural nucleic acid and substantially lacks 3' to 5' proofreading exonuclease activity for an unnatural nucleic acid.

In some embodiments, a modified polymerase has a 3' to 5' proofreading exonuclease activity that is at least about 60%, 70%, 80%, 90%, 95%, 97%, 98%, 99%, 99.5%, 99.99% the proofreading exonuclease activity of the wild type polymerase. In some embodiments, a modified polymerase has a 3' to 5' proofreading exonuclease activity for an unnatural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for an unnatural nucleic acid and a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to the natural nucleic acid.

In some embodiments, polymerases are characterized according to their rate of dissociation from nucleic acids. In some embodiments a polymerase has a relatively low dissociation rate for one or more natural and unnatural nucleic acids. In some embodiments a polymerase has a relatively high dissociation rate for one or more natural and unnatural nucleic acids. The dissociation rate is an activity of a polymerase that can be adjusted to tune reaction rates in methods set forth herein.

In some embodiments, polymerases are characterized according to their fidelity when used with a particular natural and/or unnatural nucleic acid or collections of natural and/or unnatural nucleic acid. Fidelity generally refers to the accuracy with which a polymerase incorporates correct nucleic acids into a growing nucleic acid chain when making a copy of a nucleic acid template. DNA polymerase fidelity can be measured as the ratio of correct to incorrect natural and unnatural nucleic acid incorporations when the natural and unnatural nucleic acid are present, e.g., at equal concentrations, to compete for strand synthesis at the same site in the polymerase-strand-template nucleic acid binary complex. DNA polymerase fidelity can be calculated as the ratio of $(k_{cat}/K_m)$ for the natural and unnatural nucleic acid and $(k_{cat}/K_m)$ for the incorrect natural and unnatural nucleic acid; where $k_{cat}$ and $K_m$ are Michaelis-Menten parameters in steady state enzyme kinetics (Fersht, A. R. (1985) Enzyme Structure and Mechanism, 2nd ed., p 350, W. H. Freeman & Co., New York., incorporated herein by reference). In some embodiments, a polymerase has a fidelity value of at least about 100, 1000, 10,000, 100,000, or $1\times10^6$, with or without a proofreading activity.

In some embodiments, polymerases from native sources or variants thereof are screened using an assay that detects incorporation of an unnatural nucleic acid having a particular structure. In one example, polymerases can be screened for the ability to incorporate an unnatural nucleic acid or UBP; e.g., d5SICSTP, dNaMTP, or d5SICSTP-dNaMTP UBP. A polymerase, e.g., a heterologous polymerase, can be used that displays a modified property for the unnatural nucleic acid as compared to the wild-type polymerase. For example, the modified property can be, e.g., $K_m$, $k_{cat}$, $V_{max}$, polymerase processivity in the presence of an unnatural nucleic acid (or of a naturally occurring nucleotide), average template read-length by the polymerase in the presence of an unnatural nucleic acid, specificity of the polymerase for an unnatural nucleic acid, rate of binding of an unnatural nucleic acid, rate of product (pyrophosphate, triphosphate, etc.) release, branching rate, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the polymerase optionally has an increased rate of binding of an unnatural nucleic acid, an increased rate of product release, and/or a decreased branching rate, as compared to a wild-type polymerase.

At the same time, a polymerase can incorporate natural nucleic acids, e.g., A, C, G, and T, into a growing nucleic acid copy. For example, a polymerase optionally displays a specific activity for a natural nucleic acid that is at least about 5% as high (e.g., 5%, 10%, 25%, 50%, 75%, 100% or higher), as a corresponding wild-type polymerase and a processivity with natural nucleic acids in the presence of a template that is at least 5% as high (e.g., 5%, 10%, 25%, 50%, 75%, 100% or higher) as the wild-type polymerase in the presence of the natural nucleic acid. Optionally, the polymerase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type polymerase.

Polymerases used herein that can have the ability to incorporate an unnatural nucleic acid of a particular structure can also be produced using a directed evolution approach. A nucleic acid synthesis assay can be used to screen for polymerase variants having specificity for any of a variety of unnatural nucleic acids. For example, polymerase variants can be screened for the ability to incorporate an unnatural nucleic acid or UBP; e.g., d5SICSTP, dNaMTP, or d5SICSTP-dNaMTP UBP into nucleic acids. In some embodiments, such an assay is an in vitro assay, e.g., using a recombinant polymerase variant. In some embodiments, such an assay is an in vivo assay, e.g., expressing a polymerase variant in a cell. Such directed evolution techniques can be used to screen variants of any suitable polymerase for activity toward any of the unnatural nucleic acids set forth herein.

Modified polymerases of the compositions described can optionally be a modified and/or recombinant Φ29-type DNA polymerase. Optionally, the polymerase can be a modified and/or recombinant Φ29, B103, GA-1, PZA, Φ15, BS32, M2Y, Nf, Gl, Cp-1, PRD1, PZE, SFS, Cp-5, Cp-7, PR4, PR5, PR722, or L17 polymerase.

Nucleic acid polymerases generally useful in the invention include DNA polymerases, RNA polymerases, reverse transcriptases, and mutant or altered forms thereof. DNA polymerases and their properties are described in detail in, among other places, DNA Replication 2$^{nd}$ edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermo-* *coccus litoralis* (Tli) DNA polymerase (also referred to as Vent™ DNA polymerase, Cariello et al, 1991, Polynucleotides Res, 19: 4193, New England Biolabs), 9° Nm™ DNA polymerase (New England Biolabs), Stoffel fragment, Thermo Sequenase® (Amersham Pharmacia Biotech UK), Terminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al, 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus* gorgonarius, Roche Molecular Biochemicals), *E. coli* DNA polymerase I (Lecomte and Doubleday, 1983, Polynucleotides Res. 11:7505), T7 DNA polymerase (Nordstrom et al, 1981, J Biol. Chem. 256:3112), and archaeal DP1I/DP2 DNA polymerase II (Cann et al, 1998, Proc. Natl. Acad. Sci. USA 95:14250). Both mesophilic polymerases and thermophilic polymerases are contemplated. Thermophilic DNA polymerases include, but are not limited to, ThermoSequenase®, 9° Nm™, Terminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A polymerase that is a 3 exonuclease-deficient mutant is also contemplated. Reverse transcriptases useful in the invention include, but are not limited to, reverse transcriptases from HIV, HTLV-I, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al, CRC Crit Rev Biochem. 3:289-347(1975)). Further examples of polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase Gardner et al. (2004) "Comparative Kinetics of Nucleotide Analog Incorporation by Vent DNA Polymerase (J. Biol. Chem., 279(12), 11834-11842; Gardner and Jack "Determinants of nucleotide sugar recognition in an archaeon DNA polymerase" Nucleic Acids Research, 27(12) 2545-2553.) Polymerases isolated from non-thermophilic organisms can be heat inactivatable. Examples are DNA polymerases from phage. It will be understood that polymerases from any of a variety of sources can be modified to increase or decrease their tolerance to high temperature conditions. In some embodiments, a polymerase can be thermophilic. In some embodiments, a thermophilic polymerase can be heat inactivatable. Thermophilic polymerases are typically useful for high temperature conditions or in thermocycling conditions such as those employed for polymerase chain reaction (PCR) techniques.

In some embodiments, the polymerase comprises D29, B103, GA-1, PZA, 015, BS32, M2Y, Nf, Gl, Cp-1, PRD1, PZE, SFS, Cp-5, Cp-7, PR4, PR5, PR722, L17, ThermoSequenase®, 9° Nm™, Terminator™ DNA polymerase, Tne, Tma, Tfl, Tth, Tli, Stoffel fragment, Vent™ and Deep Vent™ DNA polymerase, KOD DNA polymerase, Tgo, JDF-3, Pfu, Taq, T7 DNA polymerase, T7 RNA polymerase, PGB-D, UlTma DNA polymerase, *E. coli* DNA polymerase I, *E. coli* DNA polymerase III, archaeal DP1I/DP2 DNA polymerase II, 9° N DNA Polymerase, Taq DNA polymerase, Phusion® DNA polymerase, Pfu DNA polymerase, SP6 RNA polymerase, RB69 DNA polymerase, Avian Myeloblastosis Virus (AMV) reverse transcriptase, Moloney Murine Leukemia Virus (MMLV) reverse transcriptase, SuperScript® II reverse transcriptase, and SuperScript® III reverse transcriptase.

In some embodiments, the polymerase is DNA polymerase 1-Klenow fragment, Vent polymerase, Phusion® DNA polymerase, KOD DNA polymerase, Taq polymerase, T7 DNA polymerase, T7 RNA polymerase, Therminator™ DNA polymerase, POLB polymerase, SP6 RNA polymerase, E. coli DNA polymerase I, E. coli DNA polymerase III, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase.

Additionally, such polymerases can be used for DNA amplification and/or sequencing applications, including real-time applications, e.g., in the context of amplification or sequencing that include incorporation of unnatural nucleic acid residues into DNA by the polymerase. In other embodiments, the unnatural nucleic acid that is incorporated can be the same as a natural residue, e.g., where a label or other moiety of the unnatural nucleic acid is removed by action of the polymerase during incorporation, or the unnatural nucleic acid can have one or more feature that distinguishes it from a natural nucleic acid.

Nucleotide Transporter

Nucleotide transporters (NTs) are a group of membrane transport proteins that facilitate nucleoside substrates across cell membranes and vesicles. In some embodiments, there are two types of nucleoside transporters, concentrative nucleoside transporters and equilibrative nucleoside transporters. In some instances, NTs also encompass the organic anion transporters (OAT) and the organic cation transporters (OCT). In some instances, nucleotide transporter is a nucleotide triphosphate transporter.

In some embodiments, a nucleotide triphosphate transporter (NTT) is from bacteria, plant, or algae. In some embodiments, a nucleotide triphosphate transporter is TpNTT1, TpNTT2, TpNTT3, TpNTT4, TpNTT5, TpNTT6, TpNTT7, TpNTT8 (*T. pseudonana*), PtNTT1, PtNTT2, PtNTT3, PtNTT4, PtNTT5, PtNTT6 (*P. tricornutum*), GsNTT (*Galdieria sulphuraria*), AtNTT1, AtNTT2 (*Arabidopsis thaliana*), CtNTT1, CtNTT2 (*Chlamydia trachomatis*), PamNTT1, PamNTT2 (*Protochlamydia amoebophila*), CcNTT (*Caedibacter caryophilus*), RpNTT1 (*Rickettsia prowazekii*).

In some embodiments, NTT is CNT1, CNT2, CNT3, ENT1, ENT2, OAT1, OAT3, or OCT1.

In some embodiments, NTT imports unnatural nucleic acids into an organism, e.g. a cell. In some embodiments, NTTs can be modified such that the nucleotide binding site of the NTT is modified to reduce steric entry inhibition of the unnatural nucleic acid into the nucleotide biding site. In some embodiments, NTTs can be modified to provide increased interaction with one or more unnatural features of the unnatural nucleic acids. Such NTTs can be expressed or engineered in cells for stably importing a UBP into the cells. Accordingly, the invention includes compositions that include a heterologous or recombinant NTT and methods of use thereof.

NTTs can be modified using methods pertaining to protein engineering. For example, molecular modeling can be carried out based on crystal structures to identify the locations of the NTTs where mutations can be made to modify a target activity or binding site. A residue identified as a target for replacement can be replaced with a residue selected using energy minimization modeling, homology modeling, and/or conservative amino acid substitutions, such as described in Bordo, et al. J Mol Biol 217: 721-729 (1991) and Hayes, et al. Proc Natl Acad Sci, USA 99: 15926-15931 (2002).

Any of a variety of NTTs can be used in a method or composition set forth herein including, for example, protein-based enzymes isolated from biological systems and functional variants thereof. Reference to a particular NTT, such as those exemplified below, will be understood to include functional variants thereof unless indicated otherwise. In some embodiments, a NTT is a wild type NTT. In some embodiments, a NTT is a modified, or mutant, NTT.

NTTs, with features for improving entry of unnatural nucleic acids into cells and for coordinating with unnatural nucleotides in the nucleotide biding region, can also be used. In some embodiments, a modified NTT has a modified nucleotide binding site. In some embodiments, a modified or wild type NTT has a relaxed specificity for an unnatural nucleic acid.

In some embodiments, a modified NTT has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the unnatural nucleic acid. In some embodiments, a modified or wild type NTT has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type NTT toward a natural nucleic acid and/or the unnatural nucleic acid without the modified sugar. In some embodiments, a modified or wild type NTT has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type NTT toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type NTT toward a nucleic acid comprising a triphosphate and/or the unnatural nucleic acid without the triphosphate. For example, a modified or wild type NTT can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type NTT toward the unnatural nucleic acid with a diphosphate or monophosphate, or no phosphate, or a combination thereof.

In some embodiments, a modified or wild type NTT has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid. In some embodiments, a modified or wild type NTT has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid. In some embodiments, a modified or wild type NTT has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid.

NTTs can be characterized according to their rate of dissociation from nucleic acids. In some embodiments a NTT has a relatively low dissociation rate for one or more natural and unnatural nucleic acids. In some embodiments a NTT has a relatively high dissociation rate for one or more natural and unnatural nucleic acids. The dissociation rate is an activity of a NTT that can be adjusted to tune reaction rates in methods set forth herein.

NTTs from native sources or variants thereof can be screened using an assay that detects importation of an unnatural nucleic acid having a particular structure. In one example, NTTs can be screened for the ability to import an unnatural nucleic acid or UBP; e.g., d5SICSTP, dNaMTP, or d5SICSTP-dNaMTP UBP. A NTT, e.g., a heterologous NTT, can be used that displays a modified property for the unnatural nucleic acid as compared to the wild-type NTT. For example, the modified property can be, e.g., $K_m$, $k_{cat}$, $V_{max}$, NTT importation in the presence of an unnatural nucleic acid (or of a naturally occurring nucleotide), average template read-length by a cell with the NTT in the presence of an unnatural nucleic acid, specificity of the NTT for an unnatural nucleic acid, rate of binding of an unnatural nucleic acid, or rate of product release, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the NTT optionally has an increased rate of binding of an unnatural nucleic acid, an increased rate of product release, and/or an increased cell importation rate, as compared to a wild-type NTT.

At the same time, a NTT can import natural nucleic acids, e.g., A, C, G, and T, into cell. For example, a NTT optionally displays a specific importation activity for a natural nucleic acid that is at least about 5% as high (e.g., 5%, 10%, 25%, 50%, 75%, 100% or higher), as a corresponding wild-type NTT. Optionally, the NTT displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type NTT.

NTTs used herein that can have the ability to import an unnatural nucleic acid of a particular structure can also be produced using a directed evolution approach. A nucleic acid synthesis assay can be used to screen for NTT variants having specificity for any of a variety of unnatural nucleic acids. For example, NTT variants can be screened for the ability to import an unnatural nucleic acid or UBP; e.g., d5SICSTP, dNaMTP, or d5SICSTP-dNaMTP UBP into nucleic acids. In some embodiments, such an assay is an in vitro assay, e.g., using a recombinant NTT variant. In some embodiments, such an assay is an in vivo assay, e.g., expressing a NTT variant in a cell. Such directed evolution techniques can be used to screen variants of any suitable NTT for activity toward any of the unnatural nucleic acids set forth herein.

Nucleic Acid Reagents & Tools

A nucleic acid reagent for use with a method, cell, or engineered microorganism described herein comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example. In some embodiments, a nucleic acid reagent or other reagent described herein is isolated or purified.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A nucleic acid or nucleic acid reagent can comprise certain elements, e.g., regulatory elements, often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

Nucleic acid reagents, e.g., expression cassettes and/or expression vectors, can include a variety of regulatory elements, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleotide triphosphate transporter nucleic acid segment. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3" to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

As noted above, nucleic acid reagents may also comprise one or more 5' UTR's, and one or more 3'UTR's. For example, expression vectors used in eukaryotic host cells (e.g., yeast, fungi, insect, plant, animal, human or nucleated cells) and prokaryotic host cells (e.g., virus, bacterium) can contain sequences that signal for the termination of transcription which can affect mRNA expression. These regions can be transcribed as polyadenylated segments in the untranslated portion of the mRNA encoding tissue factor protein. The 3" untranslated regions also include transcription termination sites. In some preferred embodiments, a transcription unit comprises a polyadenylation region. One benefit of this region is that it increases the likelihood that the transcribed unit will be processed and transported like mRNA. The identification and use of polyadenylation signals in expression constructs is well established. In some preferred embodiments, homologous polyadenylation signals can be used in the transgene constructs.

A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, -35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR is used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

Expression of a nucleotide triphosphate transporter from an expression cassette or expression vector can be controlled by any promoter capable of expression in prokaryotic cells or eukaryotic cells. A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments. In some embodiments, a promoter element can be isolated from a gene or organism and inserted in functional connection with a polynucleotide sequence to allow altered and/or regulated expression. A non-native promoter (e.g., promoter not normally associated with a given nucleic acid sequence) used for expression of a nucleic acid often is referred to as a heterologous promoter. In certain embodiments, a heterologous promoter and/or a 5'UTR can be inserted in functional connection with a polynucleotide that encodes a polypeptide having a desired activity as described herein. The terms "operably linked" and "in functional connection with" as used herein with respect to promoters, refer to a relationship between a coding sequence and a promoter element. The promoter is operably linked or in functional connection with the coding sequence when expression from the coding sequence via transcription is regulated, or controlled by, the promoter element. The terms "operably linked" and "in functional connection with" are utilized interchangeably herein with respect to promoter elements.

A promoter often interacts with a RNA polymerase. A polymerase is an enzyme that catalyzes synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., (3-lactamase), 0-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermenter, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

Nucleic acids encoding heterologous proteins, e.g., nucleotide triphosphate transporters, can be inserted into or employed with any suitable expression system. In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids).

Recombinant expression is usefully accomplished using an expression cassette that can be part of a vector, such as a plasmid. A vector can include a promoter operably linked to nucleic acid encoding a nucleotide triphosphate transporter. A vector can also include other elements required for transcription and translation as described herein. An expression cassette, expression vector, and sequences in a cassette or vector can be heterologous to the cell to which the unnatural nucleotides are contacted. For example, a nucleotide triphosphate transporter sequence can be heterologous to the cell.

A variety of prokaryotic and eukaryotic expression vectors suitable for carrying, encoding and/or expressing nucleotide triphosphate transporters can be produced. Such expression vectors include, for example, pET, pET3d, pCR2.1, pBAD, pUC, and yeast vectors. The vectors can be used, for example, in a variety of in vivo and in vitro situations. Non-limiting examples of prokaryotic promoters that can be used include SP6, T7, T5, tac, bla, trp, gal, lac, or maltose promoters. Non-limiting examples of eukaryotic promoters that can be used include constitutive promoters, e.g., viral promoters such as CMV, SV40 and RSV promoters, as well as regulatable promoters, e.g., an inducible or repressible promoter such as a tet promoter, a hsp70 promoter, and a synthetic promoter regulated by CRE. Vectors for bacterial expression include pGEX-5X-3, and for eukaryotic expression include pClneo-CMV. Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in Verma, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

Cloning

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described herein. In some embodiments, a cloning strategy can be combined with genetic manipulation such as recombination (e.g., recombination of a nucleic acid reagent with a nucleic acid sequence of interest into the genome of the organism to be modified, as described further herein). In some embodiments, the cloned ORF(s) can produce (directly or indirectly) modified or wild type nucleotide triphosphate transporters and/or polymerases), by engineering a microorganism with one or more ORFs of interest, which microorganism comprises altered activities of nucleotide triphosphate transporter activity or polymerase activity.

A nucleic acid may be specifically cleaved by contacting the nucleic acid with one or more specific cleavage agents. Specific cleavage agents often will cleave specifically according to a particular nucleotide sequence at a particular site. Examples of enzyme specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, BsaI, Bsm I, BsmBI, BssH II, BstE II, Cfo I, Cla I, Dde I, Dpn I, Dra I, EcIX I, EcoR I, EcoR I, EcoR II, EcoR V, Hae II, Hae II, Hind II, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfate, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., Sauer, Curr. Opin. Biotech. 5:521-527 (1994)). Other examples of recombination sites include attB, attP, attL, and attR sequences, and mutants, fragments, variants and derivatives thereof, which are recognized by the recombination protein a, Int and by the auxiliary proteins integration host factor (IHF), FIS and excisionase (Xis) (e.g., U.S. Pat. Nos. 5,888,732; 6,143,557; 6,171,861; 6,270, 969; 6,277,608; and 6,720,140; U.S. patent application Ser. Nos. 09/517,466, and 09/732,914; U.S. Patent Publication No. US2002/0007051; and Landy, Curr. Opin. Biotech. 3:699-707 (1993)).

Examples of recombinase cloning nucleic acids are in Gateway® systems (Invitrogen, California), which include at least one recombination site for cloning desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A nucleic acid reagent sometimes contains one or more origin of replication (ORI) elements. In some embodiments, a template comprises two or more ORIs, where one functions efficiently in one organism (e.g., a bacterium) and another function efficiently in another organism (e.g., a eukaryote, like yeast for example). In some embodiments, an ORI may function efficiently in one species (e.g., S. cerevisiae, for example) and another ORI may function efficiently in a different species (e.g., S. pombe, for example). A nucleic acid reagent also sometimes includes one or more transcription regulation sites.

A nucleic acid reagent, e.g., an expression cassette or vector, can include nucleic acid sequence encoding a marker product. A marker product is used to determine if a gene has been delivered to the cell and once delivered is being expressed. Example marker genes include the E. coli lacZ gene which encodes β-galactosidase and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern et al., J. Molec. Appl. Genet. 1: 327 (1982)), mycophenolic acid, (Mulligan et al., Science 209: 1422 (1980)) or hygromycin, (Sugden, et al., Mol. Cell. Biol. 5: 410-413 (1985)).

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism, and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent can be of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (e.g., Biochemistry 1996 Jun. 25; 35(25):8429-38). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

In some embodiments, a kit includes a suitable packaging material to house the contents of the kit. In some cases, the packaging material is constructed by well-known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit. For example, a label can indicate that the kit is useful for a method of synthesizing a polynucleotide or for a method of determining the sequence of a nucleic acid.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and where they can be obtained.

In some embodiments, a kit is provided that is useful for stably incorporating an unnatural nucleic acid into a cellular nucleic acid, e.g., using the methods provided by the present invention for preparing genetically engineered cells. In one embodiment, a kit described herein includes a genetically engineered cell and one or more unnatural nucleic acids. In another embodiment, a kit described herein includes an isolated and purified plasmid comprising a sequence selected from SEQ ID NOs: 1-4. In a further embodiment, a kit described herein includes an isolated and purified plasmid comprises a sequence of SEQ ID NO: 4, in which the W motif of SEQ ID NO:4 comprises a sequence selected from SEQ ID NOs: 5, 7, 9, 11, 13, 15, 17, 19, 21, 23, 25, or 27; and/or the Y motif of SEQ ID NO:4 comprises a sequence selected from SEQ ID NOs: 6, 8, 10, 12, 14, 16, 18, 20, 22, 24, or 26.

In additional embodiments, the kit described herein provides a cell and a nucleic acid molecule containing a heterologous gene for introduction into the cell to thereby provide a genetically engineered cell, such as expression vectors comprising the nucleic acid of any of the embodiments hereinabove described in this paragraph.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 4." Generally, the term "about" includes an amount that would be expected to be within experimental error.

The section headings used herein are for organizational purposes only and are not to be construed as limiting the subject matter described.

EXAMPLES

These examples are provided for illustrative purposes only and not to limit the scope of the claims provided herein.

Example 1: Control of UBP Mutations in *E. coli*

Figure 1B:
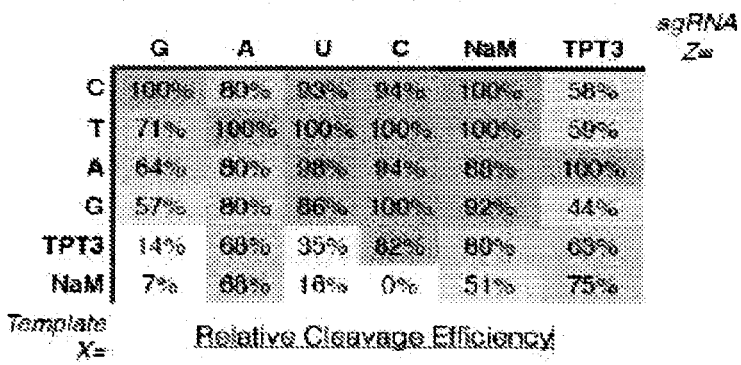
Figure 1C:
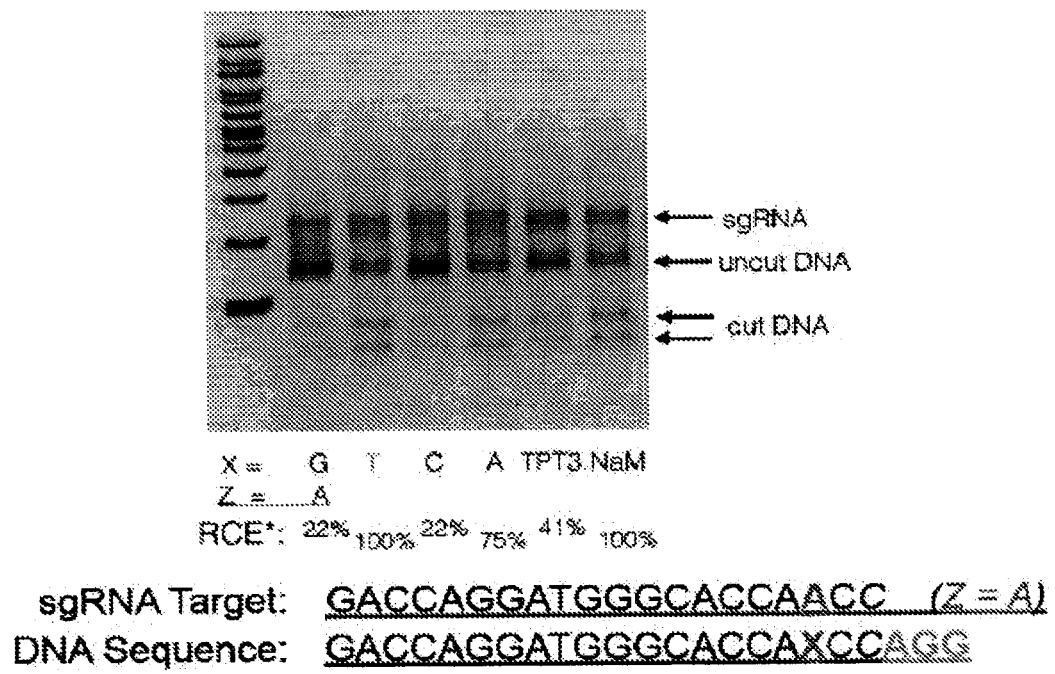
FIG. 1C exemplifies a PAGE analysis to determine RCE of one of these variations.

In some instances, Cas9 endonucleases are programmed by one or more single guide RNAs (sgRNAs) to create double strand breaks upstream of a protospacer adjacent motif (PAM) recognition element, which in *E. coli* results in rapid plasmid degradation by RecBCD and associated nucleases. Cas9/natural sgRNA complexes are less efficient at cleaving DNA sequences containing a dNaM-dTPT3 than a fully natural sequence or even a sequence containing a natural mispair, in some instances, due to the unique structure and/or lack of H-bonding potential of the unnatural nucleobases (FIGS. 1A, 1B, and 1C).

Figure 2:
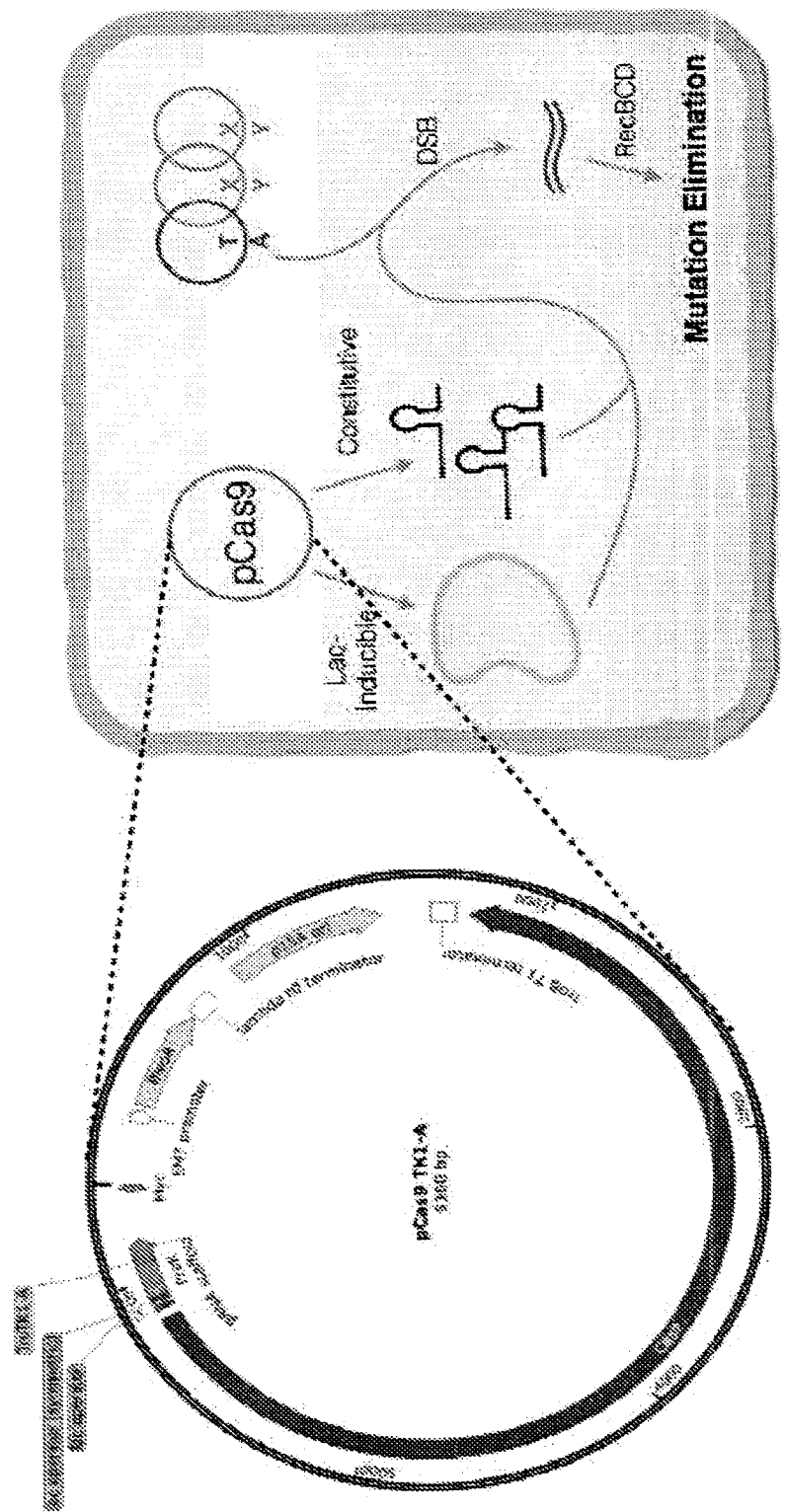
FIG. 2 exemplifies the pCas9/TK1-A plasmid.

To understand whether an appropriate sgRNA used in conjunction with Cas9 degrades DNA that has lost a UBP within a cell, a plasmid containing the dNaM-dTPT3 UBP in a sequence referred to as TK-1 was constructed, as well as a plasmid pCas9/TK1-A (FIG. 2), which expresses Cas9 under an IPTG-inducible LacO promoter and an sgRNA that is fully complementary to the TK-1 sequence but contains the most common mutation, dNaM to dT, under the control of a constitutive ProK promoter. In addition, an analogous plasmid, pCas9/TruTK1-A, was constructed with a more stringent truncated TruTK1-A sgRNA which targeted the same mutation.

Figure 3:
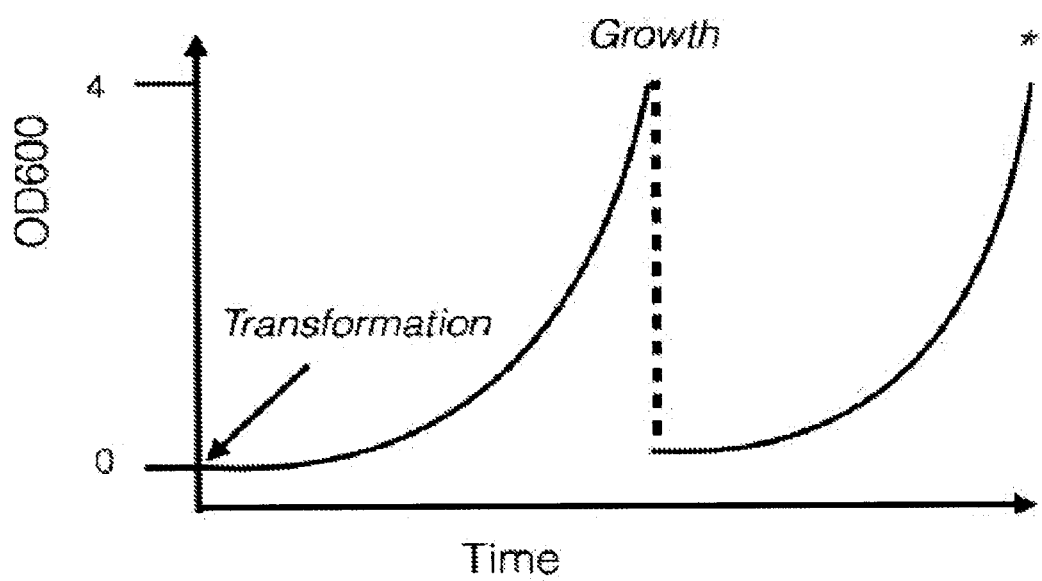
FIG. 3 exemplifies the growth-regrowth cycle of the transformed E. coli first grown in the presence of the unnatural triphosphates to saturation, diluted 250-fold, and then grown to saturation again.
Figures 4A, 4B:
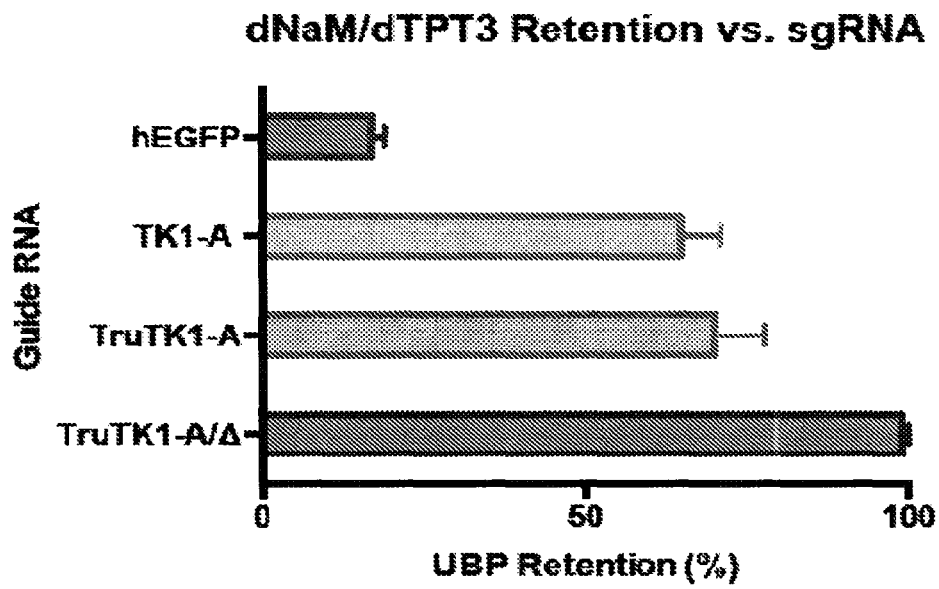
FIG. 4A illustrates the percent of UBP retention when various types of guide RNA are used.
FIG. 4B illustrates the sequences of both the target strand and the various sgRNA used. Target sequence and guide RNA sequences also included.
Figure 4C:
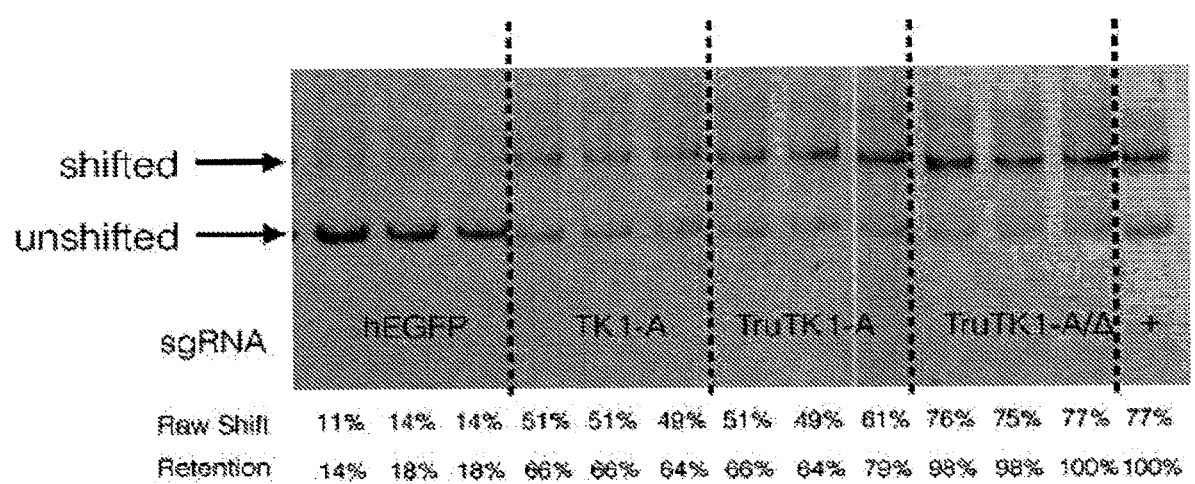
FIG. 4C exemplifies an analysis of UBP retention using the aforementioned sgRNAs.
Figure 5A:
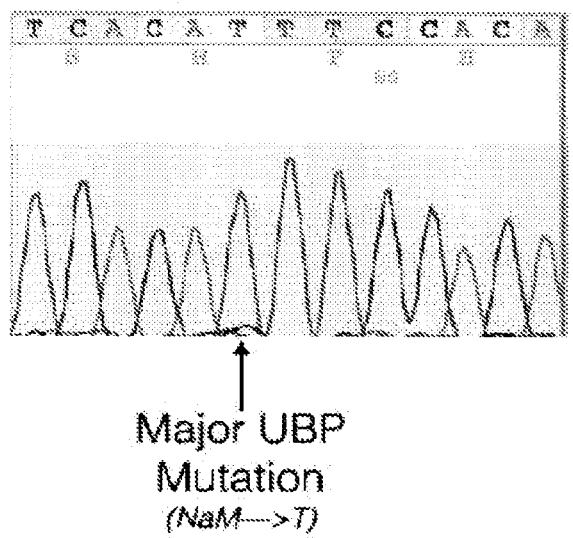
FIG. 5A illustrates the major mutation (dNaM→dT)
Figure 5B:
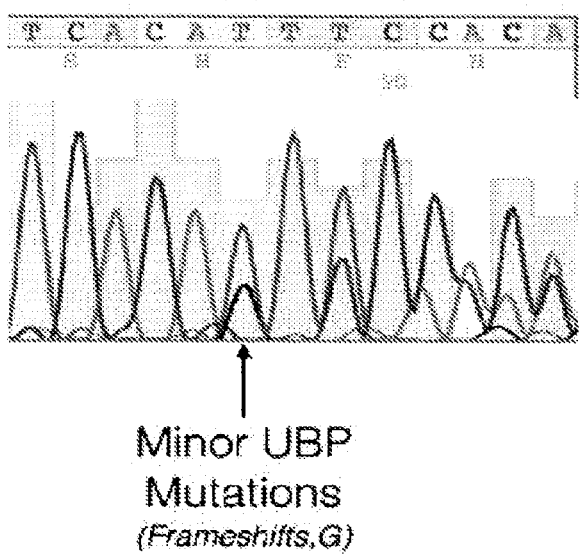
FIG. 5B illustrates the minor mutations (G, frameshift).

A strain of BL21(DE3) *E. coli* engineered to import dNaMTP and dTPT3TP via PtNTT2 was transformed with the UBP-containing plasmid and one of the pCas9 plasmids, and then grown in the presence of the unnatural triphosphates to saturation, diluted 250-fold, and grown again to saturation, all in the presence of dNaMTP and dTPT3TP supplied to the media (FIG. 3); this growth-regrowth paradigm is in some cases used for the induction of recombinant proteins. Under these conditions, dNaM-dTPT3 retention in control experiments with a scrambled sgRNA dropped to 14% after the second outgrowth (FIGS. 4A, 4B, and 4C). In contrast, in the presence of correct guide RNAs, retention was increased to 70% (TK1-A) or 77% (TruTK1-A) (FIGS. 4A, 4B, and 4C), with the remaining 30% or 23% of natural plasmids composed mainly of mutants that had lost the UBP by a single nucleotide deletion, which results in a sequence that cannot be targeted by either sgRNA. Thus, a plasmid, pCas9/TruTK1-A/A, was constructed which expresses two sgRNAs and thus targets both the major substitution (FIG. 5A) and the deletion mutation (FIG. 5B). In this case, with the same growth and regrowth assay, loss of the UBP was undetectable (FIGS. 4A, 4B, and 4C).

Example 2: UBP Retention Enhancement is Most Effective within the Seed Region of the sgRNA With natural DNA, Cas9/sgRNA cleavage stringency depends on the identity and distance of mismatches from the PAM recognition element. Thus, the ability of Cas9 to enforce dNaM-dTPT3 retention was assessed in either the coding or noncoding strand, at three different positions relative to the same PAM within the hGFP gene (six sequences in total; FIG. 5). In each case, analogous dual sgRNA cassettes were used in which the sgRNA that targets the substitution mutant varies across all four possible natural nucleotides (pCas9/hGFP-N/A (N=G, C, A, or U).

The same *E. coli* strain as in Example 1 was transformed with a UBP-containing hGFP plasmid and a pCas9/hGFP-N/A plasmid. UBP retention was assessed after cells reached an $OD_{600}$~1.0. For the four cases in which the UBP was within the seed region (the region of duplex formation between the target and sgRNA, and which is the sequence most sensitive to Cas9 editing), retention was good to moderate in the absence of Cas9 induction, but increased with low levels of Cas9 expression (zero to 10 uM IPTG), regardless of the specific mutations targeted by the sgRNA. Moreover, traditional cloning via plating and inoculation obtained microgram quantities of purified plasmid with undetectable loss of the UBP. For the two cases in which the UBP was outside of the seed region, retention was poor in the absence of Cas9 induction, but increased with Cas9 expression, although this required sgRNAs targeting the major mutation and was optimal with higher levels of induction (100 uM IPTG).

Example 3: Error-Elimination with CRISPR for Maintenance of UBPs

To explore the CRISPR/Cas9 editing system, in the context of its ability to enforce retention of the UBP in different sequences, a total of 16 different sequences were examined in which the dNaM of a dNaM-dTPT3 UBP was flanked by all possible nucleotides (Tables 1-3; FIG. 6). *E. coli* cells were transformed with a plasmid containing the UBP and a plasmid containing sgRNAs that target the major substitution mutation and the deletion mutation. A scrambled sgRNA control and low levels of Cas9 induction (10 uM IPTG) resulted in low UBP retention.

TABLE 1

| | No Cas9 | | | Cas9 (+10 μM ITPG) | |
|---|---|---|---|---|---|
| 3' Nuc | % UBP Retention | 5' Nuc | 3' Nuc | % UBP Retention | 5' Nuc |
| G | 36 ± 28 | G | G | 98 ± 3 | G |
| | 35 ± 5 | A | | 98 ± 1 | A |
| | 85 ± 2 | C | | 98 ± 1 | C |
| | 89 ± 3 | T | | 95 ± 12 | T |
| A | 17 ± 2 | G | A | 75 ± 3 * | G |
| | 80 | A | | 95 | A |
| | 84 ± 8 | C | | 92 ± 3 | C |
| | 90 | T | | 99 ± 5 | T |
| C | 0 | G | C | 78 ± 34 * | G |
| | 0 | A | | 78 ± 12 | A |
| | 29 ± 2 | C | | 98 ± 1 | C |
| | 27 ± 2 | T | | 60 ± 6 * | T |
| T | 0 | G | T | 47 ± 4 | G |
| | 35 ± 4 | A | | 93 ± 8 | A |
| | 72 ± 2 | C | | 101 ± 4 | C |
| | 75 | T | | 87 ± 18 | T |

* Retention with 100 μM IPTG induction of Cas9

The results demonstrated UBP was retained in the sequences tested with Cas9 and two sgRNAs. In some instances, three sequence contexts that exhibited relatively poor retention with low (10 uM IPTG) Cas9 induction (CNaMG, CNaMT, and ANaMG), were examined at higher Cas9 induction (100 uM IPTG), in which a higher UBP retention rate was observed compared to the low Cas9 induction tested above. In addition, replication (and targeting, by Cas9) of the 16 UBP-containing DNA sequences (targeting motif illustrated in Table 2) was assessed by plating onto solid media containing dNaMTP and dTPT3TP to select for single colonies, analogous to standard molecular biology practices. In some instances, selection of clonal populations purifies the UBP-containing plasmids away from those that contain errors introduced during their construction.

Example 4: Sequences Utilized in a Method Described Herein

A plasmid described herein is illustrated by SEQ ID NO: 1. In some instances, it is referred to as pCas9-TK1-A.

SEQ ID NO: 1

```
ctctgcttggacggacaggatgtatgctgtggctatttaaggataactaccttgggggccattcattgattccaactccgggatctggt cacgcagggcaaaaaagctccgttttagctcgttcctcctctggcgctccaagacgttgtgtgttcgcctcttgacattctcctcggtg tccgagggcctgtgtgaaattgttatccgctcacaattccacacagacgtcgttgacaattaatcatcggcatagtatatcggcatag tataatacgacaaggtgaggaactaaaccatggccaagttgaccagtgccgttccggtgctcaccgcgcgcgacgtcgccggagcggtc gagttctggaccgaccggctcgggttctcccgggacttcgtggaggacgacttcgccggtgtggtccgggacgacgtgaccctgttcat cagcgcggtccaggaccaggtggtgccggacaacaccctggcctgggtgtgggtgcgcggcctggacgagctgtacgccgagtggtcgg
```

-continued

```
aggtcgtgtccacgaacttccgggacgcctccgggccggccatgaccgagatcggcgagcagccgtgggggcgggagttcgccctgcgc
gacccggccggcaactgcgtgcacttcgtggccgaggagcaggactgagagctcgcttggactcctgttgatagatccagtaatgacct
cagaactccatctggatttgttcagaacgctcggttgccgccgggcgatatattggtgagaatccaagcactagtaacaacttatatcg
tatggggctgacttcaggtgctacatttgaagagataaattgcactgaaatctagtaatattttatctgattaataagatgatcttctt
gagatcgttttggtctgcgcgtaatctcttgctctgaaaacgaaaaaaccgccttgcagggcggttttcgaaggttctctgagctacc
aactctttgaaccgaggtaactggcttggaggagcgcagtcaccaaaacttgtcctttcagtttagccttaaccggcgcatgacttcaa
gactaactcctctaaatcaattaccagtggctgctgccagtggtgcttttgcatgtctttccgggttggactcaagacgatagttaccg
gataaggcgcagcggtcggactgaacgggggttcgtgcatacagtccagcttggagcgaactgcctacccggaactgagtgtcaggcg
tggaatgagacaaacgcggccataacagcggaatgacaccggtaaaccgaaaggcaggaacaggagagcgcacgagggagccgccaggg
ggaaacgcctggtatctttatagtcctgtcgggtacgccaccactgatttgagcgtcagattcgtgatgcttgtcaggggggcggagc
ctatggaaaaacggctttgccgcggccctctcacttccctgttaagtatcttcctggcatcttccaggaaatctccgccccgttcgtaa
gccatttccgctcgccgcagtcgaacgaccgagcgtagcgagtcagtgagcgaggaagcggaatatatcccctaggtctagggcggcgg
atttgtcctactcaggagagcgttcaccgacaaacaacagatataaacgaaaggcccagtcttcgactgagcctttcgttttatttgat
gcctctagattacaccttcctcttcttcttggggtcagccctgctgtctccaccgagctgagagaggtcgattcttgtttcatagagcc
ccgtaattgactgatgaatcagtgtggcgtccaggacctcctttgtagaggtgtaccgctttctgtctatggtggtgtcgaagtacttg
aaggctgcaggcgcgcccaagttggtcagagtaaacaagtggataatgttttctgcctgctccctgatgggcttatccctgtgcttatt
gtaagcagaaagcaccttatcgaggttagcgtcggcgaggatcactcttttggagaattcgcttatttgctcgatgatctcatcaaggt
agtgtttgtgttgttccacgaacagctgcttctgctcattatcttcgggagaccctttgagcttttcatagtggctggccagatacaag
aaattaacgtatttagagggcagtgccagctcgttacctttctgcagctcgcccgcactagcgagcattcgtaccggccgattcaagct
caaagagagagtacttgggaagcttaatgatgaggtcattagacctctttatatcctttcgcctcgagaaagtcgatgggtttttttc
gaagcttgatcgctccatgattgtgatgcccagcagttccttgacgcttagagttttttagacttccctttctccacttttggccacaac
cagtacactgtaagcgactgtaggagaatcgaatccgccgtatttcttggggtcccaatctttttgcgtgcgatcagcttgtcgctgt
tcctttcgggaggatactttccttggagaagcctccggtctgtacttcggtctattaacgatgttcacctgcggcatggacaggacct
tccggactgtcgcgaaatccctacccttgtcccacacgatttctcctgtttctccgtttgtttcgataagtggtcgcttccgaatctct
ccattggccagtgtaatctcggtcttgaaaaaattcataatattgctgtaaaagaagtacttagcggtggccttgcctatttcctgctc
agactttgcgatcattttcctaacatcgtacactttatagtctccgtaaacaaattcagattcaagcttgggatattttttgataagtg
cagtgcctaccactgcattcaggtaggcatcatgcgcatggtggtaattgttgatctctctcaccttataaaactgaaagtcctttctg
aaatctgagaccagcttagacttcagagtaataactttcacctctcgaatcagtttgtcattttcatcgtacttggtgttcatgcgtga
atcgagaatttgggccacgtgcttggtgatctggcgtgtctcaacaagctgcctttgatgaagccggctttatccaactcagacaggc
cacctcgttcagccttagtcagattatcgaacttccgttgtgtgatcagtttggcgttcagcagctgccgccaataatttttcattact
tgacaacttcttctgagggggacgttatcactcttccctctattttatcggatcttgtcaacactttattatcaatagaatcatctttg
agaaaagactggggcacgatatgatccacgtcgtagtcggagagccgattgatgtccagtcctgatccacgtacatgtccctgccgtt
ctgcaggtagtacaggtagagcttctcattctgaagctgggtgttttcaactgggtgttccttaaggatttgggaccccagttctttta
taccctcttcaatcctcttcatcctttccctactgttcttctgtcccttctgggtagtttggttctctcgggccatctcgataacgata
ttctcgggcttatgccttcccattactttgacgagttcatccacgacccttaacggtctgcagtattccctattgatagctgggctacct
gcaagattagcgatgtgctcgtgaagactgtcccctggccagaaacttgtgctttctggatgtcctccttaaaggtgagagagtcatc
atggatcaactgcatgaagttccggttggcaaatccatcggacttaagaaaatccaggattgtctttccactctgcttgtctcggatcc
cattgatcagttttcttgacagccgcccccatcctgtatatcggcgcctcttgagctgtttcatgactttgtcgtcgaagagatgagcg
taagttttcaagcgttcttcaatcatctccctatcttcaaacaacgtaagggtgaggacaatgtcctcaagaatgtcctcgttctcctc
attgtccaggaagtcctgtctttaatgattttcaggagatcgtgatacgttcccagggatgcgttgaagcgatcctccactccgctga
tttcaacagagtcgaaacattcaatctttttgaaatagtcttctttgagctgtttcacggtaactttccggttcgtcttgaagaggagg
```

-continued tccacgatagattcttctgctctccagacaggaatgctggctttctcatcccttctgtgacgtatttgaccttggtgagctcgttataa actgtgaagtactcgtacagcagagagtgtttaggaagcaccttttcgttaggcagattttttatcaaagttagtcatcctttcgatgaa ggactgggcagaggccccttatccacgacttcctcgaagttccagggagtgatggtctcttctgatttgcgagtcatccacgcgaatc tggaatttccccgggcgaggggcctacatagtagggtatccgaaatgtgaggattttctcaatcttttcctgttatctacaaaaagg ggtagaaatcctcttgccgcctgaggatagcgtgcagttcgcccaggtgaatctggtggggatgcttccattgtcgaaagtgcgctgt ttgcgcaacagatcttctctgttaagctttaccagcagctcctcggtgccgtccattattccaagatgggcttaataaatttgtaaaat tcctcctggcttgctccgccgtcaatgtatccggcgtagccattttagactgatcgaagaaaatttccttgtacttctcaggcagttg ctgtctgacaagggcttcagcaaagtcaagtcttggtggtgctcatcatagcgcttgatcatactagcgctcagcggagctttggtga tctccgtgttcactcgcagaatatcactcagcagaatggcgtctgacaggttctttgccgccaaaaaaggtctgcgtactggtcgccg atctgggccagcagattgtcgagatcatcatcgtaggtgtctttgctcagttgaagcttggcatcttcggccaggtcgaagttagttt aaagttggggtcagcccgagtgacagggcgataagattaccaaacaggccgttcttcttctccccagggagctgtgcgatgaggtttt cgagccgccgggatttggacagcctagcgctcaggattgctttggcgtcaactccggatgcgttgatcgggttctcttcgaaaagctga ttgtaagtctgaaccagttggataaagagtttgtcgacatcgctgttgtctgggttcaggtcccctcgatgaggaagtgtccccgaaa tttgatcatatgcgccagcgcgagatagatcaaccgcaagtcagcccttatcagtactgtctacaagcttcttcctcagatgatatgg ttgggtacttttcatggtacgccacctcgtccacgatattgccaaagattgggtggcgctcgtgctattatcctcctccaccaaaaagg actcctccagcctatggaagaaagagtcatccaccttagccatctcattactaaagatctcctgcaggtagcagatccgattctttctg cgggtatatctgcgccgtgctgttcttttgagccgcgtggcttcggccgtctcccggagtcgaacaggagggcgccaatgaggttctt ctttatgctgtggcgatcggtattgcccagaactttgaattttttgctcggccaccttgtactcgtccgtaatgacggcccagccgacgc tgtagtgccgatatcgagcccaatggagtacttcttgtccatggtacctttctcctctttaatgaattctgtgtgaaattgttatccgc tcacaattgaatctatcataattgtgagcgctcacaattgtaaaggttagatctaaaactagtggcagcggctaactaagcggcctgct gactttctcgccgatcaaaaggcattttgctattaagggattgacgagggcgtatctgcgcagtaagatgcgccccgcattGTATGTTG

TGTGGAAATGTGAGgttttagagctagaaatagcaagttaaaataaggctagtccgttatcaacttgaaaaagtggcaccgagtcggtg ctttttttaattcgaaaagcctgctcaacgagcaggcattaggtcgacagttcataggtgattgctcaggacatttctgttagaaggaa tcgttaccttacttaccttacgcacaagagttccgtagctgttcaagtttgtgtttcaactgttctcgtcgtttccgcaacaagtcctc ttcagaaatgagctttgctc A plasmid described herein is illustrated by SEQ ID NO: 2. In some instances, it is referred to as pCas9-TruTK1-A.

SEQ ID NO: 2 ctctgcttggacggacaggatgtatgctgtggctatttaaggataactaccttgggggccattcattgattccaactccgggatctggt cacgcagggcaaaaaagctccgttttagctcgttcctcctctggcgctccaagacgttgtgtgttcgcctcttgacattctcctcggtg tccgagggccctgtgtgaaattgttatccgctcacaattccacacagacgtcgttgacaattaatcatcggcatagtatatcggcatag tataatacgacaaggtgaggaactaaaccatggccaagttgaccagtgccgttccggtgctcaccgcgcgcgacgtcgccggagcggtc gagttctggaccgaccggctcgggttctcccgggacttcgtggaggacgacttcgccggtgtggtccgggacgacgtgaccctgttcat cagcgcggtccaggaccaggtggtgccggacaacaccctggcctgggtgtgggtgcgcggcctggacgagctgtacgccgagtggtcgg aggtcgtgtccacgaacttccgggacgcctccgggccggccatgaccgagatcggcgagcagccgtgggggcgggagttcgccctgcgc gacccggccggcaactgcgtgcacttcgtggccgaggagcaggactgagagctcgcttggactcctgttgatagatccagtaatgacct cagaactccatctggatttgttcagaacgctcggttgccgccgggcgatatattggtgagaatccaagcactagtaacaacttatatcg tatgggctgacttcaggtgctacatttgaagagataaattgcactgaaatctagtaatattttatctgattaataagatgatcttctt gagatcgttttggtctgcgcgtaatctcttgctctgaaaacgaaaaaaccgccttgcagggcggttttttcgaaggttctctgagctacc aactctttgaaccgaggtaactggcttggaggagcgcagtcaccaaaacttgtcctttcagtttagccttaaccggcgcatgacttcaa -continued gactaactcctctaaatcaattaccagtggctgctgccagtggtgcttttgcatgtctttccggggttggactcaagacgatagttaccg gataaggcgcagcggtcggactgaacgggggggttcgtgcatacagtccagcttggagcgaactgcctacccggaactgagtgtcaggcg tggaatgagacaaacgcggccataacagcggaatgacaccggtaaaccgaaaggcaggaacaggagagcgcacgagggagccgccaggg ggaaacgcctggtatctttatagtcctgtcgggtacgccaccactgatttgagcgtcagatttcgtgatgcttgtcaggggggcggagc ctatggaaaaacggctttgccgcggccctctcacttccctgttaagtatcttcctggcatcttccaggaaatctccgcccgttcgtaa gccatttccgctcgccgcagtcgaacgaccgagcgtagcgagtcagtgagcgaggaagcggaatatatcccctaggtctagggcggcgg atttgtcctactcaggagagcgttcaccgacaaacaacagataaaacgaaaggcccagtctttcgactgagcctttcgttttatttgat gcctctaga<ins>ttacaccttcctcttcttcttggggtcagccctgctgtctccaccgagctgagagaggtcgattcttgtttcatagagcc</ins>

<ins>ccgtaattgactgatgaatcagtgtggcgtccaggacctcctttgtagaggtgtaccgctttctgtctatggtggtgtcgaagtacttg</ins>

<ins>aaggctgcaggcgcgcccaagttggtcagagtaaacaagtggataatgttttctgcctgctccctgatgggcttatccctgtgcttatt</ins>

<ins>gtaagcagaaagcaccttatcgaggttagcgtcggcgaggatcactcttttggagaattcgcttatttgctcgatgatctcatcaaggt</ins>

<ins>agtgtttgtgttgttccacgaacagctgcttctgctcattatcttcgggagacccttttgagcttttcatagtggctggccagatacaag</ins>

<ins>aaattaacgtatttagagggcagtgccagctcgttacctttctgcagctcgcccgcactagcgagcattcgtttccggccgattcaagc</ins>

<ins>tcaaagagagagtacttgggaagcttaatgatgaggtcattagacctctttatatcctttcgcctcgagaaagtcgatgggttttttt</ins>

<ins>cgaagcttgatcgctccatgattgtgatgcccagcagttccttgacgcttagagtttttttagacttcccttctccactttggccacaa</ins>

<ins>ccagtacactgtaagcgactgtaggagaatcgaatccgccgtatttcttggggtcccaatcttttttgcgtgcgatcagcttgtcgctg</ins>

<ins>ttccttttcgggaggatactttccttggagaagcctccggtctgtacttcggtctattaacgatgttcacctgcggcatggacaggacc</ins>

<ins>ttccggactgtcgcgaaatccctaccttgtcccacacgattttctcctgtttctccgtttgtttcgataagtggtcgcttccgaatctc</ins>

<ins>tccattggccagtgtaatctcggtcttgaaaaaattcataatattgctgtaaaagaagtacttagcggtggccttgcctatttcctgct</ins>

<ins>cagactttgcgatcattttcctaacatcgtacactttatagtctccgtaaacaaattcagattcaagcttgggatatttttttgataagt</ins>

<ins>gcagtgcctaccactgcattcaggtaggcatcatgcgcatggtggtaattgttgatctctcacccttataaaactgaaagtcctttct</ins>

<ins>gaaatctgagaccagcttagacttcagagtaataactttcacctctcgaatcagtttgtcattttcatcgtacttggtgttcatgcgtg</ins>

<ins>aatcgagaatttgggccacgtgcttggtgatctggcgtgtctcaacaagctgccttttgatgaagccggctttatccaactcagacagg</ins>

<ins>ccacctcgttcagccttagtcagattatcgaacttccgttgtgtgatcagtttggcgttcagcagctgccgccaataattttttcattac</ins>

<ins>ttgacaacttcttctgaggggacgttatcactcttccctctattttttatcggatcttgtcaacactttattatcaatagaatcatcttt</ins>

<ins>gagaaaagactggggcacgatatgatccacgtcgtagtcggagagccgattgatgtccagttcctgatccacgtacatgtccctgccgt</ins>

<ins>tctgcaggtagtacaggtagagcttctcattctgaagctgggtgttttcaactgggtgttccttaaggatttgggacccagttcttttt</ins>

<ins>atacccctcttcaatcctcttcatcctttccctactgttcttctgtcccttctgggtagtttggttctctcgggccatctcgataacgat</ins>

<ins>attctcgggcttatgccttcccattactttgacgagttcatccacgaccttaacggtctgcagtattccctattgatagctgggctacc</ins>

<ins>tgcaagattagcgatgtgctcgtgaagactgtcccctggccagaaacttgtgctttctggatgtcctccttaaaggtgagagagtcat</ins>

<ins>catggatcaactgcatgaagttccggttggcaaatccatcggacttaagaaaatccaggattgtctttccactctgcttgtctcggatc</ins>

<ins>ccattgatcagttttcttgacagccgcccccatcctgtatatcggcgcctcttgagctgtttcatgactttgtcgtcgaagagatgagc</ins>

<ins>gtaagttttcaagcgttcttcaatcatctccctatcttcaaacaacgtaaggggtgaggacaatgtcctcaagaatgtcctcgttctcct</ins>

<ins>cattgtccaggaagtccttgtctttaatgattttcaggagatcgtgatacgttcccagggatgcgttgaagcgatcctccactccgctg</ins>

<ins>atttcaacagagtcgaaacattcaatcttttttgaaatagtctcttttgagctgtttcacggtaacttccggttcgtcttgaagaggag</ins>

<ins>gtccacgatagattcttctgctctccagacaggaatgctggctttctcatcccttctgtgacgtatttgaccttggtgagctcgttata</ins>

<ins>aactgtgaagtactcgtacagcagagagtgtttaggaagcaccttttcgttaggcagattttttatcaaagttagtcatcctttcgatga</ins>

<ins>aggactgggcagaggcccccttatccacgacttcctcgaagttccagggagtgatggtctcttctgatttgcgagtcatccacgcgaat</ins>

<ins>ctggaatttccccgggcgagggggcctacatagtagggtatccgaaatgtgaggattttctcaatcttttccctgttatctacaaaaag</ins>

<ins>gggtagaaatcctcttgccgcctgaggatagcgtgcagttcgcccaggtgaatctggtgggggatgcttccattgtcgaaagtgcgctg</ins>

-continued

```
tttgcgcaacagatcttctctgttaagctttaccagcagctcctcggtgccgtccattattccaagatgggcttaataaatttgtaaaa
ttcctcctggcttgctccgccgtcaatgtatccggcgtagccattttagactgatcgaagaaaattcttgtacttctcaggcagtt
gctgtctgacaagggccttcagcaaagtcaagtcttggtggtgctcatcatagcgcttgatcatactagcgctcagcggagctttggtg
atctccgtgttcactcgcagaatatcactcagcagaatggcgtctgacaggttcttgccgccaaaaaaggtctgcgtactggtcgcc
gatctgggccagcagattgtcgagatcatcatcgtaggtgtctttgctcagttgaagcttggcatcttcggccaggtcgaagttagatt
taaagttggggtcagcccgagtgacagggcgataagattaccaaacaggccgttcttcttctcccagggagctgtgcgatgaggttt
tcgagccgcgggatttggacagcctagcgctcaggattgctttggcgtcaactccggatgcgttgatcgggttctcttcgaaaagctg
attgtaagtctgaaccagttggataaagagtttgtcgacatcgctgttgtctgggttcaggtcccctcgatgaggaagtgtccccgaa
atttgatcatatgcgccagcgcgagatagatcaaccgcaagtcagccttatcagtactgtctacaagcttcttcctcagatgatatg
gttgggtacttttcatggtacgccacctcgtccacgatattgccaaagattgggtggcgctcgtgctattatcctcctccaccaaaaag
gactcctccagcctatggaagaaagagtcatccaccttagccatctcattactaaagatctcctgcaggtagcagatccgattctttct
gcgggtatatctgcgccgtgctgttcttttgagccgcgtggcttcggccgtctccccggagtcgaacaggagggcgccaatgaggttct
tctttatgctgtggcgatcggtattgcccagaactttgaattttttgctcggcaccttgtactcgtccgtaatgacggcccagccgacg
ctgtagtgccgatatcgagcccaatggagtacttcttgtccatggtacctttctcctctttaatgaattctgtgtgaaattgttatccg
ctcacaattgaatctatcataattgtgagcgctcacaattgtaaaggttagatctaaaactagtggcagcggctaactaagcggcctgc
tgactttctcgccgatcaaaaggcatttttgctattaagggattgacgagggcgtatctgcgcagtaagatgcgccccgcatt𝐆𝐓𝐓𝐆𝐓𝐆𝐓
𝐆𝐆𝐀𝐀𝐀𝐓𝐆𝐓𝐆𝐀𝐆gttttagagctagaaatagcaagttaaaataaggctagtccgttatcaacttgaaaaagtggcaccgagtcggtgctt
𝐭𝐭𝐭𝐭aattcgaaaagcctgctcaacgagcaggcttttttggtcgacagttcataggtgattgctcaggacatttctgttagaaggaat
cgttttccttacttttccttacgcacaagagttccgtagctgttcaagtttgtgtttcaactgttctcgtcgtttccgcaacaagtcct
cttcagaaatgagcttttgctc
```

A plasmid described herein is illustrated by SEQ ID NO: 3. In some instances, it is referred to as pCas9-TruTK1-A/A.

SEQ ID NO: 3

```
ctctgcttggacggacaggatgtatgctgtggctatttaaggataactaccttgggggccattcattgattccaactccgggatctggt
cacgcagggcaaaaaagctccgttttagctcgttcctcctctggcgctccaagacgttgtgtgttcgcctcttgacattctcctcggtg
tccgagggcctgtgtgaatttgttatccgctcacaattccacacagacgtcgttgacaattaatcatcggcatagtatatcggcatag
tataatacgacaaggtgaggaactaaaccatggccaagttgaccagtgccgttccggtgctcaccgcgcgcgacgtcgccggagcggtc
gagttctggaccgaccggctcgggttctcccgggacttcgtggaggacgacttcgccggtgtggtccgggacgacgtgaccctgttcat
cagcgcggtccaggaccaggtggtgccggacaacaccctggcctgggtgtgggtgcgcggcctggacgagctgtacgccgagtggtcgg
aggtcgtgtccacgaacttccgggacgcctccgggccggccatgaccgagatcggcgagcagccgtggggcgggagttcgccctgcgc
gacccggccggcaactgcgtgcacttcgtggccgaggagcaggactgagagctcgcttggactcctgttgatagatccagtaatgacct
cagaactccatctggatttgttcagaacgctcggttgccgccgggcgttttttattggtgagaatccaagcactagtaacaacttatat
cgtatgggctgacttcaggtgctacatttgaagagataaattgcactgaaatctagtaatattttatctgattaataagatgatcttc
ttgagatcgttttggtctgcgcgtaatctcttgctctgaaaacgaaaaaaccgccttgcagggcggtattcgaaggttctctgagctac
caactctagaaccgaggtaactggcttggaggagcgcagtcaccaaaacttgtcctttcagtttagccttaaccggcgcatgacttcaa
gactaactcctctaaatcaattaccagtggctgctgccagtggtgcttttgcatgtcttcgggttggactcaagacgatagttaccg
gataaggcgcagcggtcggactgaacgggggttcgtgcatacagtccagctggagcgaactgcctacccggaactgagtgtcaggcg
tggaatgagacaaacgcggccataacagcggaatgacaccggtaaaccgaaaggcaggaacaggagagcgcacgagggagccgccaggg
ggaaacgcctggtatctttatagtcctgtcgggtacgccaccactgatttgagcgtcagatttcgtgatgcttgtcaggggcggagc
ctatggaaaaacggctttgccgcggccctctcacttccctgttaagtatcttcctggcatcttccaggaaatctccgccccgttcgtaa
```

-continued

```
gccatttccgctcgccgcagtcgaacgaccgagcgtagcgagtcagtgagcgaggaagcggaatatatccctaggtctagggcggcgg
atttgtcctactcaggagagcgttcaccgacaaacaacagatataaacgaaaggcccagtctttcgactgagcctttcgttttatttgat
gcctctagattacaccttcctcttcttcttggggtcagccctgctgtctccaccgagctgagagaggtcgattcttgtttcatagagcc
ccgtaattgactgatgaatcagtgtggcgtccaggacctcctttgtagaggtgtaccgctttctgtctatggtggtgtcgaagtacttg
aaggctgcaggcgcgcccaagttggtcagagtaaacaagtggataatgttttctgcctgctccctgatgggcttatccctgtgcttatt
gtaagcagaaagcaccttatcgaggttagcgtcggcgaggatcactcttttggagaattcgcttatttgctcgatgatctcatcaaggt
agtgtttgtgttgttccacgaacagctgcttctgctcattatcttcgggagacccttgagcttttcatagtggctggccagatacaag
aaattaacgtatttagaggcagtgccagctcgttaccttctgcagctcgcccgcactagcgagcattcgtttccggccgattcaagc
tcaaagagagtacttgggaagcttaatgatgaggtcattagacctctttatatcctttcgcctcgagaaagtcgatgggttttttt
cgaagcttgatcgctccatgattgtgatgccagcagttccttgacgcttagagttttttagacttccctttctccactttggccacaa
ccagtacactgtaagcgactgtaggagaatcgaatccgccgtatttcttggggtcccaatctttttgcgtgcgatcagcttgtcgctg
ttccttttcgggaggatactttccttggagaagcctccggtctgtacttcggtctattaacgatgttcacctgcggcatggacaggacc
ttccggactgtcgcgaaatccctaccctgtcccacacgatttctcctgttcctccgtttgtttcgataagtggtcgcttccgaatctc
tccattggccagtgtaatctcggtcttgaaaaaattcataatattgctgtaaaagaagtacttagcggtggccttgcctatttcctgct
cagactttgcgatcattttcctaacatcgtacactttatagtctccgtaaacaaattcagattcaagcttgggatatttttgataagt
gcagtgcctaccactgcattcaggtaggcatcatgcgcatggtggtaattgttgatctctctcaccttataaaactgaaagtcctttct
gaaatctgagaccagcttagacttcagagtaataactttcacctctcgaatcagtttgtcattttcatcgtacttggtgttcatgcgtg
aatcgagaatttgggccacgtgcttggtgatctggcgtgtctcaacaagctgccttttgatgaagccggctttatccaactcagacagg
ccacctcgttcagccttagtcagattatcgaacttccgttgtgtgatcagtttggcgttcagcagctgccgccaataatttttcattac
ttgacaacttcttctgaggggacgttatcactcttccctctattttttatcggatcttgtcaacactttattatcaatagaatcatcttt
gagaaaagactgggcacgatatgatccacgtcgtagtcggagagccgattgatgtccagttcctgatccacgtacatgtccctgccgt
tctgcaggtagtacaggtagagcttctcattctgaagctgggtgttttcaactgggtgttccttaaggatttgggaccccagttcttt
atacctcttcaatcctcttcatcctttccctactgttcttctgtccctctgggtagtttggtctctcggccatctcgataacgat
attctcgggcttatgccttcccattactttgacgagttcatccacgacctaacggtctgcagtattccctattgatagctgggctacc
tgcaagattagcgatgtgctcgtgaagactgtcccctggccagaaacttgtgctttctggatgtcctccttaaaggtgagagagtcat
catggatcaactgcatgaagttccggttggcaaatccatcggacttaagaaaatccaggattgtctttccactctgcttgtctcggatc
ccattgatcagttttcttgacagccgcccccatcctgtatatcggcgcctcttgagctgtttcatgactttgtcgtcgaagagatgagc
gtaagttttcaagcgttcttcaatcatctccctatcttcaaacaacgtaagggtgaggacaatgtcctcaagaatgtcctcgttctcct
cattgtccaggaagtccttgtctttaatgattttcaggagatcgtgatacgttcccagggatgcgttgaagcgatcctccactccgctg
atttcaacagagtcgaaacattcaatctttttgaaatagtcttctttgagctgttttcacggtaactttccggttcgtcttgaagagga
ggtccacgatagctttcttctgctctccagacaggaatgctggctttctcatcccttctgtgacgtatttgaccttggtgagctcgtta
taaactgtgaagtactcgtacagcagagagtgttttaggaagcaccttttcgttaggcagattttttatcaaagttagtcatccttttcg
atgaaggactgggcagaggccccccttatccacgacttcctcgaagttccagggagtgatggtctcttctgatttgcgagtcatccacgc
gaatctggaatttccccggggcgaggggcctacatagtagggtatccgaaatgtgaggattttctcaatcttttccctgttatctacaa
aaagggtagaaatcctcttgccgcctgaggatagcgtgcagttcgcccaggtgaatctggtggggatgcttccattgtcgaaagtgc
gctgtttgcgcaacagatcttctctgttaagctttaccagcagctcctcggtgccgtccattattccaagatgggcttaataaatttgt
aaaattcctcctggcttgctccgccgtcaatgtatccggcgtagccattttagactgatcgaagaaaatttccttgtacttctcaggc
agttgctgtctgacaagggccttcagcaaagtcaagtcttggtggtgctcatcatagcgcttgatcatactagcgctcagcggagcttt
ggtgatctccgtgttcactcgcagaatatcactcagcagaatggcgtctgacaggttcttttgccgccaaaaaaggtctgcgtactgg
tcgccgatctgggccagcagattgtcgagatcatcatcgtaggtgtctttgctcagttgaagcttggcatcttcggccaggtcgaagtt
agatttaaagttgggggtcagcccgagtgacagggcgataagattaccaaacaggccgttcttcttctccccagggagctgtgcgatga
```

-continued

```
ggttttcgagccgccgggatttggacagcctagcgctcaggattgattggcgtcaactccggatgcgttgatcgggttctcttcgaaa agctgattgtaagtctgaaccagttggataaagagtttgtcgacatcgctgttgtctgggttcaggtcccctcgatgaggaagtgtcc ccgaaatttgatcatatgcgccagcgcgagatagatcaaccgcaagtcagccttatcagtactgtctacaagcttcttcctcagatgat atatggttgggtacttttcatggtacgccacctcgtccacgatattgccaaagattgggtggcgctcgtgctattatcctcctccacca aaaaggactcctccagcctatggaagaaagagtcatccaccttagccatctcattactaaagatctcctgcaggtagcagatccgattc ttttctgcgggtatatctgcgccgtgctgttcttttgagccgcgtggcttcggcGgtTtccccggagtcgaacaggagggcgccaatga ggttcttctttatgctgtggcgatcggtattgcccagaactttgaattattgctcggcaccttgtactcgtccgtaatgacggcccagc cgacgctgtttgtgccgatatcgagcccaatggagtacttcttgtccatgggtaccttttctcctctttaatgaattctgtgtgaaatt gttatccgctcacaattgaatctatcataattgtgagcgctcacaattgtaaaggtttagatctaaaactagtggcagcggctaactaa gcggcctgctgactactcgccgatcaaaaggcattagctattaagggattgacgagggcgtatctgcgcagtaagaTGCGgcattGTTG TGTGGAAATGTGAGgttttagagctagaaatagcaagttaaaataaggctagtccgttatcaacttgaaaaagtggcaccgagtcggtg ctttttttaattcgaaaagcgctcaacgagcaggctttttggtcgacagACAGtagtggcagcggctaactaagcggcctgctgacta ctcgccgatcaaaaggcattagctattaagggattgacgagggcgtatctgcgcagtaagatgcgccccgcattTGTTGTGTGGAATGT GAGgttttagagctagaaatagcaagttaaaataaggctagtccgttatcaacttgaaaaagtggcaccgagtcggtgctttttttaat tcgaaaagcctgctcaacgagcaggcttttttggtcgacagttcataggtgattgctcaggacatttctgttagaaggaatcgtttcc ttactttccttacgcacaagagttccgtagctgttcaagtttgtgtttcaactgttctcgtcgtttccgcaacaagtcctcttcagaa atgagcttttgctc
```

A plasmid described herein is illustrated by SEQ ID NO: 4. In some instances, it is referred to as pCas9-hGFP-N/0 master sequence.

SEQ ID NO: 4
```
ctctgcttggacggacaggatgtatgctgtggctatttaaggataactaccttgggggccattcattgattccaactccgggatctggt cacgcagggcaaaaaagctccgttttagctcgttcctcctctggcgctccaagacgttgtgtgttcgcctcttgacattctcctcggtg tccgagggccctgtgtgaatttgttatccgctcacaattccacacagacgtcgttgacaattaatcatcggcatagtatatcggcatag tataatacgacaaggtgaggaactaaaccatggccaagttgaccagtgccgttccggtgctcaccgcgcgcgacgtcgccggagcggtc gagttctggaccgaccggctcgggttctcccgggacttcgtggaggacgacttcgccggtgtggtccgggacgacgtgaccctgttcat cagcgcggtccaggaccaggtggtgccggacaacaccctggcctgggtgtgggtgcgcggcctggacgagctgtacgccgagtggtcgg aggtcgtgtccacgaacttccgggacgcctccggcggccatgaccgagatcggcgagcagccgtggggcgggagttcgccctgcgc gacccggccggcaactgcgtgcacttcgtggccgaggagcaggactgagagctcgcttggactcctgttgatagatccagtaatgacct cagaactccatctggatttgttcagaacgctcggttgccgccgggcgttttttattggtgagaatccaagcactagtaacaacttatat cgtatgggctgacttcaggtgctacatttgaagagataaattgcactgaaatctagtaatattttatctgattaataagatgatcttc ttgagatcgttttggtctgcgcgtaatctcttgctctgaaaacgaaaaaaccgccttgcagggcggtattcgaaggttctctgagctac caactctagaaccgaggtaactggcttggaggagcgcagtcaccaaaacttgtcctttcagtttagccttaaccggcgcatgacttcaa gactaactcctctaaatcaattaccagtggctgctgccagtggtgcttttgcatgtctttccgggttggactcaagacgatagttaccg gataaggcgcagcggtcggactgaacgggggggttcgtgcatacagtccagcttggagcgaactgcctacccggaactgagtgtcaggcg tggaatgagacaaacgcggccataacagcggaatgacaccggtaaaccgaaaggcaggaacaggagagcgcacgagggagccgccaggg ggaaacgcctggtatctttatagtcctgtcgggtacgccaccactgatttgagcgtcagatttcgtgatgcttgtcaggggggcggagc ctatggaaaaacggctttgccgcggccctctcacttccctgttaagtatcttcctggcatcttccaggaaatctccgccccgttcgtaa gccatttccgctcgccgcagtcgaacgaccgagcgtagcgagtcagtgagcgaggaagcggaatatatcccctaggtctagggcggcgg atttgtcctactcaggagagcgttcaccgacaaacaacagataaaacgaaaggcccagtctttcgactgagcctttcgttttatttgat
```

-continued

```
gcctctagattacaccttcctcttcttcttggggtcagccctgctgtctccaccgagctgagagaggtcgattcttgtttcatagagcc
ccgtaattgactgatgaatcagtgtggcgtccaggacctcctttgtagaggtgtaccgctttctgtctatggtggtgtcgaagtacttg
aaggctgcaggcgcgcccaagttggtcagagtaaacaagtggataatgttttctgcctgctccctgatgggcttatccctgtgcttatt
gtaagcagaaagcaccttatcgaggttagcgtcggcgaggatcactcttttggagaattcgcttatttgctcgatgatctcatcaaggt
agtgtttgtgttgttccacgaacagctgcttctgctcattatcttcgggagaccctttgagcttttcatagtggctggccagatacaag
aaattaacgtatttagagggcagtgccagctcgttacctttctgcagctcgcccgcactagcgagcattcgtttccggccgattcaagc
tcaaagagagagtacttgggaagcttaatgatgaggtcattagacctctttatatcctttcgcctcgagaaagtcgatgggttttttt
cgaagcttgatcgctccatgattgtgatgcccagcagttccttgacgcttttgagttttttagacttccctttctccactttggccaca
accagtacactgtaagcgactgtaggagaatcgaatccgccgtatttcttggggtcccaatcttttttgcgtgcgatcagcttgtcgct
gttccttttcgggaggatactttccttggagaagcctccggtctgtacttcggtctattaacgatgttcacctgcgcgcatggacaggac
cttccggactgtcgcgaaatccctaccctgtgtcccacacgatttctcctgtttctccgtttgtttcgataagtggtcgcttccgaatct
ctccattggccagtgtaatctcggtcttgaaaaaattcataatattgctgtaaaagaagtacttagcggtggccttgcctatttcctgc
tcagactttgcgatcattttcctaacatcgtacactttatagtctccgtaaacaaattcagattcaagcttgggatattttttgataag
tgcagtgcctaccactgcattcaggtaggcatcatgcgcatggtggtaattgttgatctctctcaccttataaaactgaaagtcctttc
tgaaatctgagaccagcttagacttcagagtaataactttcacctctcgaatcagtttgtcattttcatcgtacttggtgttcatgcgt
gaatcgagaatttgggccacgtgcttggtgatctggcgtgtctcaacaagctgccttttgatgaagccggctttatccaactcagacag
gccacctcgttcagccttagtcagattatcgaacttccgttgtgtgatcagtttggcgttcagcagctgccgccaataatttttcatta
cttgacaacttcttctgaggggacgttatcactcttccctctattttatcggatcttgtcaacactttattatcaatagaatcatctt
tgagaaaagactggggcacgatatgatccacgtcgtagtcggagagccgattgatgtccagttcctgatccacgtacatgtccctgccg
ttctgcaggtagtacaggtagagctctcattctgaagctgggtgttttcaactgggtgttccttaaggatttgggaccccagttcttt
tatccctcttcaatcctcttcatcctttccctactgttcttctgtcccttctgggtagtttggttctctcgggccatctcgataacga
tattctcgggcttatgccttcccattactttgacgagttcatccacgacctttaacggtctgcagtattccctttttgatagctgggcta
cctgcaagattagcgatgtgctcgtgaagactgtcccctggccagaaacttgtgctttctggatgtcctccttaaaggtgagagagtc
atcatggatcaactgcatgaagttccggttggcaaatccatcggacttaagaaaatccaggattgtctttccactctgcttgtctcgga
tcccattgatcagttttcttgacagccgcccccatcctgtatatcggcgcctcttgagctgtttcatgactttgtcgtcgaagagatga
gcgtaagttttcaagcgttcttcaatcatctcccctatcttcaaacaacgtaagggtgaggacaatgtcctcaagaatgtcctcgttctc
ctcattgtccaggaagtccttgtctttaatgattttcaggagatcgtgatacgttcccagggatgcgttgaagcgatcctccactccgc
tgatttcaacagagtcgaaacattcaatcttttgaaatagtcttctttgagctgtttcacggtaactttccggttcgtcttgaagagg
aggtccacgatagattcttctgctctccagacaggaatgctggctttctcatcccttctgtgacgtatttgaccttggtgagctcgtta
taaactgtgaagtactcgtacagcagagagtgtttaggaagcaccttttcgttaggcagattttatcaaagttagtcatcctttcgat
gaaggactgggcagaggccccttatccacgacttcctcgaagttccagggagtgatggtctcttctgatttgcgagtcatccacgcga
atctggaatttccccgggcgagggggcctacatagtagggtatccgaaatgtgaggattttctcaatcttttccctgttatctacaaaa
aggggtagaaatcctcttgccgcctgaggatagcgtgcagttcgcccaggtgaatctggtggggatgcttccattgtcgaaagtgcgc
tgtttgcgcaacagatcttctctgttaagctttaccagcagctcctcggtgccgtccattattccaagatgggcttaataaatttgtaa
aattcctcctggcttgctccgccgtcaatgtatccggcgtagccatttttagactgatcgaagaaaatttccttgtacttctcaggcag
ttgctgtctgacaagggccttcagcaaagtcaagtcttggtggtgctcatcatagcgcttgatcatactagcgctcagcggagctttgg
tgatctccgtgttcactcgcagaatatcactcagcagaatggcgtctgacaggttcttgccgccaaaaaaggtctgcgtactggtcg
ccgatctgggccagcagattgtcgagatcatcatcgtaggtgtctttgctcagttgaagcttggcatcttcggccaggtcgaagttaga
tttaaagttgggggtcagcccgagtgacagggcgataagattaccaaacaggccgttcttcttctccccagggagctgtgcgatgaggt
tttcgagccgccgggatttggacagcctagcgctcaggattgctttggcgtcaactccggatgcgttgatcgggttctcttcgaaaagc
tgattgtaagtctgaaccagttggataaagagtttgtcgacatcgctgttgtctgggttcaggtcccctcgatgaggaagtgtccccg
```

-continued

```
aaatttgatcatatgcgccagcgcgagatagatcaaccgcaagtcagccttatcagtactgtctacaagcttcttcctcagatgatata tggttgggtacttttcatggtacgccacctcgtccacgatattgccaaagatt gggtggcgtcgtgctattatcctcctccaccaaaa aggactcctccagcctatggaagaaagagtcatccaccttagccatctcattactaaagatctcctgcaggtagcagatccgattcttt ctgcgggtatatctgcgccgtgctgttcttttgagccgcgtggcttcggcGgtTtccccggagtcgaacaggagggcgccaatgaggtt cttctttatgctgtggcgatcggtattgcccagaacttt gaattattgctcggccacc tgtactcgtccgtaatgacggcccagccgac gctgtttgtgccgatatcgagcccaatggagtacttcttgtccatgggtacctttctcctctt taatgaattctgtgtgaaattgttat ccgctcacaattgaatctatcataattgtgagcgctcacaattgtaaaggttagatctcoaactagtggcagcggctaactaagcggcc tgctgactactcgccgatcaaaaggcattagctattaagggattgacgagggcgtatctgcgcagtaagaTGCGgcattWgttttagag ctagaaatagcaagttaaaataaggctagtccgttatcaacttgaaaaagtggcaccgagtcggtgctttttttaattcgaaaagcgct caacgagcaggctataggtcgacagACAGtagtggcagcggctaactaagcggcctgctgactttctcgccgatcaaaaggcattttgc tattaagggattgacgagggcgtatctgcgcagtaagatgcgccccgcattYgttttagagctagaaatagcaagttaaaataaggcta gtccgttatcaacttgaaaaagtggcaccgagtcggtgctttttttaattcgaaaagcctgctcaacgagcaggctataggtcgacagt tcataggtgattgctcaggacatttctgttagaaggaatcgttttccttacttaccttacgcacaagagttccgtagctgttcaagttt gtgtttcaactgttctcgtcgtttccgcaacaagtcctcttcagaaatgagctatgctc
```

The following Table 2 illustrates sgRNA sequences in a pCas9-hGFP-N/0 plasmid.

| | | | |
|---|---|---|---|
| hGFP12-A/Δ: | sgRNA 1: | CCAGGATGGGCACCAACC | (SEQ ID NO: 5) |
| | sgRNA 2: | ACCAGGATGGGCACCACC | (SEQ ID NO: 6) |
| hGFP12-G/Δ: | sgRNA 1: | CCAGGATGGGCACCAGCC | (SEQ ID NO: 7) |
| | sgRNA 2: | ACCAGGATGGGCACCACC | (SEQ ID NO: 8) |
| hGFP12-C/Δ: | sgRNA 1: | CCAGGATGGGCACCACCC | (SEQ ID NO: 9) |
| | sgRNA 2: | ACCAGGATGGGCACCACC | (SEQ ID NO: 10) |
| hGFP12-T/Δ: | sgRNA 1: | CCAGGATGGGCACCATCC | (SEQ ID NO: 11) |
| | sgRNA 2: | ACCAGGATGGGCACCACC | (SEQ ID NO: 12) |
| hGFP13-A/Δ: | sgRNA 1: | CCAGGATGGGAACCACCC | (SEQ ID NO: 13) |
| | sgRNA 2: | ACCAGGATGGGACCACCC | (SEQ ID NO: 14) |
| hGFP13-G/Δ: | sgRNA 1: | CCAGGATGGGACCACCC | (SEQ ID NO: 15) |
| | sgRNA 2: | ACCAGGATGGGACCACCC | (SEQ ID NO: 16) |
| hGFP13-C/Δ: | sgRNA 1: | CCAGGATGGGCACCACCC | (SEQ ID NO: 17) |
| | sgRNA 2: | ACCAGGATGGGACCACCC | (SEQ ID NO: 18) |
| hGFP13-T/Δ: | sgRNA 1: | CCAGGATGGGTACCACCC | (SEQ ID NO: 19) |
| | sgRNA 2: | ACCAGGATGGGACCACCC | (SEQ ID NO: 20) |
| hGFP16-A/Δ: | sgRNA 1: | CCAAGATGGGCACCACCC | (SEQ ID NO: 21) |
| | sgRNA 2: | ACCAGATGGGCACCACCC | (SEQ ID NO: 22) |
| hGFP16-G/Δ: | sgRNA 1: | CCAGGATGGGCACCACCC | (SEQ ID NO: 23) |
| | sgRNA 2: | ACCAGATGGGCACCACCC | (SEQ ID NO: 24) |
| hGFP16-C/Δ: | sgRNA 1: | CCACGATGGGCACCACCC | (SEQ ID NO: 25) |
| | sgRNA 2: | ACCAGATGGGCACCACCC | (SEQ ID NO: 26) |
| hGFP16-T/Δ: | sgRNA 1: | CCATGATGGGCACCACCC | (SEQ ID NO: 27) |
| | sgRNA 2: | ACCAGATGGGCACCACCC | (SEQ ID NO: 28) |

The following Table 3 illustrates sgRNA sequences used in one or more of a method, composition, cell, engineered microorganism described herein.

| | | |
|---|---|---|
| GFP151-GXC | TCACACAATGTAGXCATCACGG | (SEQ ID NO: 29) |
| GFP12-YTG | ACCAGGATGGGCACCAYCCCGG | (SEQ ID NO: 30) |
| hGFP16-YTG | ACCAYGATGGGCACCACCCCGG | (SEQ ID NO: 31) |
| GFP151-XAG | TCACACAATGTAXAGATCACGG | (SEQ ID NO: 32) |
| hGFP12-XTG | ACCAGGATGGGCACCAXCCCCGG | (SEQ ID NO: 33) |
| TK1-NC-AXT | TGTTGTGTGGAAXTGTGAGCGG | (SEQ ID NO: 34) |
| GFP66-YGC | TTGTCACTACTCTGACCYGCGG | (SEQ ID NO: 35) |
| GFP66-XAG | TTGTCACTACTCTGACCXAGGG | (SEQ ID NO: 36) |
| GFP151-CXC | TCACACAATGTACXCATCACGG | (SEQ ID NO: 37) |
| hGFP16-YTG | ACCAXGATGGGCACCACCCCGG | (SEQ ID NO: 38) |
| GFP151-TXG | TCACACAATGTATXGATCACGG | (SEQ ID NO: 39) |
| GFP151-TYA | TCACACAATGTATYAATCACGG | (SEQ ID NO: 40) | hGFP13-GYA  ACCAGGATGGGXACCACCCCGG (SEQ ID NO: 41)

D8-NC-TXT   ATTCACAATACTXTCTTTAAGG (SEQ ID NO: 42)

While preferred embodiments of the disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the invention and that methods and structures within the scope of these claims and their equivalents be covered thereby.

What is claimed is:

1. A cell comprising:
   (I) a first nucleic acid sequence comprising an unnatural nucleotide, wherein the unnatural nucleotide does not substantially form a base pair with a natural nucleotide; and
   (II) a second nucleic acid sequence encoding a CRISPR/Cas system, wherein the CRISPR/Cas system encodes a single guide RNA (sgRNA) comprising a crRNA-tracrRNA scaffold and a target motif that is complementary to a modified nucleic acid sequence, and wherein the modified nucleic acid sequence is identical to the first nucleic acid sequence except that it comprises: (1) a substitution of the unnatural nucleotide with a natural nucleotide or (2) a single nucleotide deletion at the unnatural nucleotide position.

2. The cell of claim 1, wherein one or more plasmids comprise the second nucleic acid sequence encoding the CRISPR/Cas system and the first nucleic acid sequence comprising the unnatural nucleotide.

3. The cell of claim 1, wherein the modified nucleic acid comprises a substitution of the unnatural nucleotide with a natural nucleotide.

4. The cell of claim 1, wherein the sgRNA further comprises a protospacer adjacent motif (PAM) recognition element.

5. The cell of claim 4, wherein a nucleotide within the target motif that recognizes the substituted natural nucleotide of the modified nucleic acid sequence is located between 3 to 22, between 5 to 20, between 5 to 18, between 5 to 15, between 5 to 12, or between 5 to 10 nucleotides from the 5' terminus of the PAM recognition element.

6. The cell of claim 1, wherein the CRISPR/Cas system comprises a wild-type Cas9 polypeptide.

7. The cell of claim 1, wherein the unnatural nucleotide comprises an unnatural base selected from

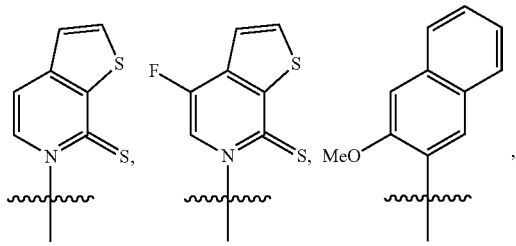

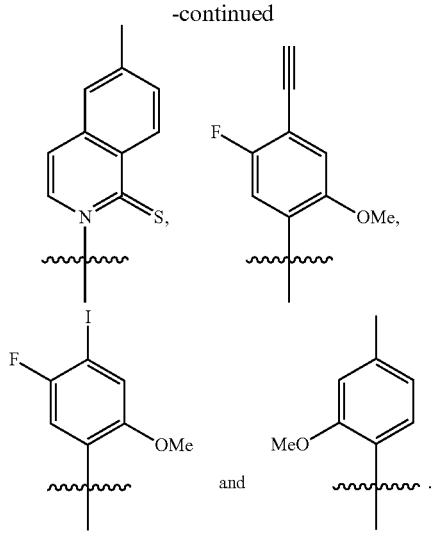

8. The cell of claim 1, further comprising a third nucleic acid sequence that encodes an additional single guide RNA (sgRNA) comprising a crRNA-tracrRNA scaffold.

9. The cell of claim 1, wherein the first nucleic acid sequence comprising the unnatural nucleotide further comprises an additional unnatural nucleotide.

10. The cell of claim 1, wherein the cell is *E. coli*.

11. A cell comprising:
   (I) a first nucleic acid sequence comprising an unnatural nucleotide, wherein the unnatural nucleotide does not substantially form a base pair with a natural nucleotide; and
   (II) one or more second nucleic acid sequences encoding a CRISPR/Cas system, wherein the CRISPR/Cas system encodes two or more single guide RNAs (sgRNAs), each of which comprises a crRNA-tracrRNA scaffold and wherein each sgRNA comprises a target motif that is complementary to a modified nucleic acid sequence, and wherein the modified nucleic acid sequence is identical to the first nucleic acid sequence except that it comprises: (1) a substitution of the unnatural nucleotide with a natural nucleotide or (2) a single nucleotide deletion at the unnatural nucleotide position.

* * * * *